United States Patent
Ni et al.

(10) Patent No.: US 10,155,802 B2
(45) Date of Patent: Dec. 18, 2018

(54) LOCALLY-ACTIVE ANTICOAGULANTS AND ANTI-INFLAMMATORY AGENTS

(75) Inventors: Feng Ni, Pierrefonds (CA); Ping Xu, St. Laurent (CA); Sazzard Hossain, Pointe-Claire (CA); Dmitri Tolkatchev, La Prairie (CA); Kenji Tonan, Osaka (JP)

(73) Assignee: National Research Council of Canada, Ottawa (CA)

(*) Notice: Subject to any disclaimer, the term of this patent is extended or adjusted under 35 U.S.C. 154(b) by 0 days.

(21) Appl. No.: 14/112,565

(22) PCT Filed: Apr. 13, 2012

(86) PCT No.: PCT/CA2012/000350
§ 371 (c)(1),
(2), (4) Date: Jan. 10, 2014

(87) PCT Pub. No.: WO2012/142696
PCT Pub. Date: Oct. 26, 2012

(65) Prior Publication Data
US 2014/0113854 A1    Apr. 24, 2014

Related U.S. Application Data

(60) Provisional application No. 61/477,343, filed on Apr. 20, 2011.

(51) Int. Cl.
| | |
|---|---|
| C07K 14/745 | (2006.01) |
| C07K 14/81 | (2006.01) |
| C12N 9/74 | (2006.01) |
| C07K 5/107 | (2006.01) |
| C07K 16/36 | (2006.01) |
| A61K 38/00 | (2006.01) |

(52) U.S. Cl.
CPC .......... *C07K 14/745* (2013.01); *C07K 5/1016* (2013.01); *C07K 14/811* (2013.01); *C07K 16/36* (2013.01); *C12N 9/6429* (2013.01); *C12Y 304/21005* (2013.01); *A61K 38/00* (2013.01); *C07K 2319/00* (2013.01); *C07K 2319/70* (2013.01)

(58) Field of Classification Search
None
See application file for complete search history.

(56) References Cited

U.S. PATENT DOCUMENTS 8,063,018 B2 * 11/2011 Ni et al. .................. 514/14.7
2002/0150631 A1 * 10/2002 Merril .................. A61K 31/155 424/671
2003/0175799 A1 * 9/2003 Cochran et al. ............ 435/7.1

FOREIGN PATENT DOCUMENTS

WO    WO2006000081    *    1/2006

OTHER PUBLICATIONS

CUNY (retrieved from http://academic.brooklyn.cuny.edu/biology/bio4fv/page/enz_act.htm on Apr. 3, 2015, 2 pages).*
Rieke et al ('MR Thermometry' J Magn Reson Imaging Feb. 2008 v27(2) pp. 376-390, printed out as pp. 1-30).*
Suzuki M ('What is "hypermobile" water?:detected in alkali halide, adenosine phosphate, and F-actin solutions by high-resolution microwave dielectric spectroscopy' Pure Appl Chem 2014 v86(2) pp. 181-189).*
Samudrala R ('Protein folding and protein structure prediction' retrieved from http://www.iscb.org/cms_addon/conferences/ismb2000/tutorials/samudrala.html on Apr. 3, 2015, 3 pages).*
Correa et al. ('A graph-structural method for prediction of polymer properties' Brazilian Journal of Chemical Engineering v21(4) Oct.-Dec. 2004 pp. 621-628).*
Mena-Ulecia et al. ('Study of the differential activity of thrombin inhibitors using docking, QSAR, molecular dynamics, and MM-GBSA' PLOS ONE Nov. 24, 2015 pp. 1-21).*
Oxford Genetics (retrieved from http://www.oxfordgenetics.com/SiteContent/TeamResources/cleavage-tag-guide on Jul. 10, 2017, 2 pages).*

* cited by examiner

*Primary Examiner* — Karlheinz R. Skowronek
*Assistant Examiner* — Ronald T Niebauer
(74) *Attorney, Agent, or Firm* — Roula Thomas

(57) ABSTRACT

A locally-activatable bivalent thrombin binding agent is provided having two thrombin binding moieties for non-overlapping sites on a surface of thrombin linked together by a linker. The linker is a polypeptide having 5 to 30 amino acid residues existing in a folded state under an environmental condition where the binding agent is inactive. The linker changes conformation from the folded state to an unfolded state in response to a change in bulk temperature and/or to the presence of hyper-mobile water thereby activating the binding agent. Such locally-activatable thrombin binding agents can be administered systemically while only targeting specific sites of coagulation or inflammation since the thrombin binding agent will only activate at the site where the existence of atherosclerotic plaques has changed the local bulk temperature and/or created hyper-mobile water sufficiently to unfold the linker and activate the binding agent. Such binding agents are useful as site-specific anti-coagulant, anti-thrombotic and/or anti¬inflammatory agents.

15 Claims, 32 Drawing Sheets
Specification includes a Sequence Listing.

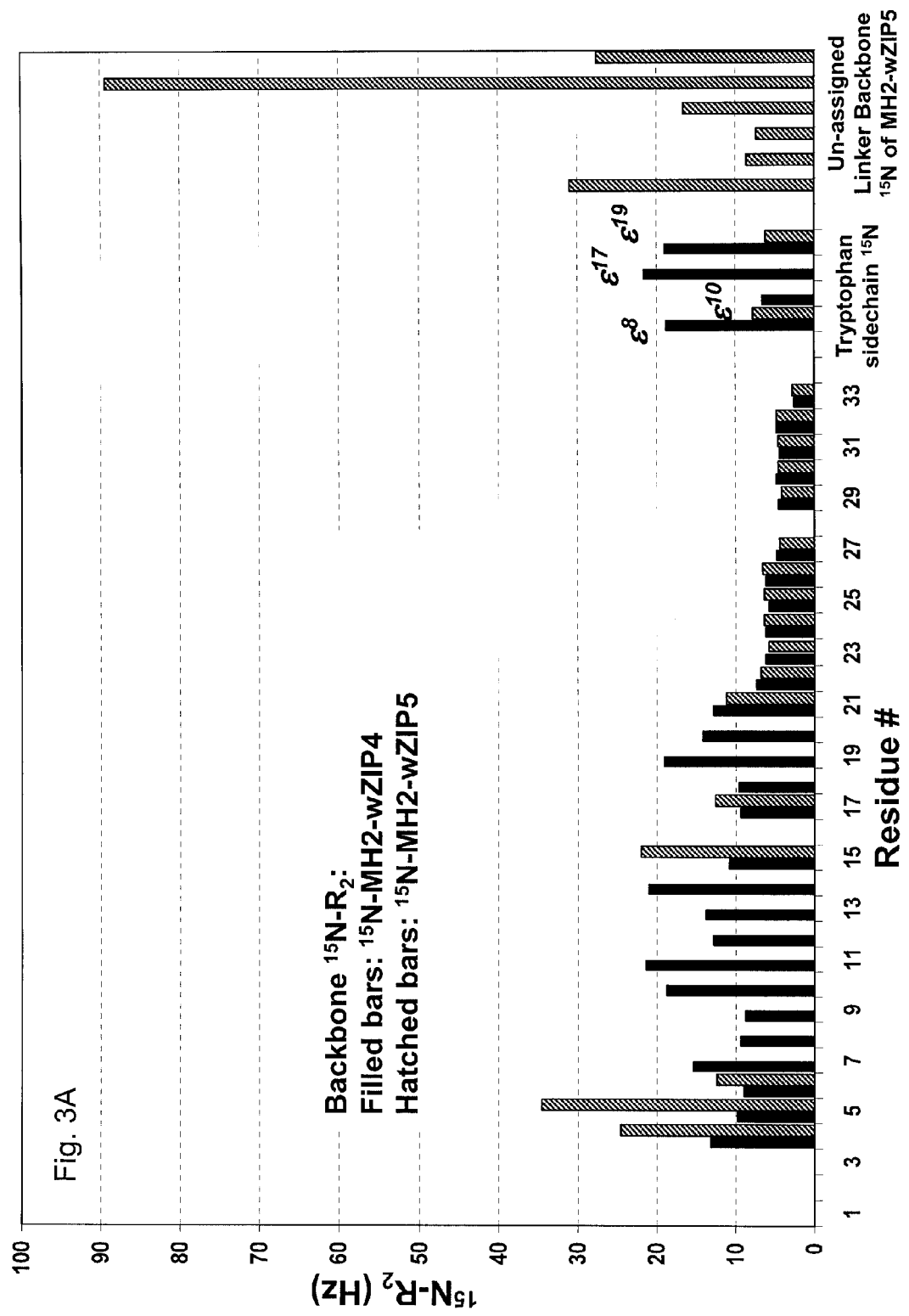

LOCALLY-ACTIVE ANTICOAGULANTS AND ANTI-INFLAMMATORY AGENTS

RELATED APPLICATIONS

This application is a national stage filing under 35 U.S.C. § 371 of International Patent Application PCT/CA2012/000350 filed Apr. 13, 2012, which claims the benefit of U.S. Provisional Application Ser. No. 61/477,343 filed Apr. 20, 2011, the disclosure of each of which is incorporated by reference herein in its entirety.

FIELD OF THE INVENTION

The present invention is related to novel thrombin inhibitors as anti-thrombotic agents and locally-active anticoagulants and anti-inflammatory agents.

BACKGROUND OF THE INVENTION

Thrombotic complications constitute major life-threatening conditions for both the aging population and young adults (Hansson 2006; Libby 2005). One underlying cause is the activation of the blood coagulation cascade and fibrin deposition, which can generate occlusive blood clots and impede blood flow, leading to thromboembolism, deep-vein thrombosis, ischemic heart diseases or stroke (Libby 2005). Elevated levels of thrombin resulting from an activated coagulation cascade are associated with almost all inflammatory conditions ranging from arthritis (Morris 1994; Busso 2002; Kitamoto 2008; Flick 2011), pulmonary fibrosis (Ludwicka-Bradley 2004; Vergnolle 2009; Bogatkevich 2011), inflammatory bowl diseases (Vergnolle 2009; Saibeni 2010) to cancer (Khorana 2004; Karimi 2010). Active deposition of fibrin occurs within atherosclerotic plaques, which promote the progression of atherosclerosis toward occlusive eruptions (Duguid 1946; Peters 2009). Extravascular fibrin deposition is a major pathogenic factor for chronic synovial inflammation in arthritis, especially in osteoarthritis and rheumatoid arthritis (So 2003; Busso 2002). Thrombosis increases the lethality of many human cancers (Agorogiannis 2002; Khorana 2004; Rak 2006; Lorenzet 2002; Ornstein 2002; Nierodzik 2005; Karimi 2010) and infectious diseases (Levi 2003; Marsden 2003; Opal 2003). Such widespread occurrence and unmet medical needs have propelled a continued search for more efficacious, safe and cost-effective anti-coagulant and anti-thrombotic therapies (Gross 2008; Hoppensteadt 2008; Theroux 2000; Warkentin 2004) and a better understanding of blood coagulation biochemistry (Mann 2006; Kamath 2008; Bock 2007; Wood 2011). These latest research advances present a unique opportunity for the design, discovery and development of anti-thrombotic agents specific to the localized characteristics of vascular lesions, atherosclerotic plaques and inflamed joints and tissues.

The blood coagulation cascade is triggered by the expression of tissue factor on injured vasculatures or tissue cells (Mann 2006; Mann 1988), e.g. at sites of atherosclerotic lesions (Libby 2005) and within inflamed joints (Busso 2002) or invasive tumors (Khorana 2004; Karimi 2010). All coagulation pathways converge on the prothrombinase assembly, which rapidly converts prothrombin into the ultimate protease thrombin responsible for the formation of the blood (fibrin) clot (Mann 1987; Mann 1988). Generation of thrombin requires finely orchestrated cleavages of two peptide bonds in prothrombin by the prothrombinase composed of the serine protease factor (F) Xa, and the protein cofactor Va, which are assembled on appropriate membranes in the presence of $Ca^{2+}$ ions (Mann 1988; Mann 1987; Wood 2011). Depending on the physiological contexts, prothrombin activation can also accumulate thrombin in anti-coagulant and anti-inflammatory forms (Nesheim 2003; Hackeng 1996; Asai 2004; Nishimura 2007), especially in complexes with membrane-bound thrombomodulin (Nesheim 2003) instead of the fully-procoagulant and circulating form needed for the rapid formation of platelet-rich haemostatic plugs (Wood 2011).

The current generation of coagulation inhibitors, among which many are direct thrombin or FXa inhibitors, are administered and active systemically (Vorchheimer 2002; Hoppensteadt 2008; Gross 2008; Gresele 2002), and as such can cause either bleeding side effects or rebound coagulation and re-occlusion after cessation of therapy (Gresele 2002; Fareed 2008; Weitz 2002; Vorchheimer 2002). By design, these coagulation inhibitors reduce and deplete the levels of thrombin non-discriminatively, irrespective of the pro-coagulant or anti-coagulant activities of thrombin (Nesheim 2003). These complications point to the need for more effective and selective anticoagulants, especially for locally-active thrombin inhibitors to prevent pathogenic blood coagulation only at sites of occlusive vascular and/or tissue injury (Riewald 2002; Khrenov 2002; Libby 2002; Busso 2002).

SUMMARY OF THE INVENTION

There is therefore provided a new generation of bivalent thrombin inhibitors incorporating novel polypeptide linkers to confer site-specific anti-coagulant, anti thrombotic or anti-inflammatory activity. In particular, use of conformationally malleable polypeptide linkers endows this new generation of thrombin inhibitors with environment-sensitive action. Simultaneous (bivalent) binding of inhibitor moieties is normally repressed by a rigidly-structured state of a polypeptide linker. However, appropriate change in environmental conditions, for example a change in bulk temperature or mobility of water in the fluid and/or tissue environment, can lead to linker unfolding or opening (also referred to as denaturation) and as a consequence to the restoration of potent binding and/or inhibitory activities of bivalent molecules containing environment-sensitive linkers. Sustained thrombin inhibition under the changed environmental conditions may render these molecules more effective for preventing pathogenic blood coagulation at sites of vulnerable (and "hot") atherosclerotic plaques and/or tissue inflammation.

Thus, in one aspect of the present invention there is provided a locally-activatable bivalent thrombin binding agent of formula (I):

tbm1-linker-tbm2     (I)

wherein: tbm1 and tbm2 are binding moieties for non-overlapping sites on a surface of thrombin; and, linker is a polypeptide consisting essentially of 5 to 30 amino acid residues existing in a folded state under a first environmental condition at which the binding agent is inactive, and changing conformation from the folded state to an unfolded state in response to a change in bulk temperature and/or to presence of hyper-mobile water thereby activating the bivalent binding agent.

There is further provided a method of inhibiting blood coagulation and/or inflammation at a specific site in a bloodstream or tissue of a subject, the method comprising identifying a subject in need of an anti-coagulant, antithrombotic or anti-inflammatory agent at the specific site; and, administering to the subject a bivalent thrombin binding agent of the present invention.

There is further provided a use of a bivalent thrombin binding agent of the present invention for treating blood coagulation and/or inflammation in a subject.

The present invention utilizes a difference in bulk temperature between normal circulating blood and sites of inflammation and/or utilizes the presence of hyper-mobile water at sites of inflammation caused by the existence of atherosclerotic plaques to specifically target such sites for treatment with an anti-coagulant and/or anti-inflammatory thrombin binding agent. Such sites include, for example, sites of vascular or tissue lesions, or sites of pathogenic coagulation. Because thrombin binding agents can have undesirable side-effects in the general circulatory system (e.g. systemic bleeding), it is desirable to be able to specifically target such local sites of thrombin generation, thrombin accumulation and pathogenic blood coagulation.

The erosion of atherosclerotic plaques at sites of coagulation generates heat which causes a change, preferably an increase, in bulk temperature at the site. Further, water in a fluid environment at the site of an atherosclerotic plaque is in a hyper-mobile state due to a loss of alignment or order of collagen-rich tissue arising from the fact that the plaque is an actively remodeled tissue that has not yet been aligned with surrounding tissue. Hyper-mobile water has a structure-breaking effect that also contributes to the unfolding of the linker further activating the binding agent. The bivalent thrombin binding agents of the present invention exist in an inactive (or less active) form under normal conditions in the subject's circulating body fluids (e.g. a bulk temperature of about 37° C. for humans and normally mobile or ambient water), but activate in response to a change in those conditions in local tissues (e.g. an increase in bulk temperature and/or presence of hyper-mobile water). While in the circulatory system, the thrombin binding agents of the present invention are thus either completely inactive or only partially active and are prevented from producing unwanted side-effects. Once the binding agents arrive at a site of interest, they activate in response to the change in bulk temperature and/or to the presence of hyper-mobile water at the site of interest to provide their anti-coagulant, anti-thrombotic and/or anti-inflammatory activity. Thus, it is possible to administer the thrombin binding agents of the present invention systemically, while specifically targeting the sites of inflammation and thrombin generation.

The binding agents of the present invention are particularly useful as site-specific anti-coagulants, anti-thrombotics and/or anti-inflammatory agents, especially for treating vascular or tissue lesions, atherosclerotic plaques, inflammatory joint diseases (e.g. osteoarthritis or rheumatoid arthritis), pulmonary fibrosis, inflammatory bowl diseases or cancer.

Because the binding agents respond to differences in bulk temperature between normal circulating blood and sites of inflammation and coagulation and/or to the presence of hyper-mobile water at the sites of inflammation and coagulation, the subjects for which the binding agents are useful in treating are those that have blood circulatory systems and are warm-blooded, for example mammals. Mammals include, for example, humans, cats, dogs, horses, cows, rats, mice, guinea pigs, rabbits, etc. The binding agents are particularly suitable for use in treating humans.

The locally-activatable bivalent thrombin binding agents of the present invention comprise three parts: a first thrombin binding moiety; a second thrombin binding moiety; and a linker linking the binding moieties, the linker being sensitive to changes in bulk temperature and/or to the presence of hyper-mobile water. The first thrombin binding moiety binds to one site on thrombin and the second thrombin binding moiety binds to a site on thrombin other than the site to which the first binding moiety binds. Examples of thrombin binding moieties include those well known in the art (e.g. Tolkatchev 2005; Ni 2008; Corral-Rodriguez 2010) as well as novel binding motifs discovered through panning phage display libraries (Ng 2005; Tanha 2006). One of the thrombin binding moieties preferably targets the active site (AS) of thrombin and the other preferably targets the fibrinogen-specific exosite I (ES1) or anion-binding/heparin-binding exosite II (ES2) of thrombin (Warkentin 2004). Some specific examples of thrombin binding moieties include Bbs-Arg-(D-Pip) (Tsuda 1994), (D-Phe)-Pro-Arg-(dFPR), Phe-Gln-Pro-Arg (FQPR) (SEQ ID NO: 26), Trp-Asp-Pro-Arg (WDPR) (SEQ ID NO: 27), Ile-Arg-Phe-Thr-Asp (IRFTD) (SEQ ID NO: 7), the hirudin C-terminus Gly-Asp-Phe-Glu-Glu-Ile-Pro-Glu-Glu-Tyr-Leu-Gin (GDFEEIPEEYLQ) (SEQ ID NO: 8), the haemadin C-terminus Glu-Phe-Glu-Glu-Phe-Glu-Ile-Asp-Glu-Glu-Glu-Lys (EFEEFEIDEEEK) (SEQ ID NO: 76) and PEPA1, a thrombin-specific human VH domain (Ng 2005) (EVQLQASGGGLVQSGDSLRLSCAASGRTFSTYAMG-WFRQAPGKLREFVGVISSSGYT HYTNSVRGR-FTISRDNAKNMVYLQMNSLKPEDTAVYYCAAADRR-FIATDGKQYDYWGQ GTQVTVSSLEHHHHHH) (SEQ ID NO: 77).

The linker comprises a polypeptide consisting essentially of 5 to 30 amino acid residues existing predominately in a folded state under a first environmental condition at which the binding agent is either completely inactive or only partially active, and changing conformation from the folded state to an unfolded state in response to a change in bulk temperature and/or to the presence of hyper-mobile water. Preferably, the change in bulk temperature is an increase in bulk temperature at the site of interest.

Increases in bulk temperature and hyper-mobility of water are related concepts, and may be grouped together as measurements of "heat". The non-hydrogen bonded state of water carries heat, whether as a result of the application of regular bulk temperature-dependent heat or from the loss of alignment or order of collagen-rich tissue to produce hyper-mobile water. Rotational degrees of freedom of water molecules in hyper-mobile water are higher than in ambient water (Kinoshita 2009), which accounts for the greater heat content of hyper-mobile water. Whatever the origin of the heat (bulk temperature change or hyper-mobile water), larger fractions of non-hydrogen-bonded water unfold a protein, and in the present case open the polypeptide linker and activate the bivalent thrombin binding agent. Measurement of bulk temperature is generally done using devices like temperature-sensitive dyes or thermocouples. Measurement of hyper-mobility of water, in addition to measurement of bulk temperature, may be accomplished using proton NMR frequency (PRF) shift, which is becoming a standard for in vivo thermography (Rieke 2008). Water PRF detects temperature changes as a composite of the more familiar bulk temperature and the more subtle changes in water hyper-mobility. Such composite temperatures may therefore be defined as a composite of bulk temperature and hyper-mobility of water. Changes in composite temperatures are typically 1-15° C. higher than changes in bulk temperature. The locally-activatable bivalent thrombin binding agents of the present invention may therefore be termed heat-activatable bivalent thrombin binding agents, irrespective of the origin of the heat (as measured by bulk temperature change or by the presence of hyper-mobile water) that activates the binding agents.

The increase in bulk temperature at the specific site being targeted for anticoagulation or anti-inflammation is typically 0.5-5° C., especially 1-3° C. higher than normal bulk blood temperature. Thus, for humans, the bulk temperature at the site is typically in a range of from 37.5° C. to 42° C., more typically in a range of from 38° C. to 40° C., depending on the method used to measure bulk temperatures. In the fully folded state, the binding agent is inactive as the binding moieties are not in the correct configuration for binding thrombin. Unfolding of the linker increases the statistical chance (Zhou 2001a; Zhou 2001b) for the binding moieties to reach the different binding sites on thrombin. If the linker is shorter than 5 amino acids, the bivalent binding agent cannot span the distance between the two discrete binding sites on thrombin such as the catalytic active site and the fibrinogen-recognition exosite. If the linker has more than 30 amino acids, the random-coil (denatured) conformation of the linker cannot confer an adequate avidity between the two binding moieties of the bivalent thrombin inhibitor (Tolkatchev 2005). The linker preferably comprises SEQ ID NO: 19 or SEQ ID NO: 20. In SEQ ID NO: 19, $X^5$ is preferably tryptophan (W) or tyrosine (Y). In SEQ ID NO: 19, $X^{12}$ is preferably tryptophan (W) or phenylalanine (F). In SEQ ID NO: 19, $X^{14}$ is preferably tryptophan (W) or valine (V). In SEQ ID NO: 20, $X^1$ is preferably serine (S) or threonine (T). In SEQ ID NO: 20, $X^5$ is preferably glutamic acid (E) or asparagine (N). In SEQ ID NO: 20, $X^6$ is preferably glycine (G), asparagine (N) or D-proline (p). In SEQ ID NO: 20, $X^7$ is preferably asparagine (N), serine (S) or glycine (G). In SEQ ID NO: 20, $X^8$ is preferably lysine (K) or alanine (A). In SEQ ID NO: 20, $X^{12}$ is preferably lysine (K) or asparagine (N). Particular examples of the linker comprise SEQ ID NO: 2, SEQ ID NO: 3, SEQ ID NO: 4 or SEQ ID NO: 5, SEQ ID NO: 21, SEQ ID NO: 22, SEQ ID NO: 23 or SEQ ID NO: 24.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which:

FIG. 3 illustrates the determination of the linker conformations of MH2-wZIP4 and MH2-wZIP5 by use of $^{15}$N-NMR transverse ($R_2$) relaxation rates. Solid bars in FIG. 3A are $^{15}$N-$R_2$ values of the respective residues in $^{15}$N-MH2-wZIP4 and open bars are those in $^{15}$N-MH2-wZIP5. $^{15}$N-$R_2$ values of the Trp side-chain NHs are shown on the right side as labeled by $\varepsilon^8$ (for Trp8), $\varepsilon^{10}$ (for Trp10), $\varepsilon^{17}$ (for Trp17), and $\varepsilon^{19}$ (for Trp19). $^{15}$N-$R_2$ values of unassigned linker residues of $^{15}$N-MH2-wZIP5 are shown further to the right. $^{15}$N-MH2-wZIP4 and $^{15}$N-MH2-wZIP5 samples were prepared with a concentration of about 200 μM in a buffer of 50 mM Tris-HCl, 100 mM NaCl, 0.1% PEG-8000 at pH 7.6. NMR data were collected at a temperature of 290 K with a proton carrier frequency of 800.048 MHz at 4.7 ppm and with an $^{15}$N carrier frequency of 81.068 MHz at 123 ppm. A time interval ($\tau_{CPMG}$) of 0.9 ms was used to separate the refocusing pi pulses in the CPMG sequence for the measurement of $^{15}$N-NMR transverse ($R_2$) relaxation times.

FIG. 5 illustrates dependence of the (H,$^{15}$N)-HSQC spectra of $^{15}$N-labelled MH2-wZIP4 on the (bulk) temperature and on the formation of hyper-mobile water induced by the addition of potassium iodide.

FIG. 6 illustrates the anti-coagulant activities of MH2-GS and MH2-wZIP4 as measured by the prothrombin time (thromboplastin) and activated partial thromboplastin time assays.

FIG. 12 illustrates the behavior of MH2-wZIP4 in the environment of partially-aligned collagen matrix.

FIG. 15 illustrates the determination of the cleavage rate of the thrombin-sensitive peptides, BRI-T208 (i.e. P4229) and BRI-T218 (i.e. P4238), catalyzed by thrombin. The cleavage experiments were carried out with a concentration of 75 μM for the peptides and 23 nM for thrombin in a buffer of 50 mM Tris-HCl/100 mM NaCl, 0.1% PEG-8000 at pH 7.6 and 37° C.

FIG. 18A is the one-dimensional proton NMR spectra of the linker peptide SWTWEGNK-WTWK (SEQ ID NO: 21 or trpzip1) in a PBS (phosphate-buffered saline) solution (gray dotted lines) supplemented with 50 mM sodium phosphate with the sample pH adjusted to 7.4 and in collagen hydrogels (thick black lines) formed in the presence of the peptide. Other experimental conditions are the same as used for the collection of data shown in FIG. 13. FIG. 18B and FIG. 18C show the thrombin inhibitory activities of peptides MH2-wZIP1-2G and MH2-wZIP1, designated as P4268 and P4269, respectively, in the data plots. The inhibitory activities were measured by thrombin-catalyzed substrate hydrolysis using the same experimental conditions as for BRI-T109 (P4230), BRI-T207 (P4223), BRI-T208 (P4229) and BRI-T218 (P4238) (FIG. 14).

DESCRIPTION OF PREFERRED EMBODIMENTS

Figure 1:
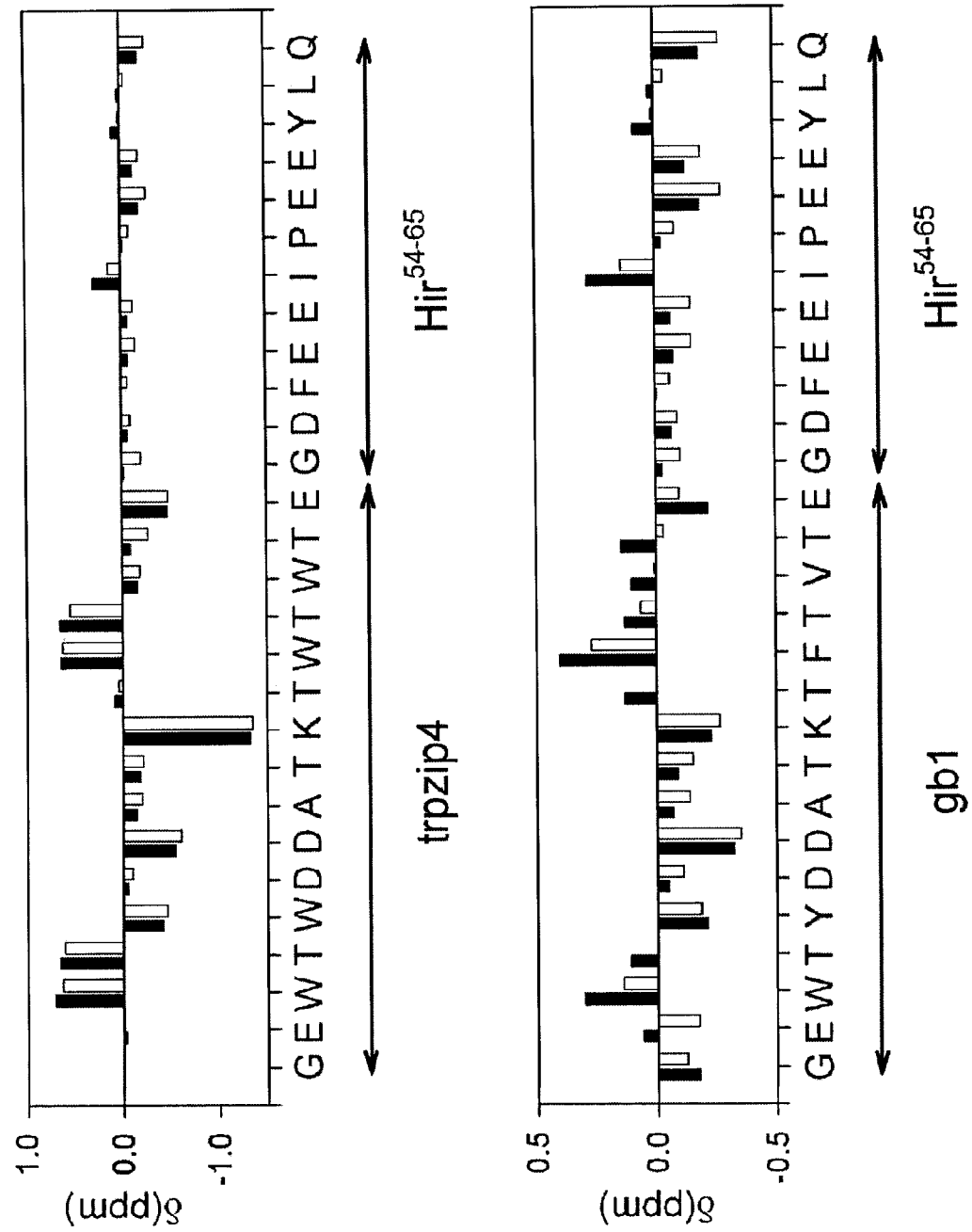
FIG. 1 illustrates $C_\alpha H$ proton ($H^\alpha$) chemical shift deviations from random coil values in the BTI5 and BTI2 peptides (Table 1), showing the persistent hairpin structure for the linker residues. Only chemical shifts for the linkers (trpzip4—SEQ ID NO: 5; gb1—SEQ ID NO: 2) and the Hir$^{54-65}$ fragments (SEQ ID NO: 8) are shown. The NMR data of BTI5 (white bars in the top panel) and BTI2 (white bars in the bottom panel) were recorded in the same conditions as reported for the isolated trpzip4 (Cochran 2001) and gb1 (Blanco 1994) peptides. Black bars represent $H^\alpha$ chemical shift deviations from random coil values for isolated trpzip4 (top panel), gb1 (bottom panel) and Hir$^{54-65}$. The values of $H^\alpha$ random coil chemical shifts were those reported previously (Wishart 1995).

Example 1: Design, Synthesis and Structural Characterization of Bivalent Thrombin Inhibitors Bivalent inhibitors of thrombin BTI1-BTI5 were constructed using as linkers eight (8) repeats of the Gly-Ser dipeptide motif ((GS)$_8$, SEQ ID NO: 1), gb1 (SEQ ID NO: 2) or self-organizing 16-residue β-hairpin peptides (SEQ ID NOs: 3-5) (Cochran 2001). The (GS)$_8$ sequence is used as a flexible linker, with which BTI1 was designed as a comparative control. Binding moieties targeting the active site (AS) and fibrinogen-specific exosite I (ES1) of thrombin are composed of peptides Bbs-Arg-(D-Pip)- and Hir$^{54-65}$, respectively, where Hir$^{54-65}$=Gly-Asp-Phe-Glu-Glu-Ile-Pro-Glu-Glu-Tyr-Leu-Gln (SEQ ID NO: 8), Bbs=4-tert-butyl-benzenesulfonyl, and D-Pip=D-pipecolic acid. The peptides were synthesized using standard Fmoc chemistry and purified by reversed-phase HPLC. Their identity was confirmed by mass-spectroscopy and NMR spectroscopy. BTI1-BTI5 peptides are shown in Table 1.

Another series of bivalent thrombin inhibitors (the MH2 series) was based on mini-hirudin 2 (abbreviated as MH2), which is derived from hirudin variant 2 (or HV2) (Bischoff 1993; Corral-Rodriguez 2010). Moieties targeting the active site (AS) and fibrinogen-specific exosite I (ES1) of thrombin are formed by peptides IRFTD (SEQ ID NO: 7) and Hir$^{54-65}$, respectively, where Hir$^{54-65}$=Gly-Asp-Phe-Glu-Glu-Ile-Pro-Glu-Glu-Tyr-Leu-Gln (SEQ ID NO: 8). The IRFTD sequence (SEQ ID NO: 7) is derived from the N-terminus of hirudin variant 2 modified to contain two amino-acid substitutions, Thr2Arg and Tyr3Phe (Lazar 1991; Winant 1991; Betz 1992), in order to increase the affinity of the IRFTDG peptide fragment (SEQ ID NO: 29) for the active site of thrombin (Table 2). As such, the IRF moiety of SEQ ID NO: 29 mimics the three naturally-occurring residues at the N-terminus of haemadin, another class of thrombin inhibitors from blood-sucking Indian leeches (Corral-Rodriguez 2010). Mini-hirudin 2 is also related to the "hirunorm" molecules (Cappiello 1998), which mimic the non-canonical binding mode of hirudin in complex with thrombin (Corral-Rodriguez 2010), but which employ rigid linker motifs and unnatural amino acids to achieve the highest possible thrombin-inhibitory activities (Lombardi 1996; De Simone 1998; Corral-Rodriguez 2010). In this invention, the linker moiety of mini-hirudin 2 is substituted by gb1 (SEQ ID NO: 2) or by a trpzip peptide (SEQ ID NOs: 3-5 and NOs 21-24) to achieve heat-activatable thrombin inhibition. Linker substitutions are possible since residues GEGTPNPESHNN (SEQ ID NO: 30) in mini-hirudin 2 can be replaced by the GEGT(GS)$_4$ (SEQ ID NO: 6), (GS)$_6$ (SEQ ID NO: 31) and GEGT(GS)$_6$ (SEQ ID NO: 32) sequences as in peptides MH2-GS, MH2-allGS and MH2-longGS, respectively (Table 1). MH2-GS with the GEGT(GS)$_4$ (SEQ ID NO: 6) linker is used as a comparative control. The MH2 peptides were produced either by standard Fmoc chemistry and/or using an *E. coli* peptide expression system in the case of MH2-GS, MH2-wZIP4 and MH2-wZIP5 and MH2-wZIP6 (Osborne, 2003; Tolkatchev 2010). The peptides were purified by reversed-phase HPLC and their identity was confirmed by mass-spectroscopy and NMR spectroscopy. These MH2 peptides are shown in Table 1.

TABLE 1

Amino Acid Sequences of Bivalent Thrombin Inhibitors

| Name | Linker | Sequence |
|---|---|---|
| BTI1 | (GS)$_8$ | Bbs-Arg-(D-Pip)-GSGSGSGSGSGSGSGS-GDFEEIPEEYLQ (SEQ ID NO: 9) |
| BTI2 | gb1 | Bbs-Arg-(D-Pip)-GEWTYDDATKTFTVTE-GDFEEIPEEYLQ (SEQ ID NO: 10) |
| BTI3 | trpzip6 | Bbs-Arg-(D-Pip)-GEWTWDDATKTWTVTE-GDFEEIPEEYLQ (SEQ ID NO: 11) |
| BTI4 | trpzip5 | Bbs-Arg-(D-Pip)-GEWTYDDATKTFTWTE-GDFEEIPEEYLQ (SEQ ID NO: 12) |
| BTI5 | trpzip4 | Bbs-Arg-(D-Pip)-GEWTWDDATKTWTWTE-GDFEEIPEEYLQ (SEQ ID NO: 13) |
| MH1 | HV1(42-53) | VRFTD-GEGTPKPQSHDN-GDFEEIPEEYLQ (IC$_{50}$ ~ 33 nM) (SEQ ID NO: 33) |
| MH2 | HV2(42-53) | IRFTD-GEGTPNPESHNN-GDFEEIPEEYLQ (IC$_{50}$ ~ 14 nM) (SEQ ID NO: 34) |
| MH2-GS | GEGT(GS)$_4$ | IRFTD-GEGTGSGSGSGS-GDFEEIPEEYLQ (SEQ ID NO: 14) |
| MH2-allGS | (GS)$_6$ | IRFTD-GSGSGSGSGSGS-GDFEEIPEEYLQ (SEQ ID NO: 35) |
| MH2-longGS | GEGT(GS)$_6$ | IRFTD-GEGTGSGSGSGSGSGS-GDFEEIPEEYLQ (SEQ ID NO: 36) |
| MH2-gb1 | gb1 | IRFTD-GEWTYDDATKTFTVTE-GDFEEIPEEYLQ (SEQ ID NO: 15) |
| MH2-wZIP6 | trpzip6 | IRFTD-GEWTWDDATKTWTVTE-GDFEEIPEEYLQ (SEQ ID NO: 16) |
| MH2-wZIP5 | trpzip5 | IRFTD-GEWTYDDATKTFTWTE-GDFEEIPEEYLQ (SEQ ID NO: 17) |
| MH2-wZIP4 | trpzip4 | IRFTD-GEWTWDDATKTWTWTE-GDFEEIPEEYLQ (SEQ ID NO: 18) |

TABLE 2

Inhibitory Activities of Monovalent Binding Moieties for the Active Site of Thrombin

| Peptide | $K_i$, µM |
|---|---|
| Argatroban | 0.0020 ± 0.0002 |
| Dansyl-R-(d-Pip)-NH$_2$ | 0.37 ± 0.04 |
| Dansyl-R-(d-Pip)-Abu-NH$_2$ | 0.82 ± 0.03 |
| Dansyl-R-(d-Tic)-NH$_2$ | 0.86 ± 0.06 |
| Bbs-R-(d-Pip)-NH$_2$ | 1.13 ± 0.03 |
| H-dFPR | 1.57 ± 0.06 |
| Bbs-R-(d-Pip)-G-NH$_2$ | 2.26 ± 0.10 |
| Boc-dFPR | 4.38 ± 0.18 |
| Bbs-R-(d-Pip)-W-NH$_2$ | 6.0 ± 1.0 |
| IRFTDG (SEQ ID NO: 29) | 7 ± 7 |
| Ac-dFPR | 170 ± 18 |

High resolution NMR analysis of BTI2 and BTI5 provided evidence that linkers based on gb1 and trpzip4 sequences exhibit folding behaviors similar to those of the corresponding isolated β-hairpin peptides (FIG. 1). One-dimensional proton NMR spectra and two-dimensional TOCSY and NOESY spectra of BTI2 and BTI5 were recorded in several pH and bulk temperature conditions, including the conditions used in the previously reported NMR studies of gb1 and trpzip4 (Blanco 1994; Cochran 2001). Chemical shifts of the ES1-binding hirudin[54-65] moiety in both inhibitors were essentially the same as those of the isolated hirudin C-terminus (Ni 1990), showing the absence of interactions between the hirudin fragment and the rest of the bivalent molecule. The trpzip4 linker in BTI5 (top panel in FIG. 1) was well folded at three tested bulk temperatures (5° C., 15° C. and 21° C.), and the H$^\alpha$ chemical shifts indicative of a specific backbone conformation were practically identical to those reported previously for the isolated trpzip4 (Cochran 2001). At 5° C., the gb1 linker in BTI2 (bottom panel in FIG. 1) was only folded partially into a β-hairpin with significantly-reduced chemical shift deviations as compared to the trpzip4 linker of BTI5 (top panel in FIG. 1). In addition to such H$^\alpha$ chemical shift characteristics, there were some long-range NOE connectivities between the side chains of residues Trp3/Phe12 and Tyr5/Phe12 confirming some degree of β-hairpin formation at 5° C. for the gb1 moiety of the BTI2 peptide.

The bivalent mode of binding of the BTI and MH2 series of thrombin inhibitors was established using two-dimensional NMR spectroscopy of $^{15}$N-labelled peptides. To enable $^{15}$N-labelling, a variant of the BTI1 peptide referred here to as TWE1 was produced via disulfide-bond linkage between Bbs-Arg-(D-Pip)-Gly-Cys and $^{15}$N-labelled Cys-(GS)$_8$-GDFEEIPEEYLQ (SEQ ID NO: 28). The Bbs-Arg-(D-Pip)-Gly moiety is itself a good inhibitor of human α-thrombin with a K$_i$ of about 2 µM (Table 2). Therefore, the polypeptide linker joining the two binding moieties of TWE1 is Cys-S-S-Cys-(Gly-Ser)$_8$, (SEQ ID NO: 37), which produces a bivalent thrombin inhibitor with a K$_i$ of 2.2±0.4 nM, 100-250 times lower than those for the monovalent fragments, Bbs-Arg-(D-Pip)-Gly-Cys and GDFEE-IPEEYLQ (SEQ ID NO: 8). For NMR studies, the peptide TWE1 contains a uniformly $^{15}$N-labeled portion for Cys-(GS)$_8$-Hir(54-65) (SEQ ID NO: 28) while peptide MH2 is labeled with the $^{15}$N isotope in its entirety.

Figure 2:
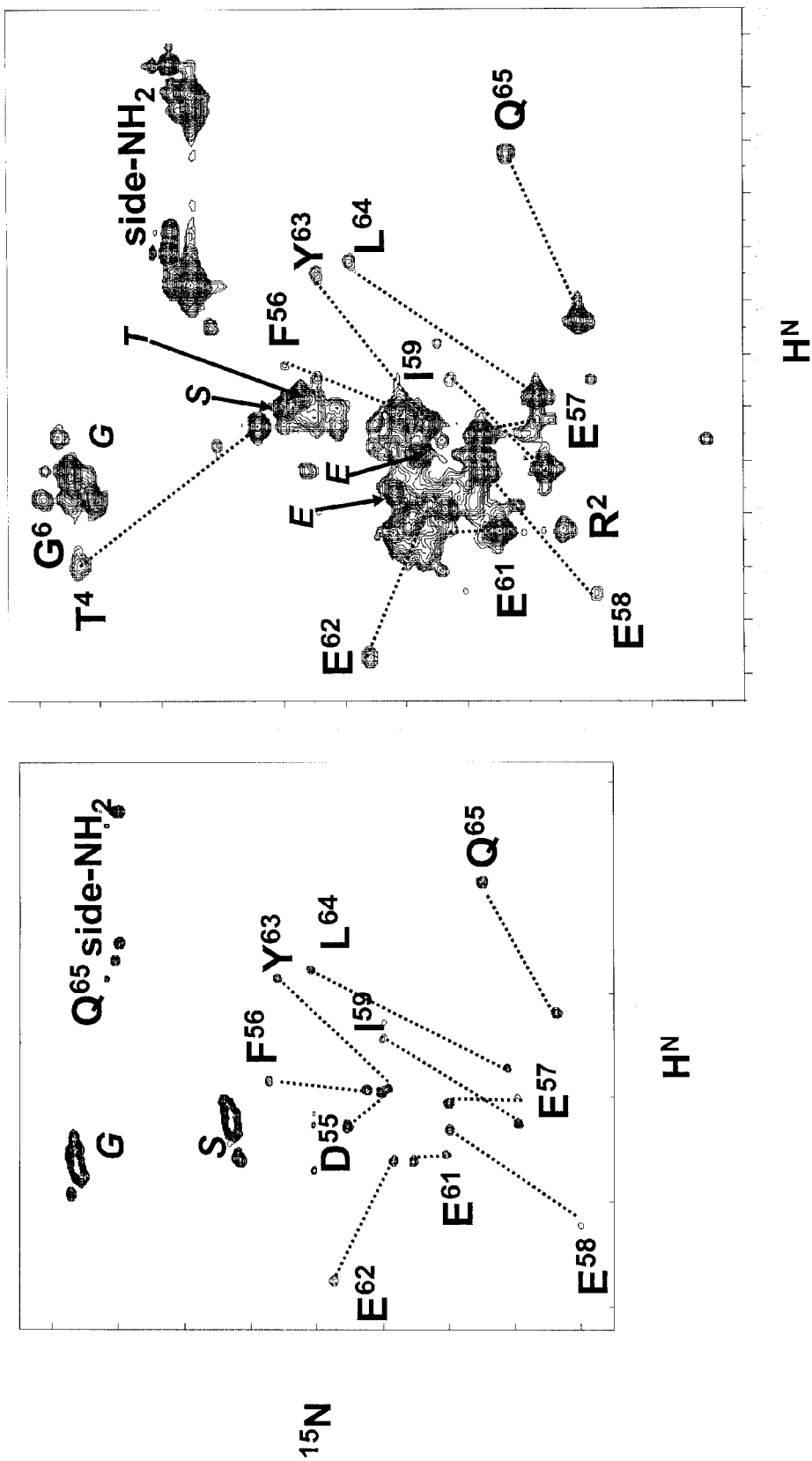
FIG. 2 illustrates the mode of interactions of the BTI and MH2 series of thrombin inhibitors by use of two-dimensional NMR spectroscopy. The compound TWE1 is an analog of BTI1, whereby the linkage between the Bbs-Arg-(D-Pip) moiety and the rest of the peptide is formed instead by a disulfide bond between the Cys residue in Bbs-Arg-(D-Pip)-Gly-Cys and the Cys residue in $^{15}$N-labelled CGSGSGSGSGSGSGSGS-GDFEEIPEEYLQ (SEQ ID NO: 28). The left panel depicts (H,$^{15}$N)-HSQC spectrum of the TWE1-thrombin complex, showing specific interactions of TWE1 with thrombin. The right panel depicts (H,$^{15}$N)-HSQC spectrum of the MH2-thrombin complex, showing bivalent interactions of MH2 with thrombin. The proton and nitrogen frequencies were 800.048 MHz and 81.068 MHz, respectively. Assignments were labeled for each HSQC peak of residues Asp55-Gln65 in the Hir$^{54-55}$ (=GD$_{55}$FEEIP$_{60}$EEYLQ$_{65}$; SEQ ID NO: 8) sequence of the thrombin-bound state and the dashed lines link the free and thrombin-bound peaks for each residue of TWE1 and MH2 with well-resolved crosspeaks.

Human α-thrombin used for NMR experiments was a gift from John W. Fenton, II (Wadsworth Laboratory for Research, New York State Department of Health). [$^1$H,$^{15}$N]-HSQC spectra of TWE1 were collected with a peptide concentration of 211 µM and a thrombin concentration of 155 µM, and of MH2 at 110 µM with thrombin at 66 µM at 25° C. and pH 5.5. FIG. 2 shows the [$^1$H, $^{15}$N]-HSQC NMR spectra of TWE1 (FIG. 2 left panel) and MH2 (FIG. 2 right panel) under sample conditions whereby the free and thrombin-bound states co-exist and exchange in dynamic equilibrium. Resonances of most amino acid residues in the $^{15}$N-labeled segment were assigned unambiguously for both the free and the thrombin-bound states by a combined analysis of sequential NOE connectivities and the cross peak patterns from the homonuclear TOCSY and NOESY spectra.

Residues Asp55-Ile59 and Glu62-Gln65 of the Hir(54-65) segment exhibit large resonance changes upon binding, to a very similar degree for both peptides, indicating a common mode of interaction with the same site of thrombin. In contrast, the backbone amide resonances of the linker residues in both peptides changed only slightly in the presence of thrombin. For example, all the Gly and Ser residues in the linker region of TWE1 have essentially overlapped NMR signals appearing at the same positions in the free and fully-bound [$^1$H,$^{15}$N]-HSQC spectra (FIG. 2 left panel). This shows the lack of conformational changes for these residues between the free and the thrombin-bound states and that there is no significant interaction of the linker residues of TWE1 with thrombin. Generally high-resolution NMR spectra for the thrombin-bound TWE1, especially those of residues Phe56-Ile59 and Glu62-Gln65 (FIG. 2 left panel) as well as sharp proton resonances for thrombin (not shown) indicate that this peptide and very possibly the related BTI1 peptide (Table 1) forms preferentially a monomeric heteromolecular complex with thrombin, instead of cross-linked multimers as observed previously for ligand molecules with long flexible linkers. (Mathews 1994; Liu 2005; Ho 2005; Benjamin 2001).

In addition to substantial changes of residues Asp55-Ile59 and Glu62-Gln65 of the Hir(54-65) segment between the free and thrombin-bound states, fully $^{15}$N-labelled MH2 has a well-resolved residue Thr4 in the active site targeting moiety IRFTD, which exhibits one of the largest chemical shift changes when MH2 is bound to thrombin (FIG. 2 right panel). The IRFTD (SEQ ID NO: 7) moiety of MH2 is therefore expected to interact with the active site of thrombin, since hirudin mimetics related to MH2 have been shown to have their IRFTD-like segments bind to thrombin in the non-canonical or reverse orientation as compared to thrombin substrates (Cappiello 1998; Lombardi 1999). Here, Ile1 occupies roughly the S2 subsite, Arg2 binds the S1 pocket and Phe3 the S4 subsite around the catalytic active site of thrombin (Fethiere 1996; Lombardi 1999; Corral-Rodriguez 2010). In contrast, [$^1$H,$^{15}$N]-HSQC crosspeaks of the linker residues of the MH2 peptide, i.e. GEGTPNPESHNN (SEQ ID NO: 30) or 42-53 of hirudin variant 2, do not change their resonance positions significantly upon binding to thrombin (FIG. 2 right panel), which indicates a lack of significant interactions with thrombin for the linker region. These NMR data are in perfect agreement with the lack of functional dependence on the nature of linker sequences observed for related bivalent inhibitors of thrombin (Maraganore 1990; Tolkatchev 2005). Such flexibilities of the linker segments for both TWE1 and MH2 demonstrate that the binding interactions of the BTI and MH2 series of peptides with thrombin are dominated by two individual binding moieties targeting respectively the active site and the fibrinogen-recognition exosite of thrombin, thereby making it possible to modulate the bivalent binding affinities through linker manipulations (Table 1).

Conformational characteristics of the MH2-series of thrombin inhibitors, especially MH2-wZIP4 and MH2-wZIP5, were further characterized in quantitative details by use of $^{15}$N-NMR transverse relaxation (R$_2$) spectroscopy. Therefore, MH2-wZIP4 and MH2-wZIP5 were prepared in uniformly $^{15}$N-labelled forms (i.e. $^{15}$N-MH2-wZIP4 and $^{15}$N-MH2-wZIP5) by replacing the nitrogen source of the culture media with ($^{15}$NH$_4$)$_2$SO$_4$ (Osborne, 2003; Tolkatchev 2010). The purified $^{15}$N-labelled peptide was dissolved in a buffer that was 50 mM in Tris-HCl, 100 mM in NaCl and 0.1% PEG-8000 at pH 7.6 with a concentration of about 200 µM (micromolar). The $^{15}$N-NMR transverse (R$_2$) relaxation rates (Farrow 1999) and the $^{15}$N-R$_2$ dispersion profiles (Tolkatchev 2003) were collected on a Bruker Avance-800 NMR spectrometer using a 5 mm Z-axis gradient triple-resonance RF probe. The $^{15}$N-R$_2$ values were determined from relaxation curves collected with randomly-placed delays of 14.4, 288.0, 28.8, 259.2, 43.2, 230.4, 57.6, 201.6, 72.0, 172.8, 86.4, 144.0, 100.8, 129.6, 115.2, 14.4, 72.0, 144.0, 201.6, and 259.2 ms. The $^{15}$N-R$_2$ dispersion profiles were obtained with a constant CPMG period of 40 ms and variable $^{15}$N-CPMG inter-pulse delays ($\tau_{CPMG}$) of 10, 0.5, 5.0, 0.625, 3.3333, 0.8333, 2.5, 1.0, 2.0, 1.25, 1.6666, and 1.4286 ms.

Looking closely at FIG. 3A, MH2-wZIP4 and MH2-wZIP5 show a striking similarity in the $^{15}$N-R$_2$ relaxation rates for residues in the entire C-terminal region, i.e. G$_{22}$DFEEI$_{27}$PEEYL$_{32}$Q (SEQ ID NO: 8). Such reduced rates of $^{15}$N-R$_2$ relaxation signify conformational flexibility for these residues as established previously for thrombin-binding peptides encompassing this sequence (Ni 1992). In contrast, most residues of MH2-wZIP4 in the N-terminal region exhibit larger rates of $^{15}$N-NMR relaxation, showing conformational heterogeneity, in other words, linker unfolding or opening, even at the experimental temperature of 290 K. Linker opening is more evident in MH2-wZIP5, which by design has as linker the trpzip5 sequence with a greatly-reduced hairpin stability (Cochran 2001). As a result, most linker residues in MH2-wZIP5 are not even observable, especially at the lower temperature of 277 K, in the (H,$^{15}$N)-HSQC spectra of $^{15}$N-MH2-wZIP5. The increased linker unfolding in MH2-wZIP5 is also reflected by decreased $^{15}$N-R$_2$ values of the sidechain NH signals of the two Trp residues in MH2-wZIP5, which indicate greater mobility of these Trp side chains in a largely unstructured linker region.

Figure 3B:
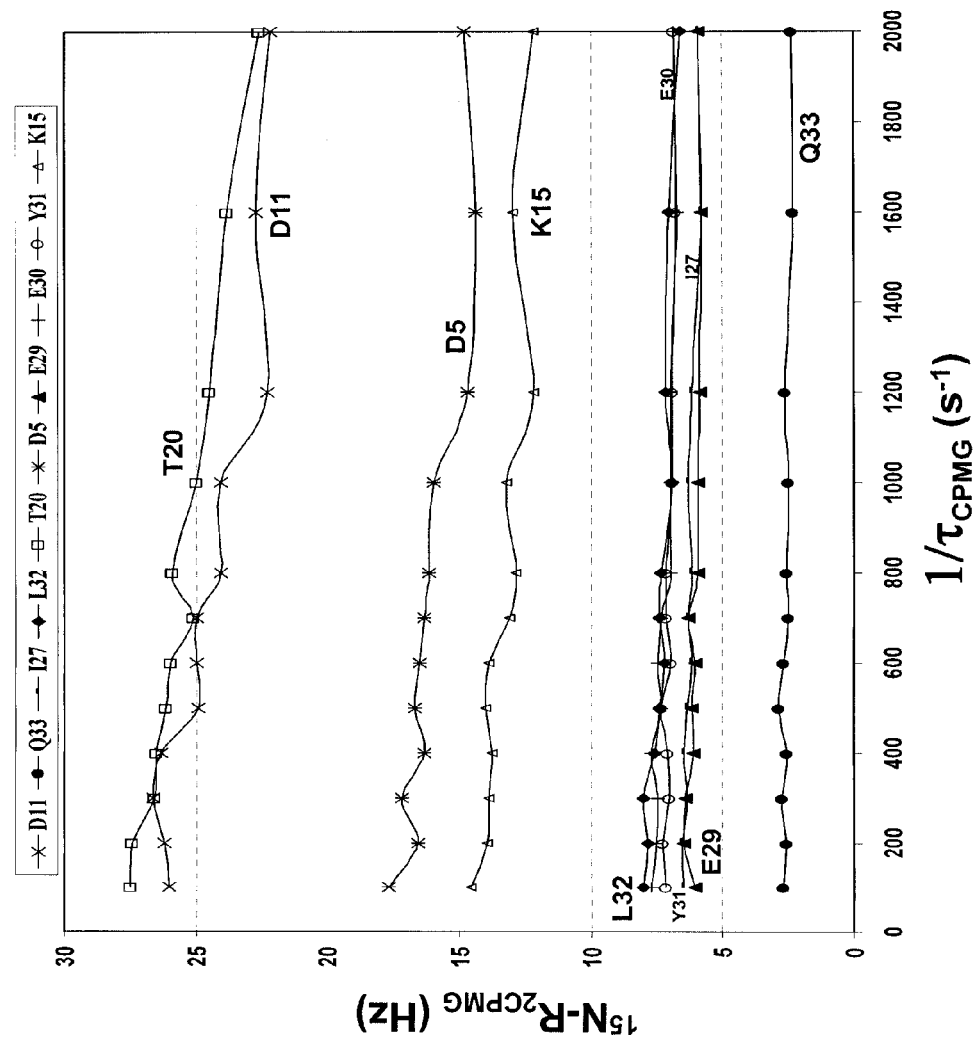
FIG. 3B shows $^{15}$N-NMR transverse ($R_2$) relaxation dispersion curves (Tolkatchev 2003) collected for a sample of $^{15}$N-MH2-wZIP4 under the same experimental conditions as used for $^{15}$N-$R_2$ measurements.
Figure 4A:
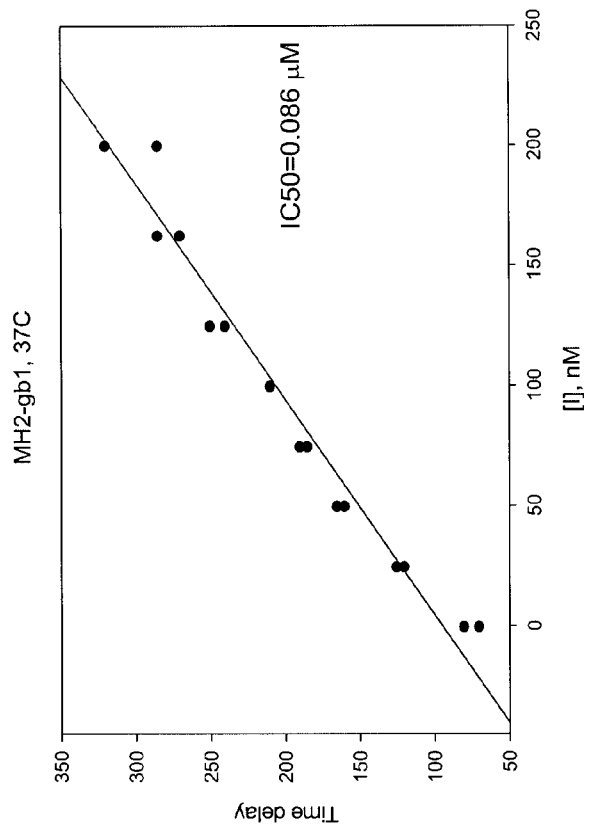
FIG. 4 illustrates the temperature dependence of the thrombin inhibitory activities of the MH2 series of bivalent peptides by use of the fibrinogen clotting assay. (4A) MH2-gb1; (4B) MH2-wZIP6; (4C) MH2-wZIP5 and (4D) MH2-wZIP4. Data collected at 25° C. are shown by the left panels of FIGS. 4A, 4B, 4C and 4D while those of 37° C. are shown by the right panels.
Figure 4A:
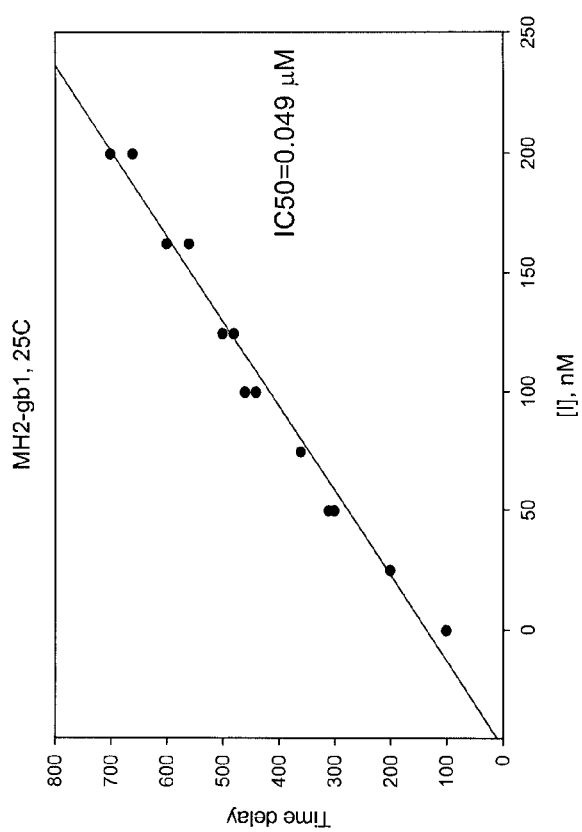
Figure 4B:
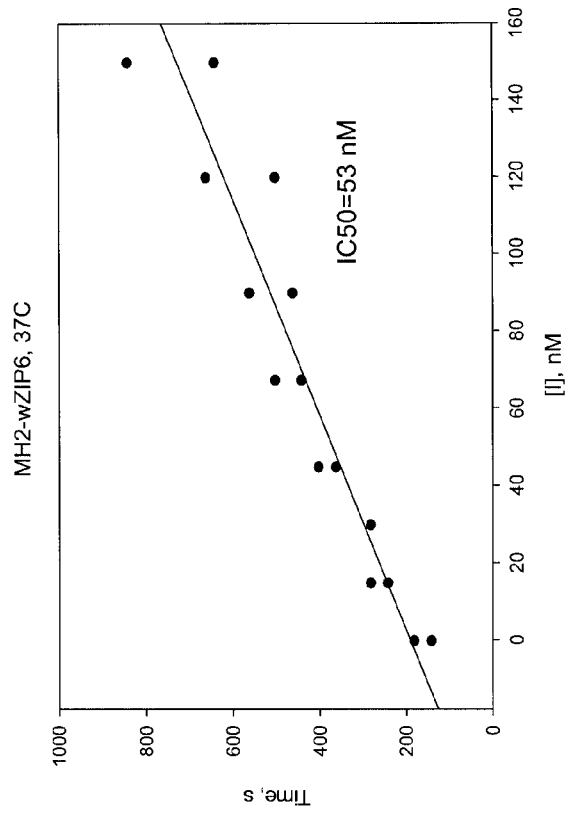
Figure 4B:
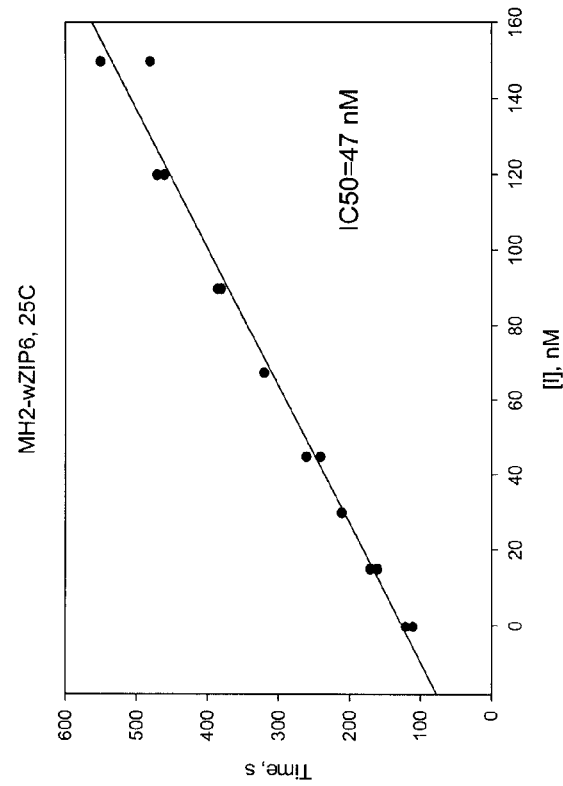
Figure 4C:
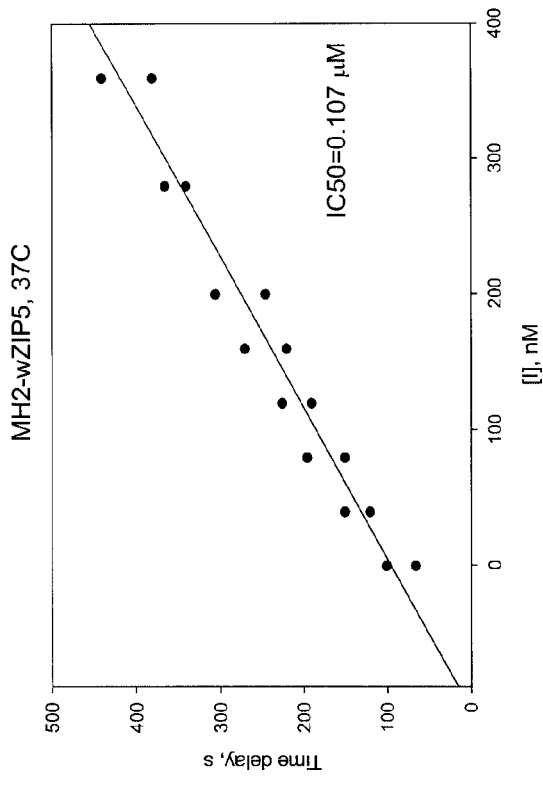
Figure 4C:
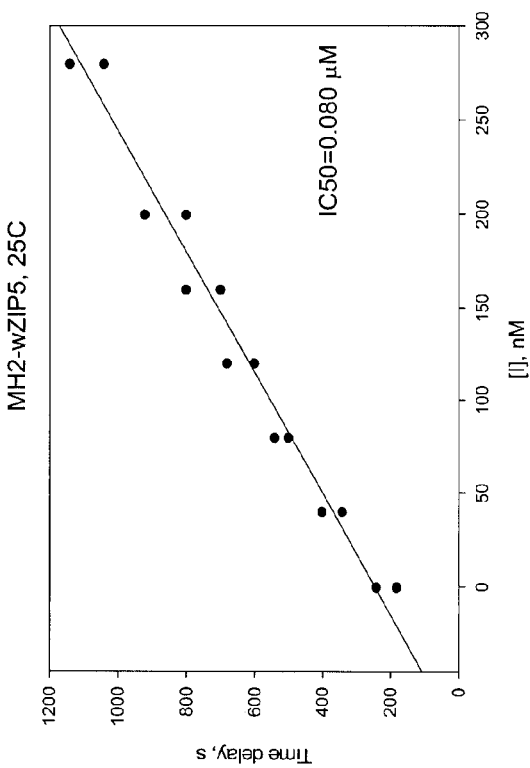
Figure 4D:
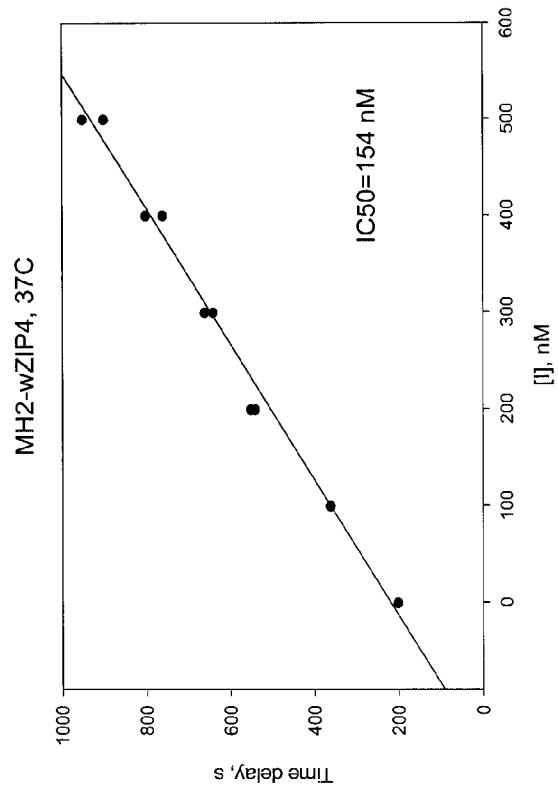
Figure 4D:
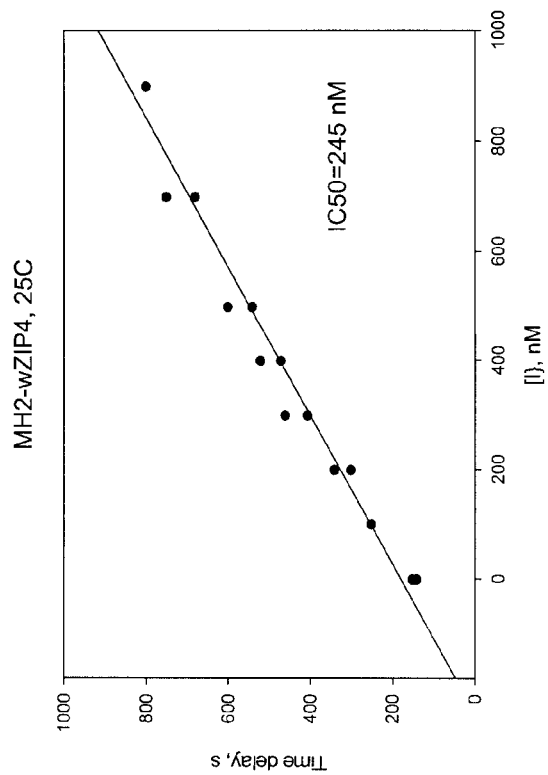

FIG. 3B shows in quantitative details the conformational dynamics of $^{15}$N-MH2-wZIP4 via $^{15}$N-NMR transverse relaxation dispersion spectroscopy (Tolkatchev 2003; Korshnev 2008). Essentially no residues in the C-terminal region, i.e. D$_{23}$FEEI$_{27}$PEEYL$_{32}$Q (amino acids 23-33 of SEQ ID NO:18) exhibit dependence on the strength of the spin-lock field, i.e. as measured by $1/\tau_{CPMG}$, as a result of the lack of a predominant three dimensional structure (Korzhnev 2008). In contrast, most residues in the trpzip4 linker region have large $^{15}$N-R2 values (FIG. 3B) and respond to the increase of the spin-lock field, as exemplified by residues Asp11, Lys15 and hr20. In all, $^{15}$N-NMR relaxation data demonstrate the dynamic character of bivalent thrombin inhibitors containing hairpin linkers, in that the well-structured linker conformation leading to reduced bivalent binding is in dynamic equilibrium with fully-active molecular species containing unfolded linker conformations (see Example 3).

Example 2: Recombinant Production of Bivalent Peptide Inhibitors of Thrombin and $^{15}$N-Labelled Peptides Expression of Fusion Proteins:

One colony of *E. coli* cells harboring recombinant expression plasmids of the C-terminal portion of the TWE1 peptide and the MH2 series of thrombin inhibitors was picked from a fresh agar LB medium plate and grown normally for 6 hrs at 37° C. under rotary agitation (at 250 rpm) in LB medium containing 0.1 mg/ml ampicillin. Day-time culture was diluted to 100 ml of the same medium and grown for 16 hrs under same stirring conditions. It was then diluted to 1 L of the same medium and grown under same conditions until OD$_{600}$=0.65. Expression of fusion protein carrying the peptides was induced by inclusion of 1 mM (final concentration) IPTG (isopropyl β-D-1-thiogalactopyranoside) and continuing the cultures for 16-24 hrs under the same conditions. Cells were collected by centrifugation at 5000 g for 20 min at 4° C.

Purification of Fusion Proteins:

Cell lysis: To lyse the cells, cell pellets were dispersed in 40 ml (1 L culture) of 50 mM Na$_2$HPO$_4$ pH 7.4 and lysed by sonication for 5 minutes, using "burst/cooling" cycles of 15 sec at 20% intensity on ice. Soluble materials were removed by centrifugation at 8000 g for 15 minutes at 4° C. and the supernatant discarded. Pellets were dispersed in 40 ml of 4 M urea in 50 mM Na$_2$HPO$_4$ pH 7.4 and gently rocked for 20 minutes at room temperature followed by centrifugation at 100,000 g for 20 minutes at 4° C. Supernatant was collected and placed on ice.

IMAC: Ni-NTA resin was equilibrated with 4 M urea in 50 mM Na$_2$HPO$_4$ pH 7.4 before application of the collected final supernatant. The resin solution was incubated in-bulk for 1 hr at room temperature under gentle rocking. The resin was washed with 5 batch volumes of 50 mM Na$_2$HPO$_4$ pH 6.8 and the bound protein eluted with 1×0.5 ml of 4 M urea in 0.1 N HCl followed by 3×3 batch volumes of 4 M urea in 0.1 N HCl with each volume collected in a separate tube. The protein content was determined by separation on SDS-PAGE (15% acrylamide-bisccrylamide) followed by measurement of OD$_{280}$ using the elution buffer as a blank.

In the case of the Cys-containing fusion proteins, purified fusing proteins were treated for 3 hours at room temperature with 10 mM tris(2-carboxyethyl)phosphine hydrochloride (TCEP) in a buffer of 100 mM sodium phosphate and 6 M urea at pH 4.5. The solutions were loaded onto SepPAK-C8 columns (12 cc) pre-equilibrated with 0.1% TFA. Fractions eluted with 40 to 60% (v/v) acetonitrile/water in 0.1% TFA were pooled and lyophilized. The fusion protein carrying the cysteine-containing peptide was first conjugated with the synthetic fragment Bbs-Arg-dPip-Gly-Cys through disulfide formation. To five micromoles of Bbs-Arg-dPip-Gly-Cys in 300 μL DMF and 1.7 mL MES buffer (pH 5.4), 100 μL of 40 mM 2,2'-dithiodipyridine (Sigma) in DMF was added dropwise and incubated for 3 hours at room temperature. The product Bbs-Arg-dPip-Gly-Cys-SS-thiopyridine was purified by HPLC, and mixed with 1.3 equivalents of the fusion proteins in 36% acetonitrile/64% (v/v) 25 mM MES buffer, pH 5.0, 5.5 M urea. The pH was raised to 6.5 with a buffer of 100 mM HEPES (pH 7.5) and the reaction mixture was incubated at room temperature for 2 hours. Release of the disulfide-conjugated peptide (i.e. TWE1) from the fusion protein was performed through CNBr cleavage at a single Met residue following the His-tag sequence (Tolkatchev 2010) after an overnight incubation at room temperature with 300 equivalents of CNBr. The carrier protein was separated from the released peptide TWE1 using Ni$^{2+}$-NTA agarose resin (Qiagen). TWE1 was fractionated on 12 cc SepPAK-C18 columns, and finally purified by use of HPLC with an overall yield of 12%.

Peptide Generation:

CNBr cleavage and removal: Fusion protein was diluted to 5 mg/ml with 4 M urea in 0.1 N HCl. CNBr was added at a 1:4 ratio (w:w for protein:CNBr) and mixed thoroughly. Cleavage proceeded for 40 hrs, at room temperature in the dark.

Removal of the CNBr: A dialysis chamber (Slide-a-Lyser™ 2000 MWCO) was rehydrated for 10 min and filled according to manufacturer's instructions with the protein/CNBr mixture using a 21 g needle. Dialysis was made against 100 V of 4 M urea in 0.1 N HCl for 2 hrs at room temperature with gentle stirring. The buffer was changed after 2 hrs and dialysis continued under the same conditions for 2 hrs. A third buffer change was made and dialysis continued for 18 hrs under the same conditions. Dialysate was collected according to manufacturer's instructions.

Reverse-phase HPLC: Recovered material following cleavage is a mixture of the uncleaved protein, the carrier protein and the peptide. Reverse-phase HPLC is used to separate peptides of interest from the other components. Using a Waters 600 flow controller and a Waters 2487 Absorbance Detector set at $\lambda_{278}$ and a Vydac™ 218 TP1010 C18 column equilibrated with 25% acetonitrile and 0.1% TFA in $H_2O$, the sample was applied and protein mixture subjected to a linear gradient of 25-45% acetonitrile/0.1% TFA/$H_2O$ at 1%/min, 5 ml/min. The peaks of interest were collected and samples taken aside for mass spectroscopy. Collected material was frozen on dry ice for 30 min and lyophilized. Dry material was stored at room temperature.

Example 3: Bulk Temperature Dependence of the Thrombin Inhibitory Activities

The three-dimensional NMR structure of a fully-folded and well-structured β-hairpin specifies an end-to-end distance $C^\alpha(Gly^{41})$-$C^\alpha(Glu^{56})$ for trpzip4 as approximately 4.3 Å (Cochran 2001), which cannot span the approximately 15-16 Å separating the active site (the P1'-P2' site more specifically) and fibrinogen-recognition exosite, as shown in the X-ray structures of thrombin in complex with the substrate-like bivalent thrombin inhibitors P628 and P798 (Slon-Usakiewicz 2000). Therefore, fully-structured trpzip peptides can not satisfy the geometric requirements for bivalent binding. If weaker monovalent modes of binding are neglected (DiMaio 1990; Slon-Usakiewicz 2000), interactions between thrombin (IIa) and the trpzip-containing bivalent inhibitors can be represented as follows:

"closed"+$IIa^{free}$ ↔ "open"+$IIa^{free}$ ↔ BTI*IIa where "closed" corresponds to binding-incompetent species of the free BTI peptide, "open" corresponds to binding-competent species of the free BTI peptide, $IIa^{free}$ is free thrombin and BTI*IIa is the inhibited and catalytically inactive BTI-thrombin complex. Closed trpzip linkers decrease the actual concentration of binding-competent species thus increasing the observed inhibition constant:

$K_D$=[open][$IIa^{free}$]/[BTI*IIa];

$K_i$=([closed]+[open])[$IIa^{free}$]/[BTI*IIa]=$K_D/p_{open}$;

where $K_D$ is the dissociation constant of open species, $K_i$ is the observed inhibition constant, and $p_{open}$ is the population of open species [open]/([closed]+[open]).

Human α-thrombin was purchased from Haemotologic Technologies, Inc., VT, USA. Inhibition constants $K_i$ (Table 3) were measured in 50 mM Tris-HCl, 100 mM NaCl, 0.1% polyethylene glycol (PEG)-8000 at pH 7.6 by following thrombin-catalyzed hydrolysis of the chromogenic substrate S-2366 (Chromogenix) at 21° C. and 37° C. in the presence of varying concentrations of inhibitors (DiMaio 1990). Peptide concentrations were determined by comparing the OD values of peptide stock solutions with the predicted extinction coefficient for each peptide (Gill 1989).

TABLE 3

Inhibition Parameters of Bivalent Thrombin Inhibitors BTI

| | Linker | Linker $T_m$** (° C.) | T, ° C. | $K_i$, nM | $p_{unfold}$ | $K_D$, nM |
|---|---|---|---|---|---|---|
| BTI1 | $(GS)_8$ | | 21 | 0.53 ± 0.03 | 1 | 0.53 ± 0.03 |
| BTI2 | gb1 | ~7 | 21 | 1.10 ± 0.06 | 0.44 | 0.49 ± 0.03 |
| BTI3 | trpzip6 | 45 | 21 | 1.75 ± 0.09 | 0.29 ± 0.09 | 0.50 ± 0.15 |
| BTI4 | trpzip5 | 43 | 21 | 2.7 ± 0.2 | 0.24 ± 0.04 | 0.66 ± 0.11 |
| BTI5 | trpzip4 | 70 | 21 | 12.6 ± 0.7 | 0.050 ± 0.004 | 0.63 ± 0.06 |
| BTI1 | $(GS)_8$ | | 37 | 1.3 ± 0.3 | 1 | 1.3 ± 0.3 |
| BTI2 | gb1 | ~7 | 37 | 4.0 ± 0.2 | 0.69 | 2.8 ± 0.1 |
| BTI3 | trpzip6 | 45 | 37 | 4.6 ± 0.2 | 0.41 ± 0.09 | 1.9 ± 0.4 |
| BTI4 | trpzip5 | 43 | 37 | 6.9 ± 0.5 | 0.41 ± 0.05 | 2.8 ± 0.4 |
| BTI5 | trpzip4 | 70 | 37 | 19.2 ± 0.8 | 0.082 ± 0.006 | 1.6 ± 0.1 |

Every kinetic experiment was performed in duplicates. Kinetic data were processed as described previously (Tolkatchev 2005).
**$T_m$ values for the unfolding of the respective hairpin structure were as reported for the isolated peptides gb1, trpzip6, trpzip5 and trpzip4 (Cochran 2001; Blanco 1994).

The $K_i$ values varied noticeably, and there was a clear correlation between the activity of inhibitors and the thermal stability of the corresponding linkers. Linkers with a higher bulk temperature of unfolding transition (Cochran 2001; Blanco 1994) produced less potent inhibitors. Each peptide, including BTI1 with a flexible linker of $(GS)_8$, still exhibited a slight decrease in its inhibitory activity (or increase in $K_i$) with an increase of (bulk) temperature from 21° C. to 37° C. But it is clear that the more than two fold reduction in activity seen with BTI1 is partially compensated by a linker that can unfold (or open), since BTI5 (with the well-folded trpzip4 linker) showed a roughly similar activity for thrombin inhibition between 21° C. and 37° C. It is also seen that the best-structured trpzip4 linker cannot completely abolish the bivalent inhibitory activity at a temperature well below (i.e. 21° C.) the denaturation temperature ($T_m$ is about 70° C.) determined for the trpzip4 peptide (Cochran, 2001). This phenomenon is a direct consequence of the limited conformational stability of the hairpin linker within the bivalent peptides, as demonstrated for the MH2-series of bivalent thrombin inhibitors (FIG. 3).

Assuming a two-state unfolding of the trpzip linkers, the unfolded populations $p_{unfold}=p_{open}$ (Table 3) can be calculated using reported thermal characteristics of isolated trpzip peptides (Cochran 2001). It is important (Cochran 2001) to take into consideration bulk temperature dependences of the enthalpy and entropy differences between folded and unfolded states of trpzip peptides (Privalov 1997). Disregard for the appreciable ΔCp difference between folded and unfolded species would lead to particularly large underestimation of $p_{unfold}$ for BTI5, since the bulk temperatures used for $K_i$ determination were far from the trpzip4 folding transition point.

The $p_{unfold}$ value for the BTI2 inhibitor was calculated using ΔH=11.6 kcal/mol and ΔS=39 cal/mol/K obtained in earlier studies of the gb1 peptide (Munoz 1997), which gives $p_{unfold}$ values of 0.44 and 0.69 at 21° C. and 37° C., respectively. On the other hand, the gb1 peptide was suggested to contain a higher population of unfolded species (estimated 0.7 and 0.85 at 21° C. and 37° C., respectively) if non-zero ΔCp between folded and unfolded gb1 states is taken into account (Cochran 2001). Derived $K_D$ values demonstrate that at each bulk temperature, variation in $K_D$ for BTI2-BTI5 is significantly smaller than that in $K_i$, particularly at 21° C. (Table 3). More importantly, all the $K_D$ values are close to those of BTI1 which contains a flexible (or random-coil) $(GS)_8$ linker, which confirms the predicted small variation in $K_D$ values for bivalent ligands connected by flexible linkers of equal contour length and similar composition (Zhou 2001a; Zhou, 2001b). These results indicate that energetics of linker folding (or hairpin formation) contributes significantly to the lower inhibitory activity (increase in $K_i$) for BTI5 containing the well-structured trpzip4 sequence.

The same enzyme kinetic assays were used to determine the inhibitory activities of MH2 and two MH2-derived peptides, MH2-allGS and MH2-GS (Table 4). Clotting assays were carried out to determine the inhibitory activities of the rest of the MH2 peptides by use of the protocols described previously (DiMaio 1990; Taka 2000; Su 2004). The assay employs bovine plasma fibrinogen dissolved at 0.1% in 50 mM Tris-Cl, 100 mM NaCl, 0.1% PEG-8000 at pH 7.6 (i.e. the clotting buffer). In addition to the use of optical densities or ODs (Gill 1989), concentrations of the peptide stock solutions were ranked (and corrected when necessary) by use of quantitative proton NMR spectroscopy (Cavaluzzi 2002). Each assay mixture contained a certain concentration of the peptide, and the reaction was started by the addition of human thrombin to a final concentration of approximately 0.5 nM. Optical absorbance of the assay mixtures was measured at 420 nm using the Spectramax™ plate reader. The onset clotting time was determined as an intersection of the baseline and the tangent line at point of inflection of the clotting curve. The concentration of an MH2 peptide needed to double the clotting time was defined as $IC_{50}$ (DiMaio 1990) as illustrated in FIG. 4 and summarized in Table 4. The correlation between $IC_{50}$ values and linker unfolding is similar to that for the BTI series of inhibitors (Table 3). Again, the well-structured linker trpzip4 does not completely repress the thrombin-inhibitory activity of the bivalent peptide MH2-wZIP4 (Table 4), as similarly observed for the BTI5 peptide (Table 3). Compared to a control inhibitor containing a flexible linker, e.g. MH2-GS, MH2-wZIP4 reduces the bivalent inhibitory activity, i.e. from a $K_i$ of 27 nM for MH2-GS at 25 C to an $IC_{50}$ of ~250 nM at the same temperature for MH2-wZIP4 (Table 4). Unfolding of the trpzip4 linker now leads to somewhat increased inhibitory activity or an apparent decrease of the $IC_{50}$ value of MH2-wZIP4 instead of the essentially constant $K_i$ values observed for BTI5 between 21° C. and 37° C. (Table 3).

TABLE 4

Anti-Clotting Activities of the MH2 Series of Thrombin Inhibitors

| Name | Linker | $IC_{50}$ (nM, T = 25° C.) | $IC_{50}$ (nM, T = 37° C.) | $IC_{50}$ (nM, T = 42° C.) |
|---|---|---|---|---|
| MH2 | GEGTPNPESHNN (SEQ ID NO: 30) | 34 ($K_i$)** | 67 ($K_i$)** | |
| MH2-allGS | $(GS)_6$ (SEQ ID NO: 31) | 30 ($K_i$)** | 50 ($K_i$)** | |
| MH2-GS | $GEGT(GS)_4$ (SEQ ID NO: 6) | 27 ($K_i$)** | 59 ($K_i$)** | |
| MH2-gb1 | gb1 | 49 | 86 | — |
| MH2-wZIP6 | trpzip6 | 47 | 53 | — |
| MH2-wZIP5 | trpzip5 | 80 | 107 | — |
| MH2-wZIP4 | trpzip4 | 245 | 154 | 148 |

Every inhibition assay was performed in duplicate (see FIG. 4). **These values for MH2. MH2-allGS and MH2-GS were determined as the inhibition constants ($K_i$) by following the thrombin-catalyzed hydrolysis of the chromogenic substrate S-2366, as performed for the BTI1-BTI5 peptides (Table 3).

Taken together, the data in Tables 3 and 4 confirm that the bivalent thrombin inhibitors of the present invention are sensitive to and activatable by bulk temperature elevation in terms of their inhibitory activities toward thrombin.

Example 4: Linker Folding/Unfolding (or Opening/Closing) in a Bivalent Thrombin Inhibitor Followed by Use of NMR Spectroscopy Peptide MH2-wZIP4 (Table 1) was examined in further detail to determine the degree of linker unfolding (opening) associated with the apparently increased inhibitory activity observed with (bulk) temperature elevations (Table 4). At 277 K, the linker region of MH2-wZIP4 assumes a better defined three-dimensional (3D) structure or is essentially closed, as shown by the significantly downfield shifted amide NH crosspeaks of residues Thr9 and Thr18 (FIG. 5A, numbered here as they appear in peptide MH2-wZIP4), the upfield shifted amide NH crosspeaks of Glu7, Thr14 and Thr16 and the downfield shifted amide NH crosspeaks of Trp10 and Trp19 characteristics of a β-hairpin structure (Cochran, 2001). With the bulk temperature increased to 298 K and progressively to 318 K, the amide NH crosspeaks of Glu7, Thr9, Trp10, Thr14, Thr16, Thr18 and Trp19 all experience significant exchange-mediated line broadening, while the side-chain NH crosspeaks of Trp8. Trp10, Trp17 and Trp19 all shift to the right, indicating gradual unfolding or opening of the β-hairpin structure. As compared to the lower temperature (i.e. 277 K), the incomplete structuring of the trpzip4 motif within MH2-wZIP4 at ambient (298 K) and higher temperatures is clearly related to the residual thrombin-inhibitory activities observed for both MH2- wZIP4 and the related BTI5 peptide (Table 3 and 4). Higher bulk temperatures, i.e. 318 K and 328 K, unfold completely the β-hairpin structure, as all the upfield- and downfield-shifted amide NH crosspeaks disappear and merge into the NH resonance envelope in between 7.7 and 8.7 ppm (FIG. 5A), as shown for the unfolding of the trpzip4 peptide (Cochran 2001). In contrast, lineshapes of the HSQC crosspeaks of the DFEEIPEEYLQ (SEQ ID NO: 39) segment of $^{15}$N-MH2-wZIP4 remain sharp and relatively insensitive to temperature changes, showing the lack of a pre-dominant three-dimensional structure for this thrombin-binding sequence. Such temperature dependence of the NMR HSQC peaks of $^{15}$N-MH2-wZIP4 mirrors the characteristics of the $^{15}$N-NMR transverse relaxation rates ($R_2$) (FIG. 3 and Example 1), in that the (closed) structure of the linker region (i.e. trpzip4) has a limited conformational stability even at ambient temperatures (290 K or 298 K), well below its denaturation temperature $T_m$ (Table 3).

Figure 5A:
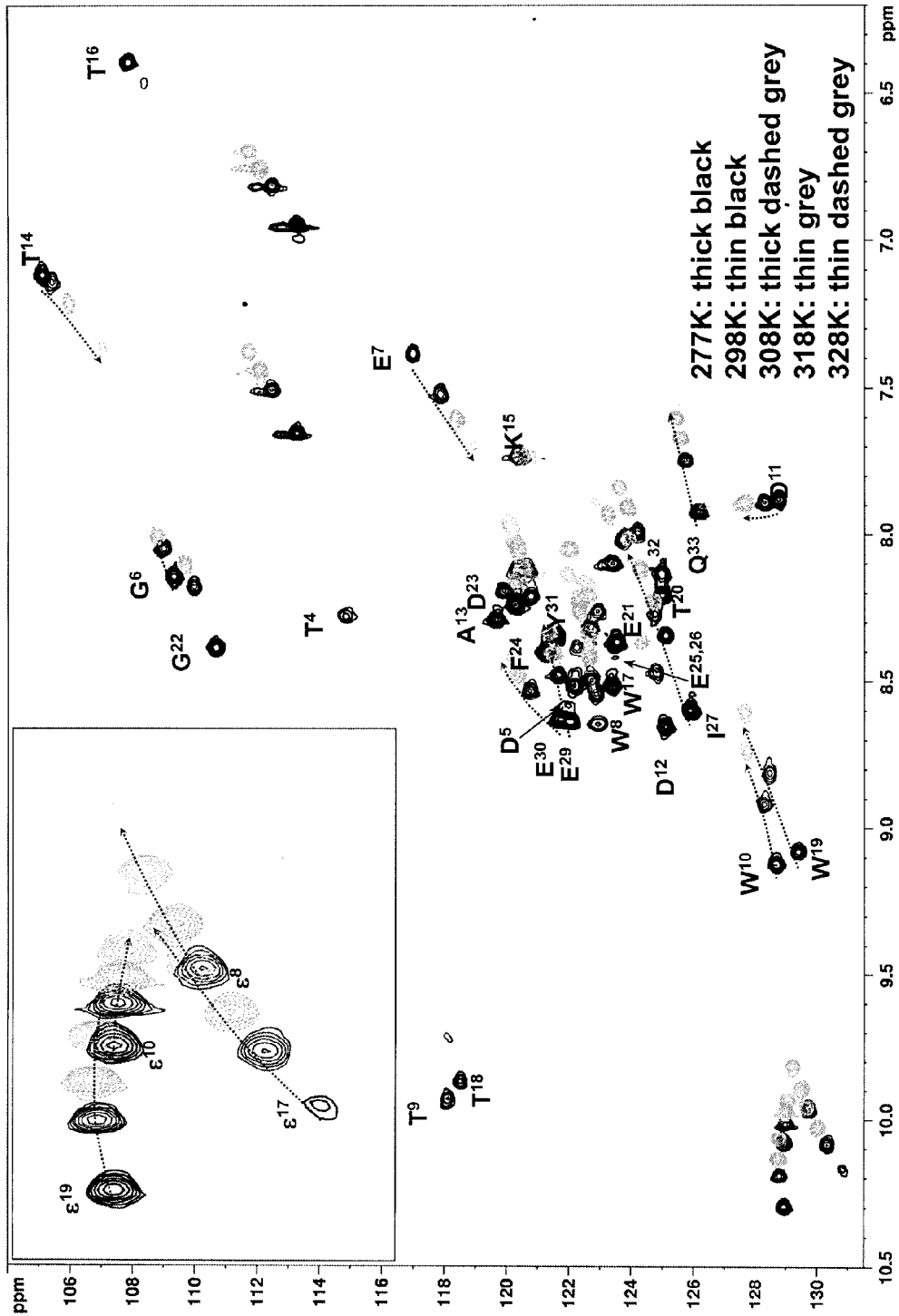
In FIG. 5A, the HSQC spectra at 277 K (5° C.) are plotted as thick and black contours. Spectra at increased (bulk) temperatures are shown by thin and black contours for 298 K (25° C.), thick and dashed gray contours for 308 K (35° C.), thin gray contours for 318 K (45° C.), thin dashed gray contours for 328 K (55° C.).
Figure 5B:
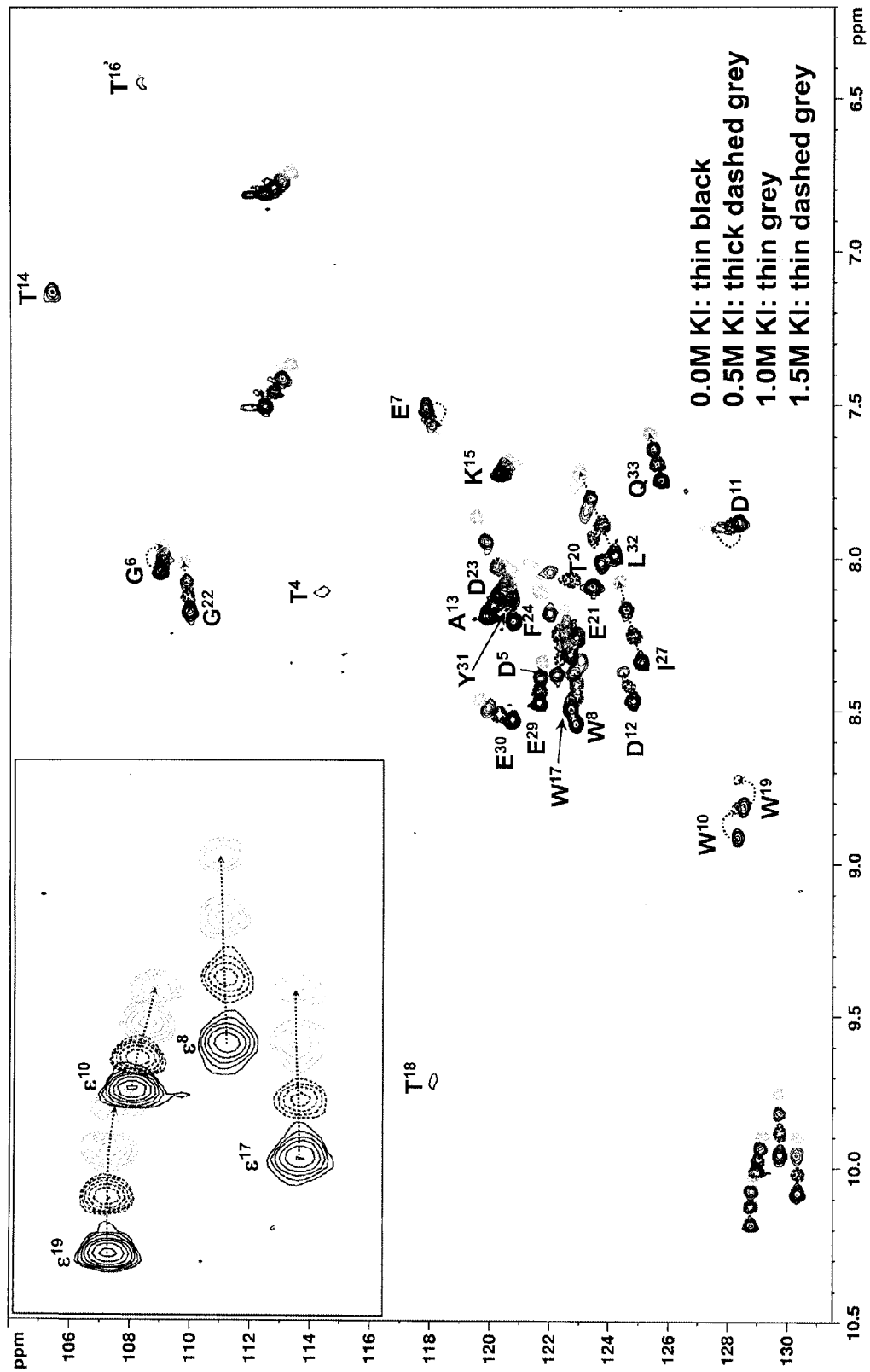
FIG. 5B illustrates the effects of adding potassium iodide (KI) starting with the HSQC spectra of $^{15}$N-MH2-wZIP4 at 298 K (25° C.) (thick dashed contours). The first increment of KI was 0.5 M, shown by thin black contours, which is followed by 1 M of KI (thin gray contours) and 1.5 M of KI (thin dashed gray contours). $\varepsilon^8$, $\varepsilon^{10}$, $\varepsilon^{17}$ and $\varepsilon^{19}$ label the side-chain NH peaks of Trp8, Trp10, Trp17 and Trp19, respectively (following the numbering system in MH2-wZIP4). Other amide NH crosspeaks are also labelled by the corresponding residues as they appear in the sequence of MH2-wZIP4. Dotted arrows trace the peak shifts of the respective residues in response to temperature increases and to the increase of KI concentration.

FIG. 5B illustrates the effects of adding potassium iodide (KI) on the conformational stability of the β-hairpin linker in $^{15}$N-MH2-wZIP4. Therefore, the presence of KI at a concentration of 1 M opens the β-hairpin structure to almost the same extent as a (bulk) temperature elevation of about 15 K, i.e. from 298 K to 323 K. Separate NMR experiments establish that the water proton NMR frequency (PRF) displays a linear dependence on temperature with a coefficient of −9±0.1 Hz/K at an external magnetic field of 800 MHz or −0.011 ppm/K as reported (Lutz 1993; Ishihara 1995; Mallamace 2011). Potassium iodide confers a similar shift on the water proton NMR frequency with a linear coefficient of −140±5 Hz/M at 800 MHz, which is a result of the structure-breaking properties of KI and the creation of hyper-mobile water (Kinoshita 2009; Suzuki 2004; Kabir 2003). In other words, potassium iodide (KI), especially the iodide ion, has a strong destabilizing and denaturing effect on the β-hairpin structure of MH2-wZIP4, as demonstrated with native proteins (Baldwin 1996; Ramos 2002; Sedlak 2008). Other water structure-breaking or "hot" salts (or ions) include high concentrations of NaCl, KCl (Kinoshita 2009; Suzuki 2004), and even HCl (hydrochloric acid) (Li 2006), which can accumulate in inflamed tissues. Using water proton NMR chemical shift frequency recorded at 800 MHz, KCl and NaCl were calibrated to increase the apparent temperature of water (bulk+hyper-mobile water) with a linear coefficient of 7.8 K/M and 7.1 K/M, respectively, as compared to 15.5 K/M determined for potassium iodide (KI). Another apparently "hot" salt is $FeCl_3$, which was shown to have much stronger effects on the hydrogen-bonding network of water than HCl (Li 2006). $FeCl_3$ is used as one of the standard chemical agent for the induction of vascular injury in in-vivo models of thrombosis (Wang 2005; Couture 2011; and Example 11). Application of $FeCl_3$ to blood vessels has been shown to induce major de-structurization of aligned collagen fibrils in vessel walls in addition to inflammatory effects on the cellular components (Eckly 2011).

Example 5: Inhibition of Blood Coagulation

Thromboplastin (Prothrombin Time) and Activated Partial Thromboplastin Time Assays:

Prothrombin (clotting) time (PT) or activated partial thromboplastin (clotting) time (APTT) assays were carried out at certain concentrations of the thrombin inhibitors of the present invention using pooled human plasma with addition of thromboplastin or activated partial thromboplastin to initiate clotting. The assays employed kits from Biopool International (Ventura, Calif., USA) or from Pacific Haemostasis (Middletown, Va., USA) using the procedures supplied by the manufacturer. Briefly, the stock solution of an inhibitor (with the concentration determined using UV-based OD determination, see Gill 1989) is diluted in a buffer of 20 mM HEPES and 150 mM NaCl at pH 7.4 (HBS) to a final volume of 50 µL, to which is added the reconstituted normal plasma (Product #CMS-176172 from Fisher Scientific) in an equal volume. This solution mixture is equilibrated at 37° C. for 2 minutes before 50 µL of the APTT-10XL solution (CMS-022927) is introduced forcibly to ensure proper mixing. This new mixture was incubated at 37° C. for another 5 minutes, which is followed by the addition of 50 µL of 0.02 M $CaCl_3$ (Fisher Scientific CMS-022925) pre-warmed at 37° C. For the prothrombin time (PT) assay, an inhibitor is diluted in HBS to a final volume of 25 µL, to which is added the reconstituted control plasma (Fisher Scientific CMS-176172) in an equal volume. This solution mixture is equilibrated at 37° C. for 5 minutes before addition of 100 µL of the thromboplastin solution (CMS-176099) pre-warmed at 37° C. For APTT assays, inhibitory activities of the peptides are expressed as concentrations needed to achieve 50% of the maximum delay in clotting time ($MCT_{50}$) as compared to the absence of thrombin inhibitors (Maraganore 1989). For PT assays, inhibitory activities are measured as the concentrations of the peptides that prolong the clotting time by 50% ($IC_{50}$) of that of the normal control plasma (Maraganore 1990). PT and APTT assays were also carried out using slightly modified experimental procedures. Thus, 50 µL of a control plasma (Pacific Hemostasis) solution was added to 100 µL HBS (20 mM HEPES and 150 mM NaCl at pH 7.4) containing varied concentrations of the peptides of this invention. After incubation at 37° C. for 5 min, the mixture was added to 50 µL of the thromboplastin or activated partial thromboplastin reagent. Clotting of the plasma was monitored by change in absorbance at 420 nm using a SpectraMax™ plate reader.

Figure 6A:
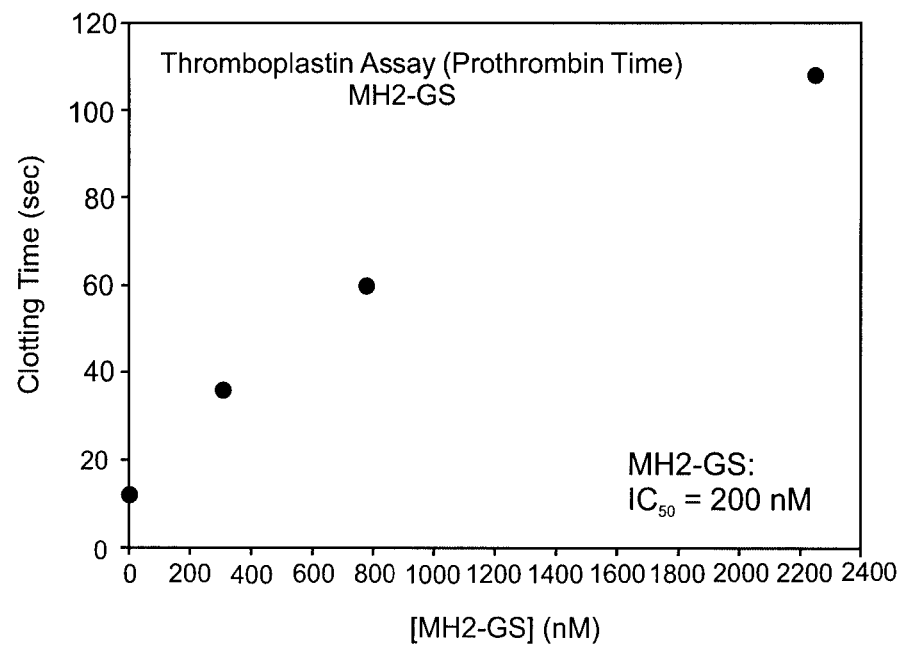
FIG. 6A shows the dose responses of MH2-GS (upper panel) and MH2-wZIP4 (lower panel) in delaying the prothrombin (clotting) times.
Figure 6A:
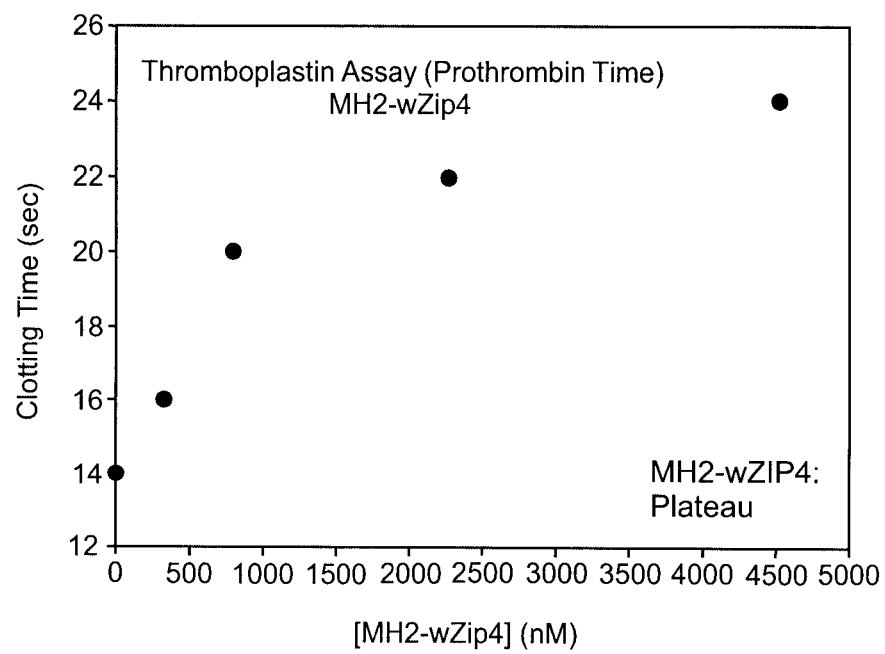
Figure 6B:
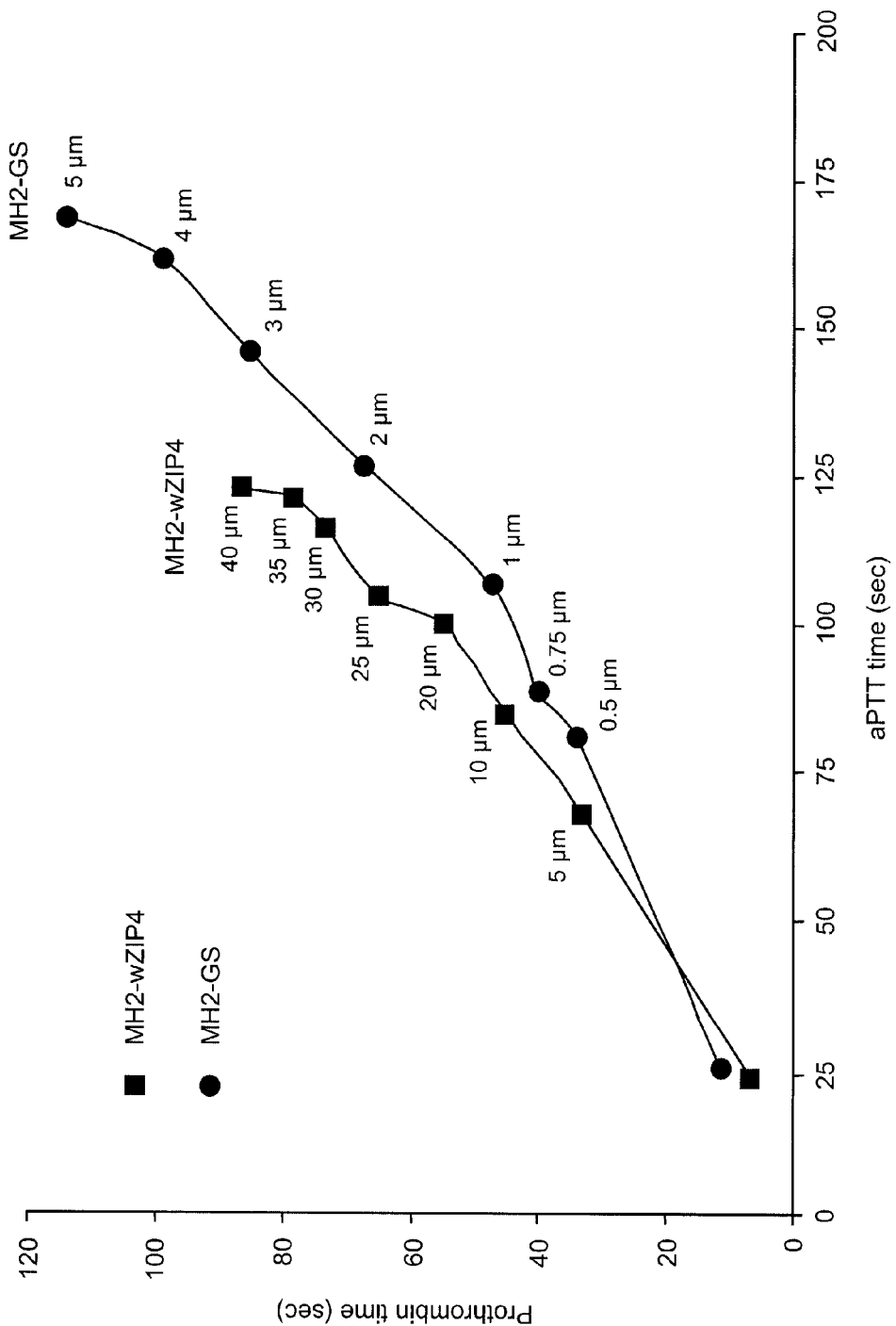
FIG. 6B is the relationship between the prothrombin time (PT) and activated partial thromboplastin time (APTT) (Warkentin 2004) for MH2-GS and MH2-wZIP4 in the specified concentration ranges.

The prothrombin time (PT) and APTT assay results for MH2-GS and MH2-wZIP4 are shown in FIG. 6 and are summarized in Table 5. Table 5 also includes the anti-thrombin and anticoagulant activities of the hirudin-based thrombin inhibitor, bivalirudin/hirulog-1 (Angiomax™), which were determined under the same conditions described above. FIG. 6B further illustrates the unique anticoagulant properties of MH2-wZIP4 as compared to MH2-GS containing the unstructured sequence GEGTGSGSGSGS (SEQ ID NO: 6) as the flexible linker. MH2-GS exhibits a more potent effect in delaying the prothrombin time as compared to APTT, as observed for bivalirudin/hirulog-1 (Warkentin 2004). In contrast, MH2-wZIP4 has a greatly-reduced anticoagulant potency in both the PT and APTT assays, reaching plateau values for the clotting times (FIG. 6A bottom panel and FIG. 6B). In addition, MH2-wZIP4 exhibits a saturable dose response in APTT assays (FIG. 6B) similarly to those observed for anticoagulant peptides derived from the C-terminal tail region of hirudin (Maraganore 1989). On the other hand, MH2-wZIP4 still retains the differential inhibitory effect in PT assays, albeit at much higher concentrations, demonstrating a similar mechanism of action on the blood coagulation cascade in addition to the inhibition of thrombin (Warkentin 2004; Bock 2007). The more active MH2-wZIP5 and MH2-wZIP6 (Table 4) follow essentially the same behavior in their PT-APTT curves (not shown) as that of MH2-GS (FIG. 6B), but requiring concentrations about 2.5 times those used for MH2-GS.

TABLE 5

Activity Profiles of Thrombin Inhibitors
at 37° C. Measured by PT and APTT Assays

| Peptide | $K_I$ (Thrombin Inhibition) | $IC_{50}$ (Prothrombin Time) | $MTC_{50}$ (APTT) |
|---|---|---|---|
| Bivalirudin | 2 n$M^a$ | 93 nM | ND*** |
| MH2-GS | 60 n$M^b$ | 200 nM | 0.9 μM |
| MH2-wZIP4 | 154 n$M^c$ | 1 μM (Plateau at >900 nM) | 8 μM |
| MH2-wZIP5 | 107 n$M^c$ | <300 nM | 2 μM |
| MH2-wZIP6 | 53 n$M^c$ | <400 nM | 3 μM |

[a] Determined by following thrombin-catalyzed hydrolysis of the chromogenic substrate S-2238.
[b] Determined by following thrombin-catalyzed hydrolysis of the chromogenic substrate S-2366.
[c] $IC_{50}$ values determined by following aggregation of bovine fibrin using the clotting assay, see Table 4.
*** Not Determined.

Synthetic Coagulation Proteome Assay:

This assay is carried out using an established protocol as described previously (Brummel-Ziedens 2008). Briefly, a pro-cofactor solution containing re-lipidated tissue factor (10 pM; molar ratio PCPS:TF=5000) was incubated with 4 μM PCPS in HBS (20 mM HEPES and 150 mM NaCl at pH 7.4) and 2 mM $CaCl_2$ for 8 min at 37° C. Factor V (40 nM) and Factor VIII (1.4 nM) were then added to the mixture prior to initiation of the reaction to activate the protease zymogens in the blood coagulation cascade. The activation reaction was initiated by addition of the pro-cofactor solution to a zymogen solution containing prothrombin (2.8 μM), Factor VII (20 nM), Factor VIIa (0.2 nM), FX (340 nM), Factor IX (180 nM), Factor XI (60 nM), TFPI (5 nM), antithrombin III (6.8 μM) and varied concentrations of the peptides of this invention in HBS, 2 mM $CaCl_2$ pre-equilibrated at 37° C.

At selected time points after initiation of the reaction, 10 μL aliquots were withdrawn from the reaction mixture and quenched in 20 mM EDTA in HBS (pH 7.4) containing 0.2 mM Spectrozyme™ TH and assayed immediately for the proteolytic activity of thrombin. The hydrolysis of Spectrozyme™ TH was monitored by the change in absorbance at 405 nm using a SpectraMax™ plate reader (Molecular Devices Corp., Menlo Park, Calif., USA). Concentration of thrombin generated by the reaction was calculated from a standard curve prepared by serial dilutions of known concentrations of α-thrombin using the fibrinogen clotting assay (DiMaio 1990). Fibrinogen solution was freshly prepared by dissolving about 0.5% (w/v) fibrinogen in 50 mM Tris-HCl, 100 mM NaCl, 0.1% PEG-8000, pH 7.6 and filtering the resulting solution through a hydrophilic membrane of 0.45 μm polyvinylidene fluoride (PVDF) with low protein binding. The concentration of fibrinogen after filtration was determined by using the extinction coefficient of 15.0 for 1% fibrinogen at 280 nm. The fibrinogen clotting assay was initiated by diluting the quenched solutions of activated thrombin 100-300 times into 0.1% fibrinogen in 50 mM Tris-HCl, 100 mM NaCl, 0.1% PEG-8000, pH 7.6. Thrombin-induced clotting of fibrinogen was followed at 25° C. by measuring the optical absorbance at 420 nm. The clotting time was obtained from extrapolation of the slope at the point of inflection to the zero absorbance baseline. The inverse clotting time was used as a measure of thrombin concentration.

Figure 7:
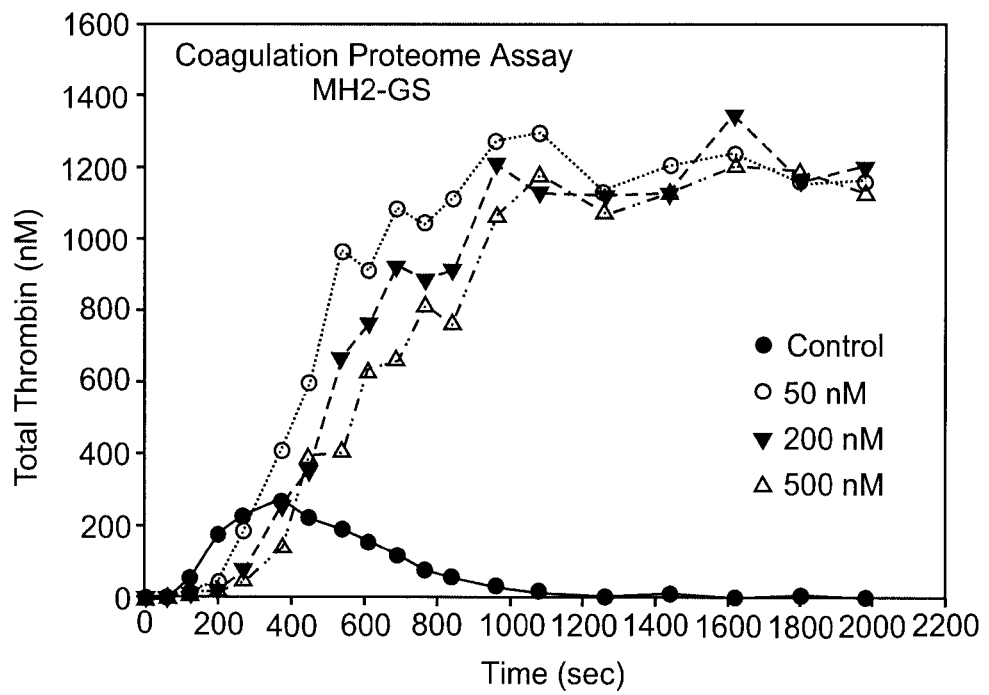
FIG. 7 illustrates human coagulation proteome assays of the inhibitory activities of MH2-GS (upper panel) and MH2-wZIP4 (lower panel).
Figure 7:
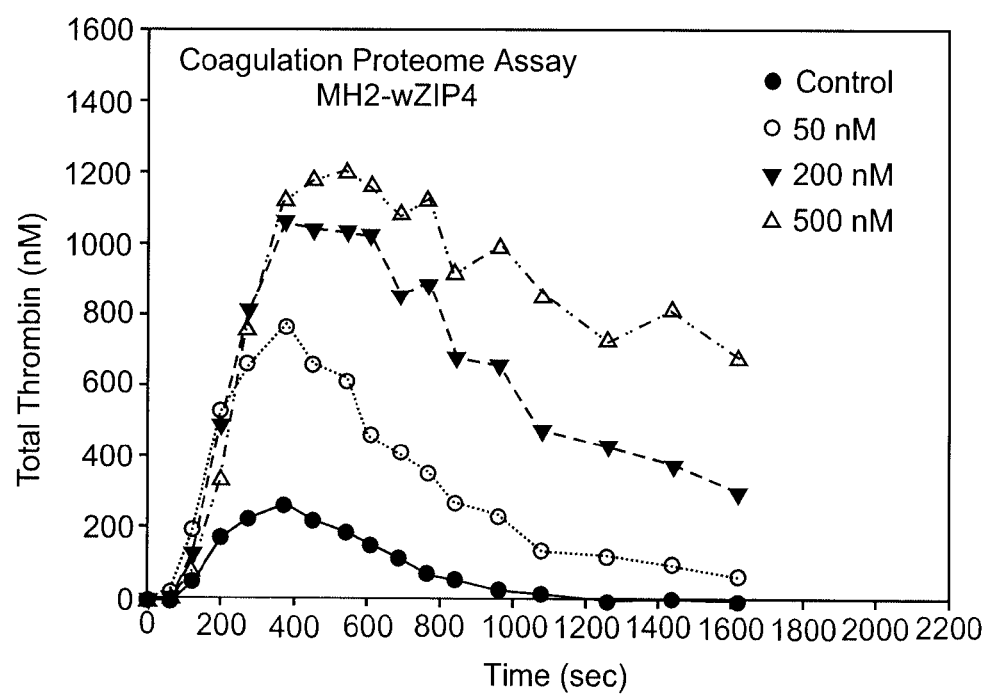
Figure 8:
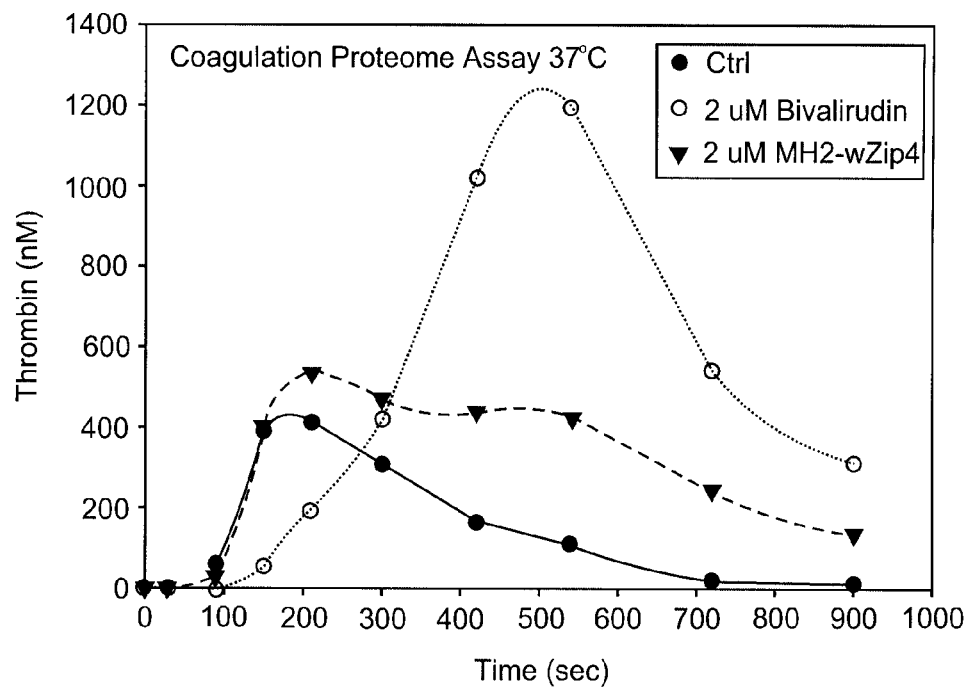
FIG. 8 illustrates human coagulation proteome assays for the bulk temperature dependence of the inhibitory activity of MH2-wZIP4 at 37° C. (upper panel) and 42° C. (lower panel) in comparison to that of bivalirudin/hirulog-1.
Figure 8:
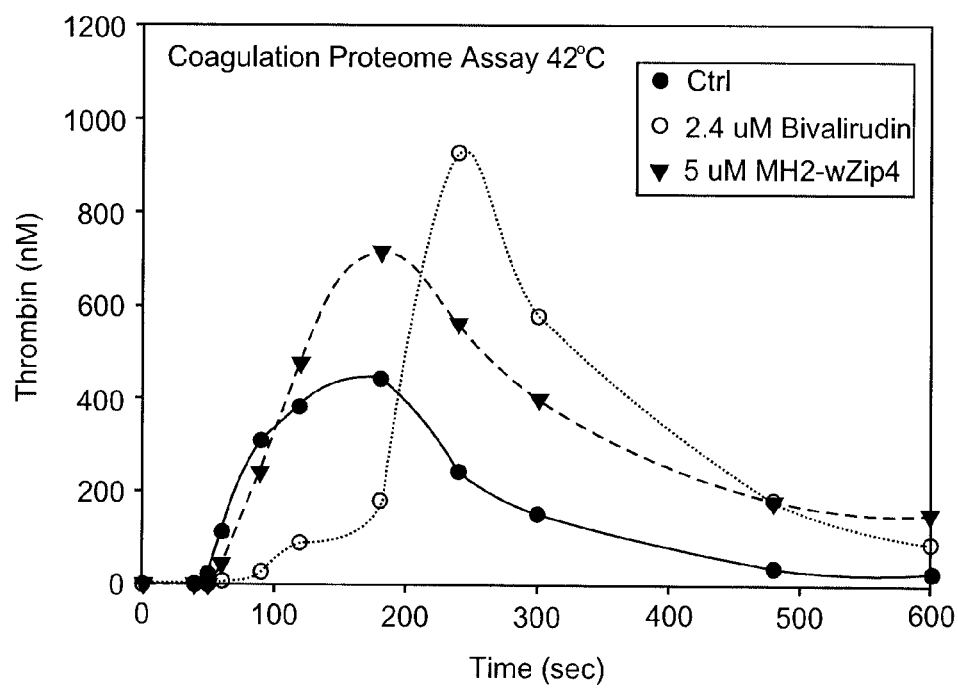

The behaviors of MH2-GS and MH2-wZIP4 in coagulation proteome assays are shown in FIG. 7 and FIG. 8. There is a clear dose-dependency for the delay of thrombin burst by MH2-GS. In comparison, MH2-wZIP4 causes very little delay in the onset of thrombin generation at 37° C. The delaying effect is increased somewhat with the increase of bulk temperature (FIG. 8), possibly due to unfolding (opening) of the trpzip4 linker in MH2-wZIP4 (see FIG. 5A), thereby activating bivalent interactions of MH2-wZIP4 with thrombin (Table 4).

Example 6: Preparation of
Nanoparticle-Immobilized Peptides

The thrombin inhibitors of the present invention can be linked to nanoparticles, e.g. gold or magnetic nanoparticles (GNPs or MNPs), preferably through one or more residues of the linker. In particular, the thrombin inhibitors may be prepared in the form of covalent conjugates with nanoparticles. The size of magnetic nanoparticles is optimal (about 50 nM in diameter) for increased circulation times in plasma. As well, polymer coating present on the surface of nanoparticles can be used for additional potency enhancement through multivalent presentation of the bivalent polypeptides. Nanoparticle conjugation of the bivalent thrombin inhibitors with heat-activatable linkers also enables further localization of inhibitory activities through nanoparticle-mediated heat generation in the presence of RF (radio frequency) fields (Hamad-Schifferli 2002; LaVan 2003) and/or other electromagnetic irradiations. Nanoparticle-mediated heat generation is considered here to include heat that elevates bulk temperature as well as that generates hypermobile water without affecting the bulk temperature detected by devices such as a thermocouple or temperature-sensitive dyes. Magnetic nanoparticles may comprise a coating of an avidin (e.g. streptavidin), which is further coated with biotin. The biotin is in turn linked covalently with a thrombin inhibitor thereby providing a magnetic nanoparticle with the thrombin inhibitor conjugated thereon. Such methods for constructing peptide conjugates to magnetic nanoparticles are generally known (Safarik 2004). Alternatively, the peptide may be covalently bound directly to gold or magnetic nanoparticles by virtue of a chemical reaction between an amino acid residue in the peptide and the surface of the nanoparticles, as illustrated in FIG. 9 and detailed below.

Figure 9:
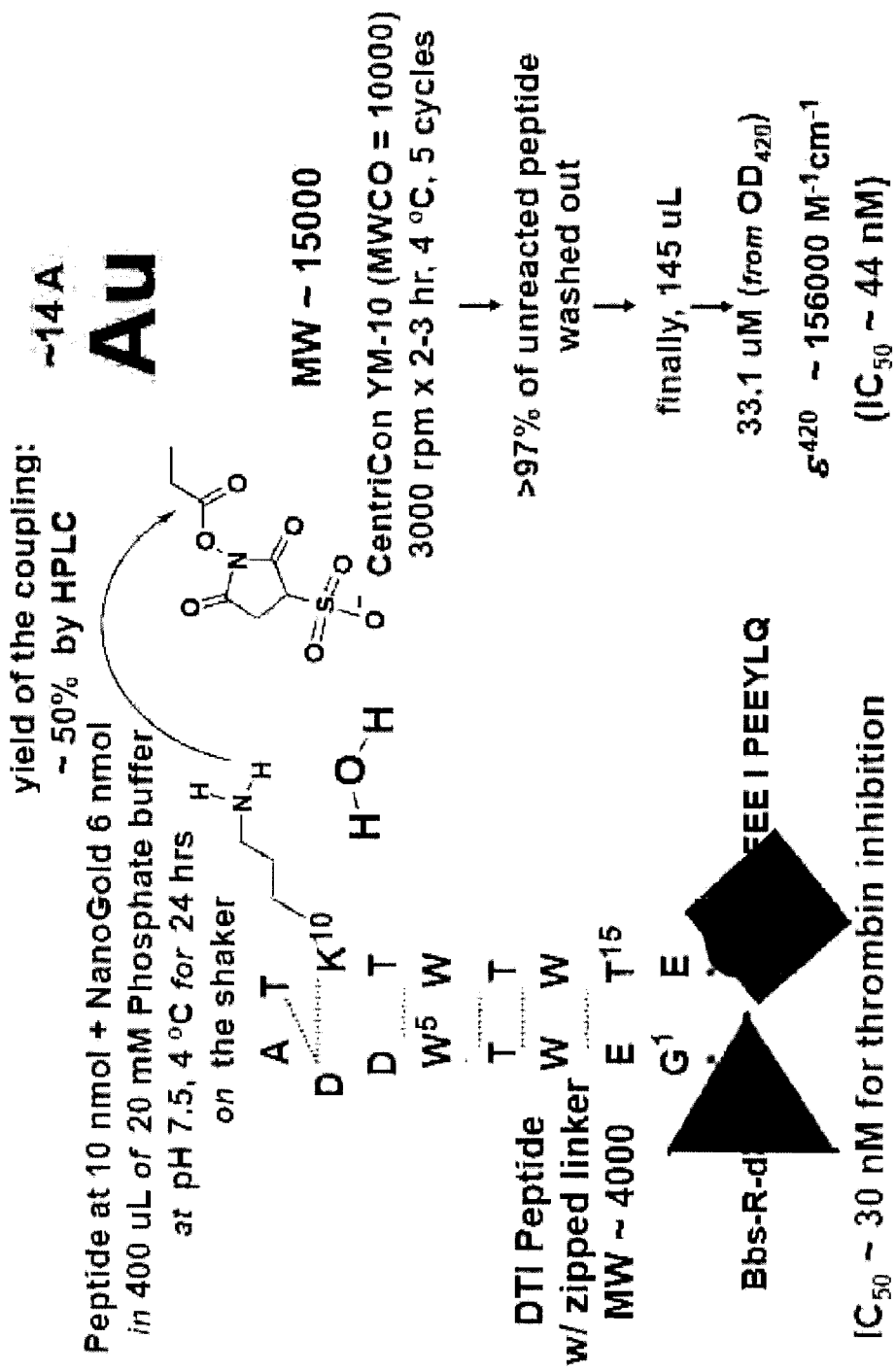
FIG. 9 illustrates conjugation of the thrombin inhibitor BTI5 to a gold nanoparticle and comparison of the inhibitory activities before and after conjugation.

Peptides of this invention are conjugated to gold or magnetic nanoparticles through covalent chemistry (FIG. 9). Two types of dextran-coated nanoparticles are used for covalent conjugation, one with free carboxylates and the second with free amines. 10 mg (300 nmols) (at 10 mg/ml) of MNP-$CO_2$H is activated for 15 minutes by addition of EDC at 0.6 mg (3 μmols) per 60 μl $H_2O$ and sulfo-NHS at 1.73 mg (15 μmols) per 200 μl $H_2O$ before addition of the peptide at 1.5 μmol per 150 μl of 25% $CH_3CN$ in $H_2O$. The reaction is allowed for 2 hours before the reaction mixture is concentrated. 10 mg (300 nmols) (at 10 mg/ml) of MNP-$NH_2$ is activated for 30 minutes by addition of SM(PEG)$_4$ at 4 μl (250 mM) (1 μmol) before addition of the peptide with a free thiol group at 1 μmol per 100 μl in 25% of $CH_3CN$ in $H_2O$. The reaction is allowed to proceed for 30 minutes before the sample is concentrated.

Success of conjugation is illustrated by activity assays for magnetic nanoparticle-immobilized peptides of this invention, especially; BTI3, BTI4, BTI5, MH2-wZIP4, MH2-wZIP5 and MH2-wZIP6 (Table 1) as compared to the respective free peptides. Nanoparticles having multiple copies of the peptides immobilized are identified by more potent inhibition of blood coagulation than the corresponding free peptides.

Example 7: Behavior of Thrombin Inhibitors within Inflamed Tissue Environments by Use of High-Resolution NMR Spectroscopy Accumulation of morphologically-diverse collagen structures is a hallmark of atherosclerotic inflammation and unstable atherosclerotic plaques and it stimulates thrombin formation through platelet adhesion and activation of blood coagulation (Sukhova 1999; Penz 2005; Reininger 2010, Wood 2011). Such de-structurization of aligned tissues is also mimicked by animal models of thrombosis induced by $FeCl_3$ application to blood vessels (Eckly 2011). The MH2-series of heat-activatable thrombin inhibitors, i.e. MH2-wZIP4, MH2-wZIP5 and MH2-wZIP6, are shown here to exhibit significantly-altered conformations within hydrogels formed by type-I collagen, which mimic the physicochemical environment of normal and inflamed tissues (Houdijk 1985; Eckly 2011; Torbet 2007). The next example (Example 8) localizes conformational changes of MH2-wZIP4, MH2-wZIP5, and MH2-wZIP6 induced by collagen to within their respective linker regions, i.e. trpzip4, trpzip5 and trpzip6. Such conformational changes correlate with those associated with the increase of (bulk) temperature or with the formation of hyper mobile water induced by the addition of potassium iodide (KI), thereby qualifying de-structurization of aligned tissues or accumulation of mophogenically-diverse collagens as one important consequence of tissue inflammation.

Rat collagen hydrogels were prepared using rat-tail collagen type I (at 4 mg/ml in 0.02 N acetic acid) from BD Bioscience. A volume of 200 µL of the concentrated collagen solution was mixed with an equal volume of a buffer solution that was 400 mM in Tris.HCl and 400 mM in NaCl with a pH of 7.6 and with 50 µL of deuterated water ($D_2O$). The sample mixture was transferred to an NMR tube followed by gentle mixing under agitation using a Thermolyne™ Max Mix-II apparatus. The NMR tube containing the collagen solution was placed within the RF probe housed in a 500 MHz super-conducting magnet (Bruker Avance-500 NMR spectrometer). The probe and sample bulk temperature was kept at 277 K for 3 hours and then elevated to 310 K at a rate of 1 degree/10 min to enable fibril alignment during a slow process of collagen gelation under the influence of the magnetic field (Ma 2008). The degree of fibril alignment of the collagen hydrogels was determined by use of deuterium NMR spectroscopy of the added $D_2O$ as described (Ma 2008).

Human collagen hydrogels were prepared using either human placenta collagen type I from BD Bioscience (at 2.23 mg/ml in 2 mM HCl) or the VitroCol™ preparation of human collagen from Advanced BioMatrix (at 2.9 mg/ml in 0.01 N HCl). A volume of 400 µL of the concentrated collagen solution was mixed with 50 µL of the solution of 10×PBS (phosphate-buffered saline) supplemented by $Na_2PO_4$ at 500 mM and pH 7.4 and with 50 µL of deuterated water ($D_2O$). The sample mixture was transferred to an NMR tube followed by gentle mixing before being subjected to the same gelation process as described above.

Figure 10A:
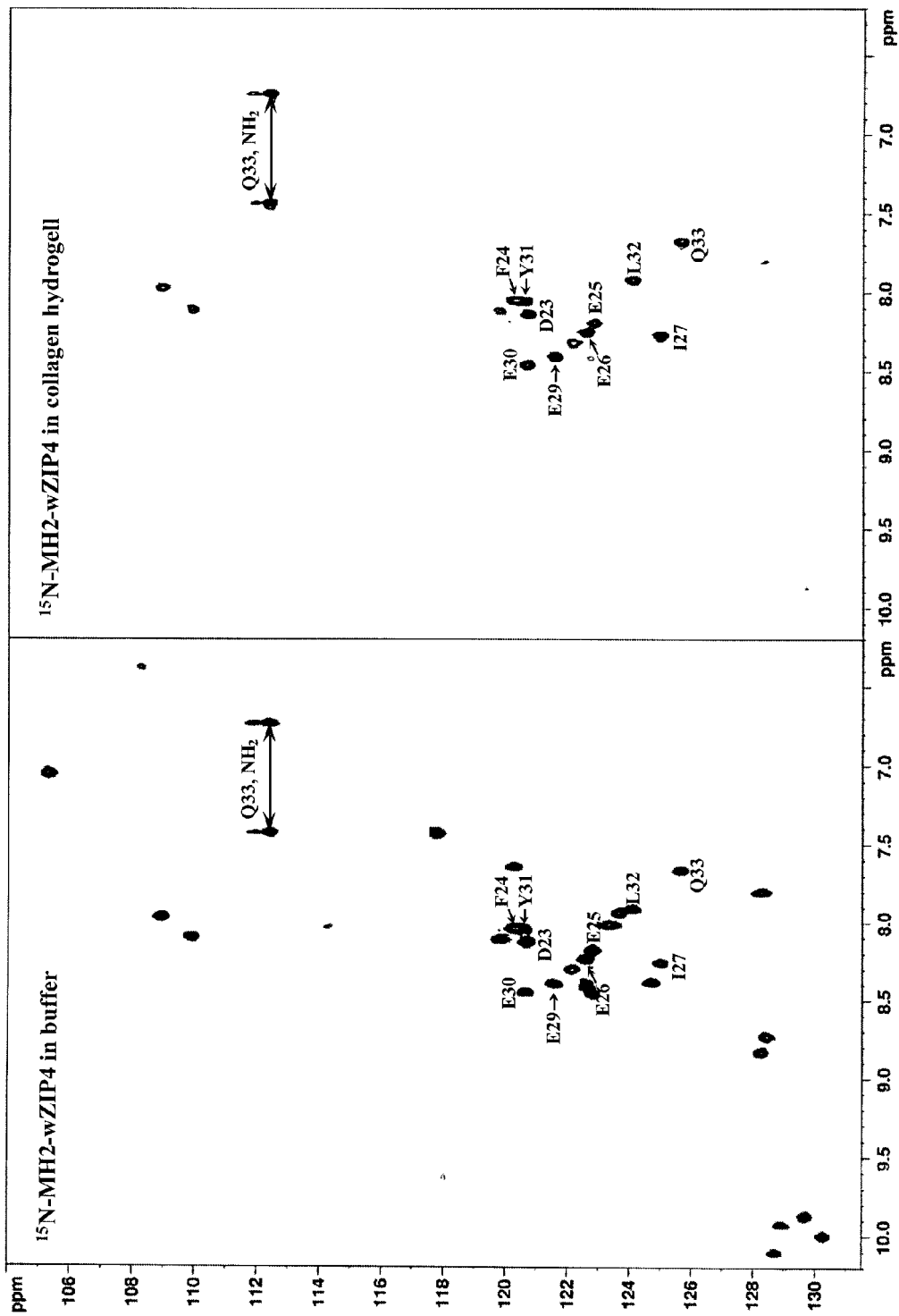
FIG. 10A shows the two-dimensional $(H,^{15}N)$-HSQC spectra of MH2-wZIP4 at a temperature of 298 K in a Tris buffer (left panel, 200 mM Tris-HCl/200 mM NaCl at pH 7.6) and in a randomly-deposited collagen hydrogel (right panel) characteristic of inflamed tissues (Fullerton 2007). Within this type of hydrogel, only part of MH2-wZIP4 exhibits differential resonance perturbations (FIG. 10B), indicating partial entrapment and/or conformational changes. Residues with the sequence motif $GD_{23}FEEIP_{28}EEYLQ_{33}$ (SEQ ID NO: 8) are still fully exposed (visible in NMR spectra), as summarized in FIG. 10B, which shows the relative intensities of the $(H,^{15}N)$-HSQC crosspeaks of $^{15}N$-MH2-wZIP4 in the collagen hydrogel versus those of the free peptide.
Figure 10B:
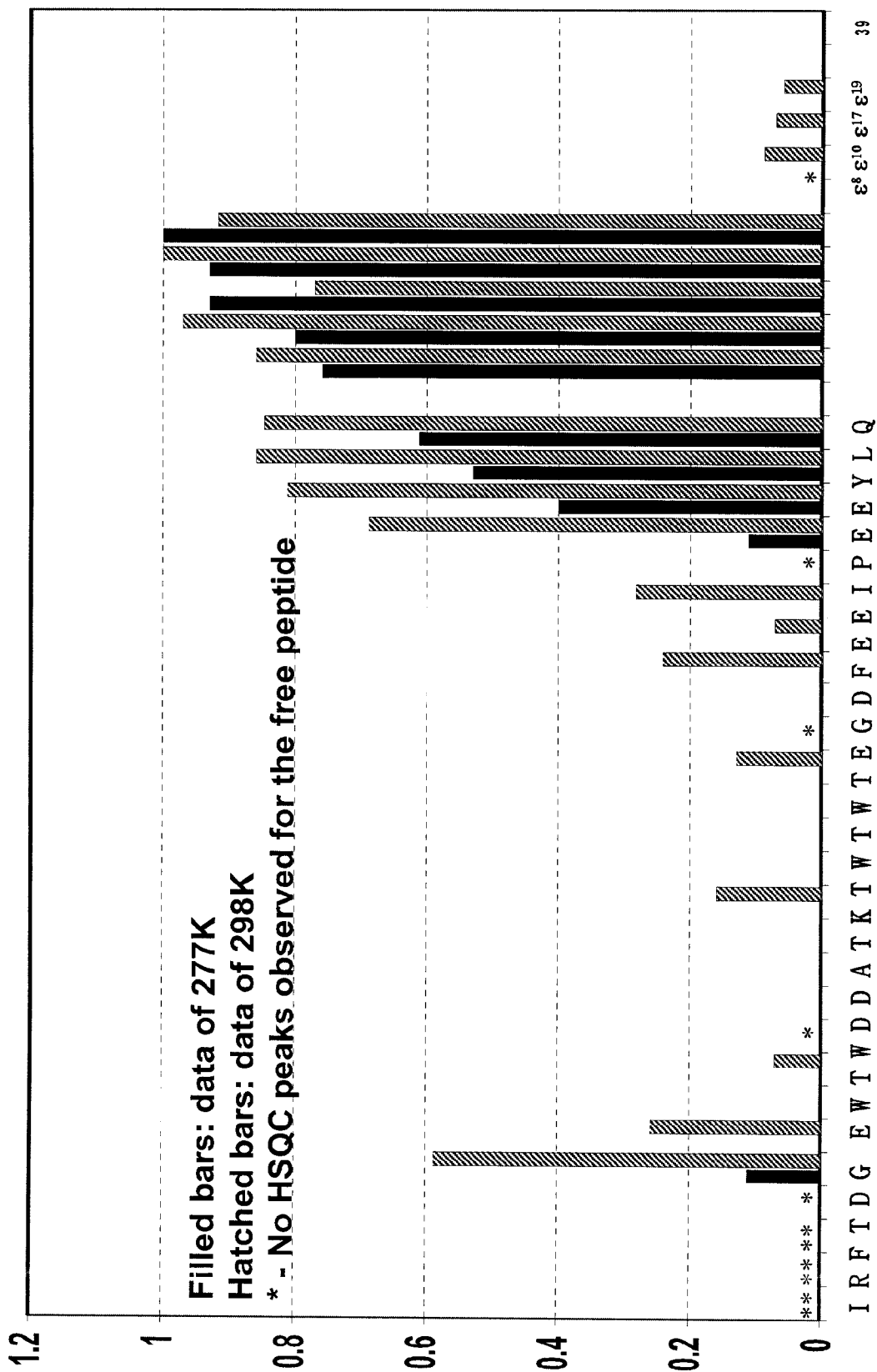
FIG. 10 illustrates the conformational changes of MH2-wZIP4 within the environment of collagen hydrogels.
Figure 11:
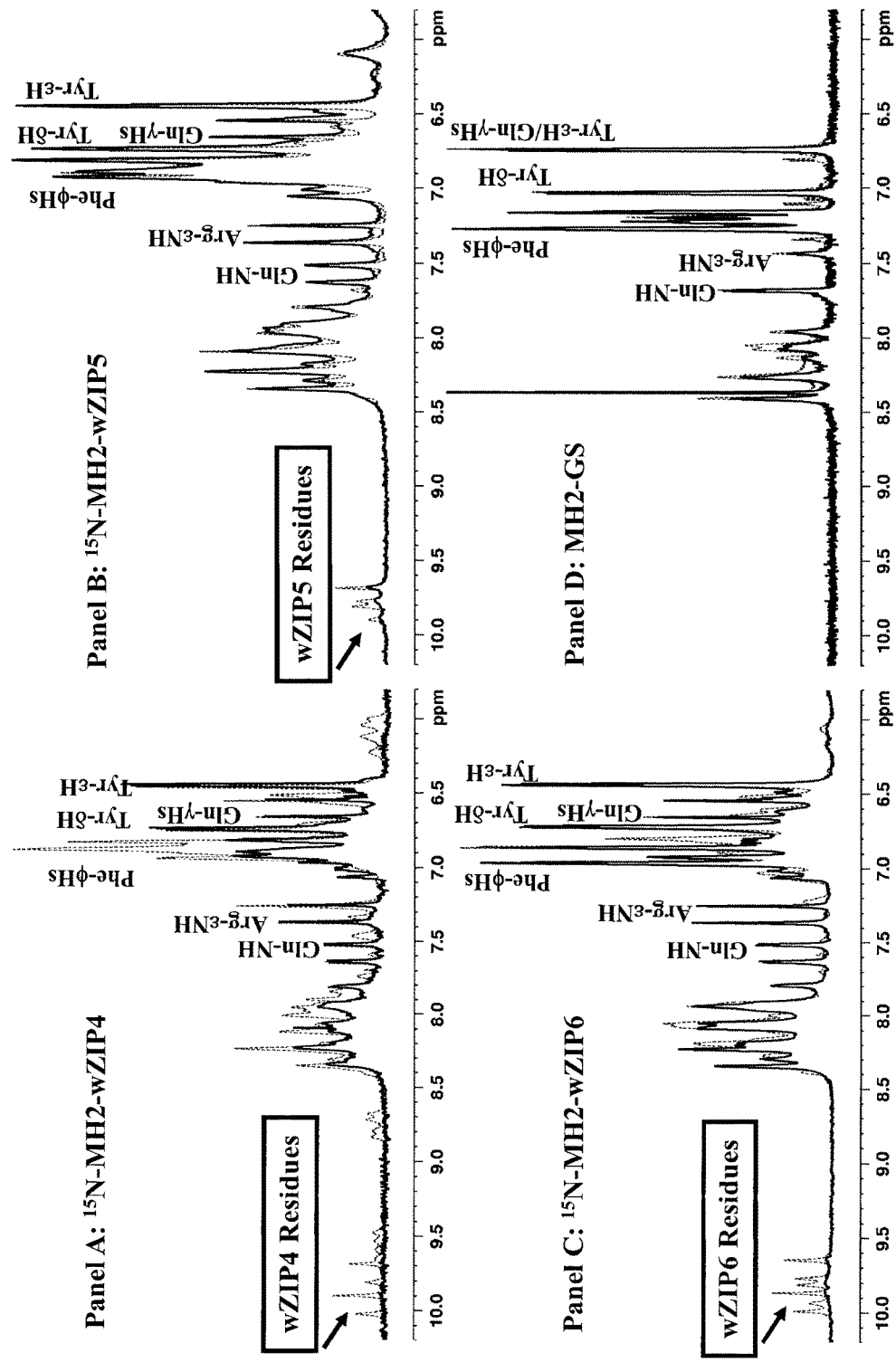
FIG. 11 compares the one-dimensional proton NMR spectra of MH2-wZIP4, MH2-wZIP5, MH2-wZIP6 and MH2-GS in a Tris buffer (thick and black lines) with 200 mM Tris-HCl/200 mM NaCl at pH 7.6 and in collagen hydrogels (thick and dotted lines) formed in the presence of the respective peptides. Proton resonance frequency was 800 MHz and the sample temperatures were 277 K. All samples were prepared by mixing the respective peptides with collagen followed by collagen gelation under magnetic field guidance (Ma, 2008). Proton NMR spectra were nearly identical for MH2-wZIP4 and MH2-GS before and after collagen gelation. Significant resonance sharpening toward those of the free peptide was observed after collagen gelation for the Trp sidechain residues of MH2-wZIP5 and MH2-wZIP6. A few characteristic residues of the peptides are labelled by the respective assignments. The NH proton resonance of the unique glutamine (Gln33) is used here as the internal reference, as this residue is not significantly affected by the presence of collagen (FIG. 10B).

Randomly-deposited collagen (hydrogel) matrix was prepared following the same procedure as above for partially aligned hydrogels, except that the RF probe and the NMR tube containing the collagen solution was placed outside the magnetic field. Peptides of this invention were introduced into the hydrogels in two ways, the first with the collagen stock solution diluted (50:50 in volume ratio) by the buffer of 400 mM in Tris.HCl and 400 mM in NaCl at pH 7.6 containing the peptides of interest, which gelates in the presence of the added peptide. Alternatively, peptides of the present invention in an appropriate buffer were introduced to the top of the hydrogel matrix preformed in the NMR tube following the procedures described above. The diffusion of the peptides into the hydrogels was followed by use of one-dimensional proton NMR spectroscopy and/or by use of $H$-$^{15}N$ HSQC for $^{15}N$-labelled MH2-wZIP peptides (FIGS. 10, 11 and 12).

Evidence that the thrombin inhibitors of the MH2 series have a new mechanism of action comes from a detailed NMR study of the properties of MH2-wZIP4, MH2-wZIP5 and MH2-wZIP6 in the collagen hydrogel as the "mother liquor" of animal tissues (Torbet 2007). NMR data revealed significantly altered properties and/or a differential entrapment of $^{15}N$-MH2-wZIP4 in mis-aligned or randomly deposited collagen hydrogels (FIG. 10). Most importantly, $^{15}N$-MH2-wZIP4 in the collagen hydrogel is shown to have the sequence moiety $GD_{23}FEEIP_{28}EEYLQ_{33}$ (SEQ ID NO: 8) fully exposed and available for binding (FIG. 10A, right panel and FIG. 10B). Additional NMR data demonstrated that both $^{15}N$-MH2-wZIP5 and $^{15}N$-MH2-wZIP6 also exhibit varying degrees of entrapment while the control compound MH2-GS behaves normally showing little entrapment in the collagen (gel) matrix. As shown in FIG. 11, MH2-wZIP4 experiences the most pronounced proton NMR spectral changes within a hydrogel formed from collagen premixed with the peptide. The pronounced changes of MH2-wZIP4 are followed by MH2-wZIP6 and by MH2-wZIP5 in their differential resonance perturbations within the collagen hydrogel. The reference peptide MH2-GS exhibits the least change in the presence of collagen. Such pronounced degrees of proton NMR line broadening, i.e. MH2-wZIP4>MH2-wZIP6>MH2-wZIP5>>MH2-GS are always accompanied by reduced fibril alignment of the hydrogels formed from the corresponding peptide-collagen complex, as determined by use of deuterium NMR spectroscopy.

Figure 12A:
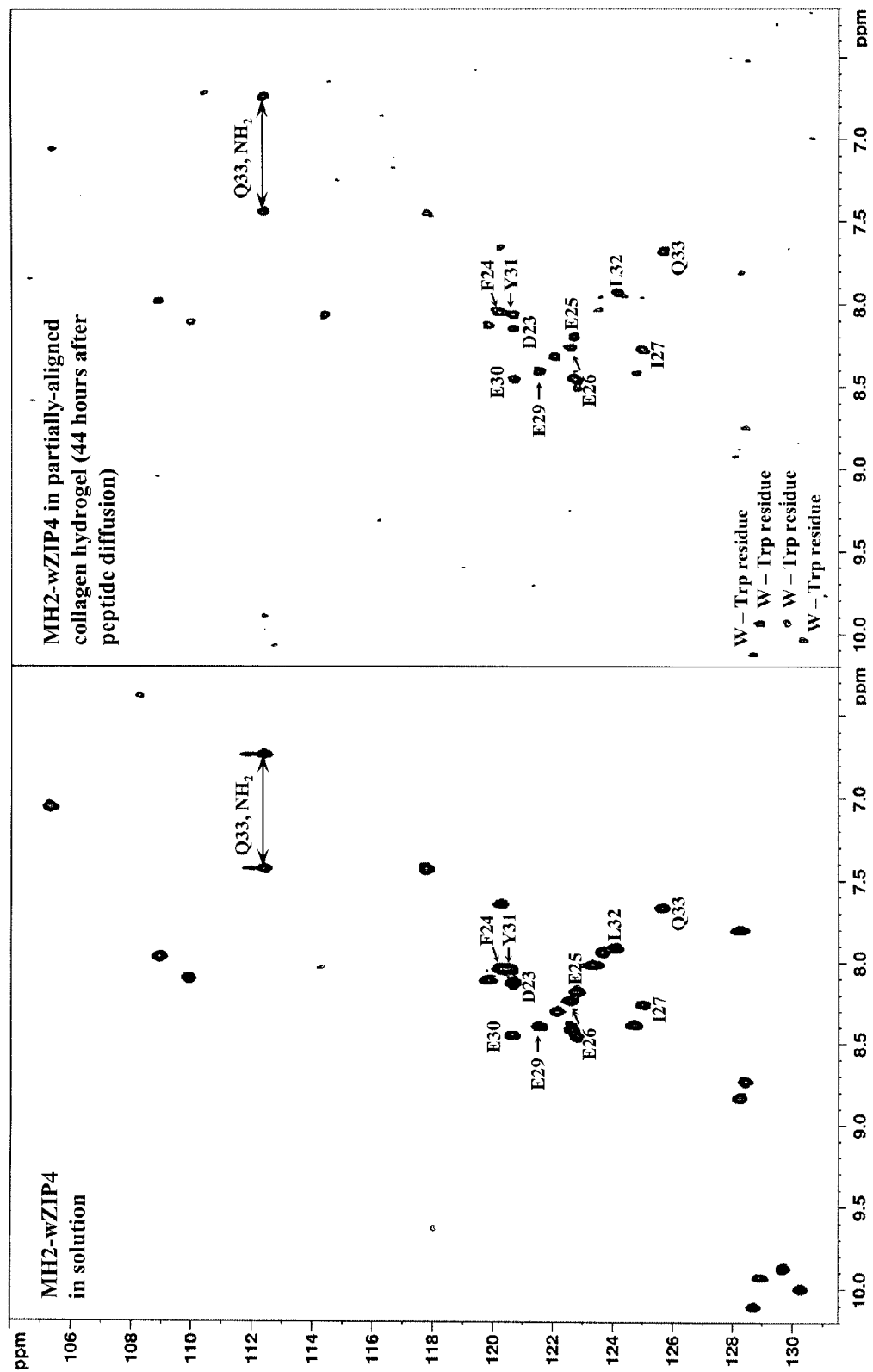
FIG. 12A shows two-dimensional $(H,^{15}N)$-HSQC spectra of MH2-wZIP4 at a temperature of 298 K in a Tris buffer (left panel, 200 mM Tris-HCl/200 mM NaCl at pH 7.6) and after diffusion into a partially-aligned collagen hydrogel (right panel), which is induced by a strong magnetic field (Torbet 2007; Ma 2008). Within the partially-aligned hydrogel, more residues of MH2-wZIP4 become visible (right panel), indicating decreased entrapment compared to within randomly-deposited hydrogel (FIG. 10A, right panel). Again residues with the sequence motif $GD_{23}FEEIP_{28}EEYLQ_{33}$ (SEQ ID NO: 8) are still fully exposed (visible in NMR spectra), similarly to those in the complex of $^{15}N$-MH2-wZIP4 with randomly-deposited collagen hydrogels (FIG. 10A, right panel).

In contrast, the MH2-wZIP4 molecule exhibited a greatly-reduced entrapment (FIG. 12) when diffused into preparations of collagen hydrogels that are pre-aligned to mimic the collagen matrix in healthy tissues (Torbet 2007). In particular, a certain population of MH2-wZIP4 within the partially-aligned hydrogel still exhibits differential entrapment with the GDFEEIPEEYLQ sequence (SEQ ID NO: 8) fully exposed (FIG. 12A, right panel). However, a significant fraction of MH2-wZIP4 showed a reduced degree of entrapment, as indicated by the appearance of NMR signals of Trp residues within the trpzip linker region of MH2-wZIP4 (FIG. 12A, right panel). As a reference, such NMR signals from Trp residues did not appear even after a prolonged period of time (several days to weeks) of leaving MH2-wZIP4 in randomly-deposited collagen hydrogels (FIG. 10A, right panel). During the same long period of time, MH2-wZIP4 exhibited partial degradation in partially-aligned collagen hydrogels (data not shown) accompanied by increased intensities of all the four (4) Trp NMR signals characteristic of the trpzip peptide (FIG. 10A and FIG. 12A, left panel).

Figure 12B:
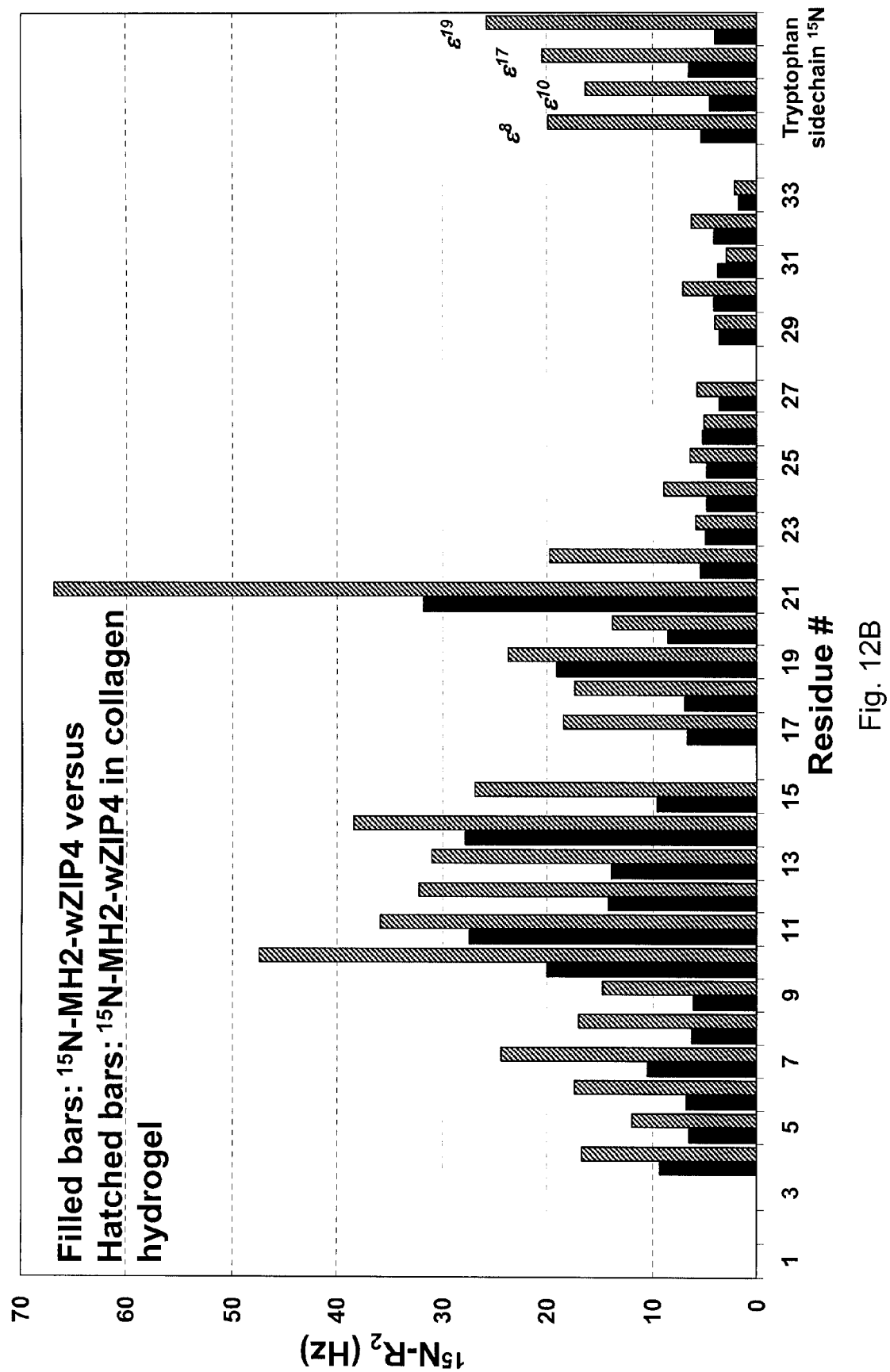
In FIG. 12B, $^{15}N$-NMR transverse $(R_2)$ relaxation rates of MH2-wZIP4 delineate the conformational behavior of MH2-wZIP4 in partially-aligned collagen hydrogels. Display of $^{15}N$-$R_2$ values follows the same schematic as used for those of MH2-wZIP4 and MH2-wZIP5 in buffer only (FIG. 3) (i.e. in 50 mM Tris-HCl/100 mM NaCl and 0.1% PEG-8000 at pH 7.6. NMR data were collected with a proton frequency of 800 MHz and an $^{15}N$ frequency of 80 MHz at a sample temperature of 298 K. A time interval $(\tau_{CPMG})$ of 0.9 ms was used for the refocusing delay (see FIG. 3) of the CPMG $^{15}N$-NMR pulse sequence.

Looking more closely at FIG. 12B, the $^{15}N$-NMR transverse relaxation rates ($R_2$) of $^{15}N$-MH2-wZIP4 show, quantitatively, the differential behavior of each residue in response to the presence of partially-aligned collagen. Therefore, residues in the entire region of $G_{22}DFEEI_{27}PEEYL_{32}Q$ (SEQ ID NO: 8) in MH2-wZIP4 had the least changes in their $^{15}N$-$R_2$ values when comparing $^{15}N$-MH2-wZIP4 in the control (buffer) solution and in partially-aligned collagen hydrogels. Such low $^{15}N$-$R_2$ values for these residues signify the lack of perturbations on these residues by the presence of the collagen matrix, a property of MH2-wZIP4 already evident at the level of (H,$^{15}$N)-HSQC spectral intensities (FIG. 10A and FIG. 12A). In contrast, N-terminal residues of MH2-wZIP4, including the IRFTD segment (SEQ ID NO: 7) as well as the hairpin linker exhibit significantly increased $^{15}$N-R$_2$ values, indicating increased conformational heterogeneity (i.e. unfolding) of the hairpin structure and/or entanglement of these residues by collagen. In addition, the side-chain NH signals of all Trp residues display similar enhancement of $^{15}$N-NMR relaxation, which becomes so large in the presence of unaligned collagen, that their (H,$^{15}$N)-HSQC spectra are no longer observable (FIG. 10A, right panel). This pattern of $^5$N-R$_2$ relaxation enhancement for MH2-wZIP4 induced by collagen is reminiscent of that for MH2-wZIP5 free in solution (FIG. 3A). Therefore, unaligned collagen appears to destabilize (or unfold/open) the trpzip4 β-hairpin in MH2-wZIP4 in a similar fashion as amino acid substitutions (i.e. from the more stable trpzip4 to the less stable trpzip5), or heat-induced denaturation (FIG. 5). In addition to elevations of (bulk) temperatures, inflamed vascular lesions and atherosclerotic plaques are also decorated with structurally-diverse collagen fibrils and fragmented collagens, which are promoted largely by the local expression of proteases, especially MMPs or Matrix Metalloproteases (Sukhova 1999; Penz 2005; Tan 2008; Adiguzel 2009). Such literature knowledge and NMR experiments detailed in this invention therefore provide part of the mechanistic picture for the localized anti-thrombotic properties of MH2-wZIP4 demonstrated by the rat model of venous thrombosis (Example 11, FIG. 19).

Example 8: Behavior of Heat-Sensitive Linker Peptides in Collagen Hydrogels Determined by Use of High-Resolution NMR Spectroscopy High-resolution proton NMR spectroscopy is used to illustrate the behavior of the linker peptides GEWTYDDATKTFTVTE (SEQ ID NO: 2 or gb1), GEWTWDDATKTWTVTE (SEQ ID NO: 3 or trpzip6), GEWTYDDATKTFTWTE (SEQ ID NO: 4 or trpzip5) and GEWTWDDATKTWTWTE (SEQ ID NO: 5 or trpzip4) in aqueous solutions. The peptides were synthesized using standard Fmoc chemistry and purified by reverse-phase HPLC. Their identity was confirmed by mass-spectroscopy and NMR spectroscopy. For NMR studies, a volume of (400-X) μL of a peptide dissolved in pure water was mixed with 50 μL of a 10×PBS (phosphate-buffered saline) supplemented by sodium phosphate to a final concentration of 50 mM and with 50 μL of deuterated water (D$_2$O) to form the reference sample (where X=0) and with a certain volume (X μL) of rat-tail collagen type I (at 3.6 to 4 mg/ml in 0.02 N acetic acid from BD Bioscience), (where X is adjusted to achieve the desired final concentration of collagen), with 50 μL of the 10× modified PBS and with 50 μL of deuterated water (D$_2$O) to form the peptide-collagen complex. The pH value of the reference peptide samples was adjusted to match the pH of the final peptide-collagen complex in order to facilitate NMR spectral comparison.

The peptide-collagen solutions were subjected to gelation under magnetic field guidance (see Example 7) followed by the measurement of fibril alignment (Ma 2008) as a semi-quantitative indication of peptide-collagen binding. Deuterium coupling constants measuring the degree of collagen fibril alignment were reduced by more than 1.0 Hz for trpzip4, by less than 0.5 Hz for trpzip6 and trpzip5 and were not significantly affected by the gb1 peptide, which parallel those observed for the bivalent thrombin inhibitors MH2-wZIP4, MH2-wZIP6, MH2-wZIP5 and MH2-GS. As a comparison, a solution of rat collagen at a concentration of 1.8 mg/ml in 200 mM Tris-Cl/200 mM NaCl at pH 7.6 formed a partially-aligned hydrogel with a deuterium coupling constant (Ma, 2008) of 2.5 Hz, while a solution of rat collagen at a concentration of 3 mg/ml in PBS (137 mM NaCl/2.68 mM KCl/10.1 mM Na$_2$HPO$_4$/1.76 mM KH$_2$PO$_4$) supplemented with Na$_2$HPO$_4$ to achieve a final concentration of 50 mM at pH 7.4 formed a partially-aligned hydrogel with a deuterium coupling constant of 4.8 Hz. A solution of human collagen at a concentration of 2.23 mg/ml in PBS supplemented with Na$_2$HPO$_4$ with a final concentration of 50 mM at pH 7.4 formed a partially-aligned hydrogel with a deuterium coupling constant of 1.3 Hz.

Therefore, peptide GEWTYDDATKTFTVTE (SEQ ID NO: 2 or gb1) has little change of its conformation in the collagen hydrogel (FIG. 13, Panel A), neither its presence impacts the gelation process of collagen since the degree of gel alignment as measured by the deuterium coupling constant remained similar with or without the peptide. In sharp contrast, peptide trpzip4 (GEWTWDDATKTWTWTE or SEQ ID NO: 5) is dramatically altered by collagen (FIG. 13, Panel B), which in the presence trpzip4, exhibits a greatly-reduced capacity to gelate and a significantly reduced degree of alignment. Both trpzip5 and trpzip6 change moderately in the presence of collagen (FIG. 13, Panel C and D), and the spectral changes of trpzip5 and trpzip6 induced by collagen revert toward those of the free peptides after collagen polymerization (gelation). Furthermore, the trpzip5 peptide in the collagen solution reverts to a greater extent as compared to trpzip6 toward the free state after collagen polymerization (NMR spectra not shown), which is paralleled by similar observations with the bivalent peptides MH2-wZIP5 and MH2-wZIP6. These NMR results demonstrate that specific interactions of the MH2-series of thrombin inhibitors with collagen are conferred primarily by the unique properties of the linker segments, as represented by the peptides trpzip4 (SEQ ID NO: 5), trpzip5 (SEQ ID NO: 4) and trpzip6 (SEQ ID NO: 3).

The proton NMR spectra of trpzip4-NH$_2$, trpzip5-NH$_2$, trpzip6-NH$_2$, and gb1-NH$_2$ (FIG. 13) also illustrate a progressive unfolding or opening of the β-hairpin structure in response to specific amino acid substitutions in these peptides (Cochran 2001). Therefore, trpzip4-NH$_2$ exhibits a characteristic hairpin structure, as indicated by the two significantly downfield shifted NH proton resonances between 9.5 to 9.7 ppm (FIG. 13, Panel B), which belong to residues Thr9 and Thr18, respectively (FIG. 5A) and by the two overlapped NH signals at 8.85 ppm, which come from residues Trp10 and Trp19. Peptide trpzip5-NH$_2$ has a less stable hairpin structure, as its NH resonance envelop contracts to start at about 9.3 ppm (FIG. 13, Panel C) from the 9.7 ppm for trpzip4-NH$_2$. In addition, the NH resonance of trpzip5-NH$_2$, especially those between 8.8 and 9.3 ppm have broad line shapes (FIG. 13, Panel C) which are characteristic of conformational exchanges, here between the closed β-hairpin structure and the open polypeptide chain. The β-hairpin structure in trpzip6-NH$_2$ is also quite unstable since some of its NH resonances, i.e. those between 8.8 and 9.5 ppm (FIG. 13, Panel D) exhibit very broad line shapes. These NMR characteristics are in exact parallel with the thermostability of the four hairpin peptides, i.e. with T$_m$ about 70° C. for trpzip4, T$_m$ about 43° C. for trpzip5, T$_m$ about 45° C. for trpzip6 and T$_m$ about 7° C. for gb1, as reported previously (Cochran 2001). The increased conformational stability of the trpzip4 β-hairpin allows it to persist when the trpzip4 sequence is used as a linker in bivalent thrombin inhibitors, as MH2-wZIP4 is the only inhibitor of the MH2-series to have characteristic downfield-shifted NH proton resonances, i.e. those from Thr9, Trp10, Thr18 and Trp19 (FIG. 5A and FIG. 11). The conformational characteristics as reflected by the proton NMR spectra are intrinsic properties of the respective hairpin peptides, since all four peptides, i.e. gb1-NH$_2$, trpzip4-NH$_2$, trpzip5-NH$_2$ and trpzip5-NH$_2$ show the same NMR spectral signatures (FIG. 13) whether the sample solutions contain the modified PBS buffer (supplemented by 50 mM Na$_2$HPO$_4$) or are prepared in 50 mM Tris-HCl, 100 mM NaCl, 0.1% PEG-8000 at pH 7.6 (spectra not shown).

Example 9: Controlled Delivery of Locally-Activatable Thrombin Inhibitors

Figure 14B:
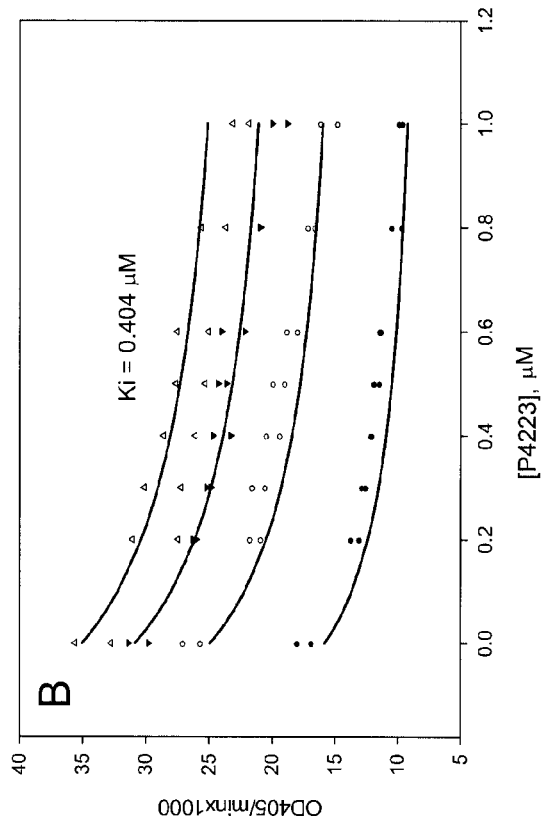
FIG. 14 illustrates the thrombin inhibitory activities of peptides BRI-T109, BRI-T207, BRI-T208, and BRI-T218 (Table 6) as measured by thrombin-catalyzed substrate hydrolysis. BRI-T109, BRI-T207, BRI-T208 and BRI-T218 are designated as P4230 (FIG. 14A), P4223 (FIG. 14B), P4229 (FIG. 14C) and P4238 (FIG. 14D), respectively, in these plots. A time window of 50s was used to follow the rate of substrate hydrolysis under the influence of BRI-T218 (P4238) (FIG. 14D) since at long times, BRI-T218 loses its inhibitory activity due to cleavage at the (d)FPR-IRFTD . . . junction catalyzed by thrombin (see FIG. 15).
Figure 14A:
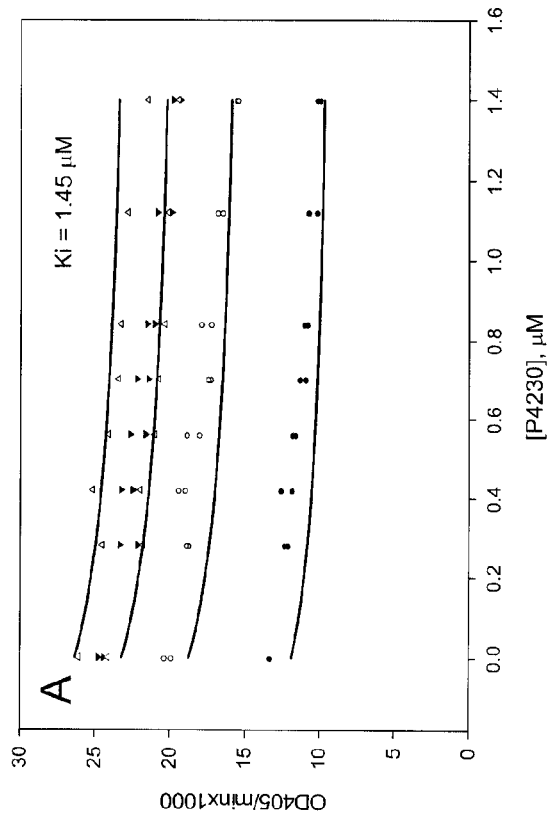
Figure 14D:
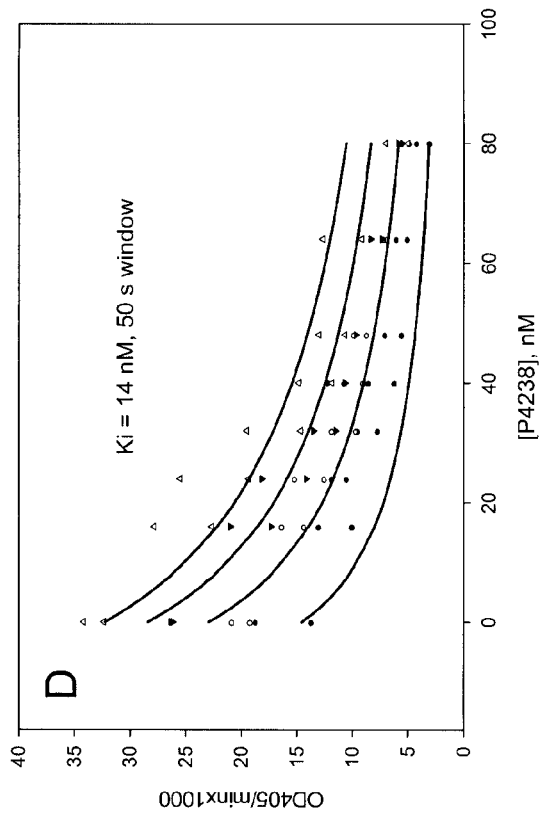
Figure 14C:
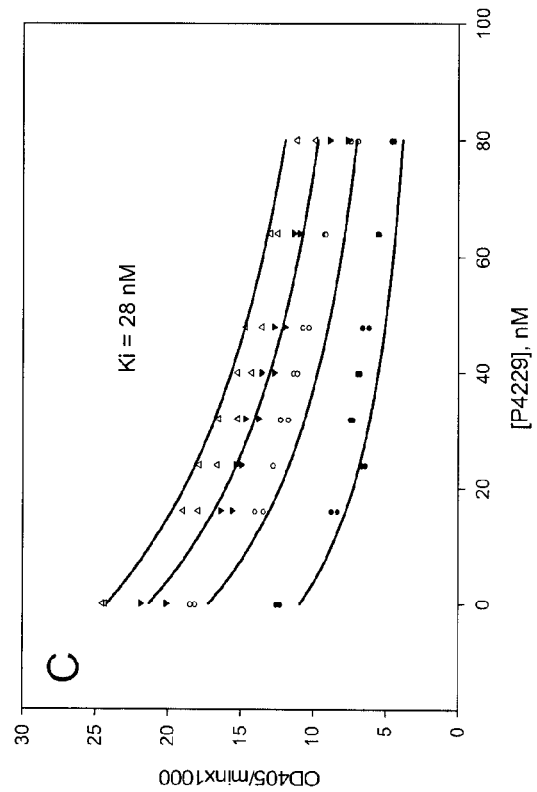

Locally-active thrombin inhibition can be further achieved through controlled release whereby an active inhibitor of this invention, especially those of the MH2 series (Table 1) including MH2-wZIP1-2G and MH2-wZIP1 (Table 6), is generated by unique enzymes in thrombogenic tissues, similarly to what has been achieved with recombinant hirudin (Peter 2003; Peter 2000). Heat-activatable thrombin inhibitors, e.g. MH2-wZIP4, can include an extension of enzyme-recognition sites to the N-terminus of these peptides:

(SEQ ID NO: 40)
x$_4$x$_3$x$_2$x$_1$-IRFTDGEWTWDDATKTWTWTEGDFEEIPEEYLQ where x$_4$x$_3$x$_2$x$_1$ are any amino acids that covalently block the access of the IRFTD moiety (SEQ ID NO: 7) to the active site of thrombin. In this regard, the MH2 (minihirudin 2) series of thrombin inhibitors have the same mechanism of action as hirudin, in that the sequence moiety IRFTD (SEQ ID NO: 7) binds to the active site of thrombin in a reverse orientation as compared to substrates (Rydel 1990; Lazar 1991; Corral-Rodriguez 2010). FIG. 14A shows that an analog of MH2-wZIP4, named BRI-T109 (Table 6), has a diminished inhibitory activity when the first residue Ile is replaced by a Pro. The PRFTD motif (SEQ ID NO: 41) in BRI-T109 still binds to the active side of thrombin as BRI-T109 interferes moderately with the catalytic function of thrombin (K$_i$=1.45 µM) (FIG. 14A). Such sensitivity to the nature of the N-terminal residues is the hallmark of hirudin (Betz 1992; Corral-Rodriguez 2010) and other variants of hirudin (Lombardi 1996), which further demonstrates that the thrombin inhibitory activity of the MH2 series of bivalent peptides can be controlled through N-terminal modifications. Such modifications include the use of a factor Xa-sensitive cleavage site before the IRFTD moiety (SEQ ID NO: 7), i.e. with x$_4$x$_3$x$_2$x$_1$=Ile-Glu-Gly-Arg (SEQ ID NO: 43), as reported for a FXa-activated construct of hirudin (Peter 2000) or with x$_4$x$_3$x$_2$x$_1$=other substrates of FXa (Hsu 2008). Examples of such FXa-activatable bivalent thrombin inhibitors include:

(SEQ ID NO: 49)
IEGR-IRFTDGEWTWDDATKTWTWTE-GDFEEIPEEYL (BRI-T204)

(SEQ ID NO: 50)
IEGR-IRFTDGEWTYDDATKTFTWTE-GDFEEIPEEYL (BRI-T205)

where BRI-T205 is based on the sequence of MH2-wZIP5 (SEQ ID NO: 17) similarly as BRI-T204 is constructed from MH2-wZIP4 (SEQ ID NO: 18). Both BRI-T204 and BRI-T205 are themselves also bivalent thrombin inhibitors since the IEGR moiety (SEQ ID NO: 43) is a substrate of thrombin by sequence similarity with other substrate sequences such as FNPR (SEQ ID NO: 70) (NI 1995) or IQPR (SEQ ID NO: 38) (Su 2004). In this regard, such overlap of substrate recognition between FXa and thrombin is unavoidable (Wardentin 2004) due to the fact that both FXa and thrombin are closely-related serine proteases with similar mechanisms for substrate cleavage.

A construct of practical utility incorporates an optimized thrombin-sensitive site into the x$_4$x$_3$x$_2$x$_1$ sequence moiety, e.g. in the form of the following compound, BRI-T207:

(SEQ ID NO: 44)
FQPR-*P*RFTDGEWTWDDATKTWTWTE-GDFEEIPEEYL.

TABLE 6

Amino Acid Sequences of Other Locally-Active Thrombin Inhibitors

| Name | Linker | Sequence |
| --- | --- | --- |
| BRI-T109 | trpzip4 | PRFTD-GEWTWDDATKTWTWTE-GDFEEIPEEYLQ (SEQ ID NO: 45) |
| BRI-T110 | trpzip4 | PRFTD-GEWTWDDATKTWTWTE-GDFEEIPEEYL (SEQ ID NO: 46) |
| BRI-T111 | trpzip4 | IRFTD-GEWTWDDATKTWTWTE-GDFEEIPEEYL (SEQ ID NO: 47) |
| BRI-T113 | trpzip4 | (d)FPRP-GEWTWDDATKTWTWTE-GDFEEIPEEYL (SEQ ID NO: 48) |
| BRI-T204 | IRFTD-trpzip4 | IEGR-IRFTDGEWTWDDATKTWTWTE-GDFEEIPEEYL (SEQ ID NO: 49) |
| BRI-T205 | IRFTD-trpzip5 | IEGR-IRFTDGEWTYDDATKTFTWTE-GDFEEIPEEYL (SEQ ID NO: 50) |
| BRI-T207 | PRFTD-trpzip4 | FQPR-*P*RFTDGEWTWDDATKTWTWTE-GDFEEIPEEYL (SEQ ID NO: 44) |
| BRI-T217 | IRFTD-trpzip4 | FQPR-*I*RFTDGEWTWDDATKTWTWTE-GDFEEIPEEYL (SEQ ID NO: 51) |

TABLE 6-continued

Amino Acid Sequences of Other Locally-Active Thrombin Inhibitors

| Name | Linker | Sequence |
| --- | --- | --- |
| BRI-T227 | VRFTD-trpzip4 | FQPR-VRFTDGEWTWDDATKTWTWTE-GDFEEIPEEYL (SEQ ID NO: 52) |
| BRI-T237 | LRFTD-trpzip4 | FQPR-LRFTDGEWTWDDATKTWTWTE-GDFEEIPEEYL (SEQ ID NO: 53) |
| BRI-T247 | FRFTD-trpzip4 | FQPR-FRFTDGEWTWDDATKTWTWTE-GDFEEIPEEYL (SEQ ID NO: 54) |
| BRI-T208 | PRFTD-trpzip4 | (d)FPR-PRFTDGEWTWDDATKTWTWTE-GDFEEIPEEYL (SEQ ID NO: 55) |
| BRI-T218 | IRFTD-trpzip4 | (d)FPR-IRFTDGEWTWDDATKTWTWTE-GDFEEIPEEYL (SEQ ID NO: 56) |
| BRI-T228 | VRFTD-trpzip4 | (d)FPR-VRFTDGEWTWDDATKTWTWTE-GDFEEIPEEYL (SEQ ID NO: 57) |
| BRI-T238 | LRFTD-trpzip4 | (d)FPR-LRFTDGEWTWDDATKTWTWTE-GDFEEIPEEYL (SEQ ID NO: 58) |
| BRI-T248 | FRFTD-trpzip4 | (d)FPR-FRFTDGEWTWDDATKTWTWTE-GDFEEIPEEYL (SEQ ID NO: 59) |
| BRI-T209 | PRFTD-trpzip4 | WDPR-PRFTDGEWTWDDATKTWTWTE-GDFEEIPEEYL (SEQ ID NO: 60) |
| BRI-T219 | IRFTD-trpzip4 | WDPR-IRFTDGEWTWDDATKTWTWTE-GDFEEIPEEYL (SEQ ID NO: 61) |
| BRI-T229 | VRFTD-trpzip4 | WDPR-VRFTDGEWTWDDATKTWTWTE-GDFEEIPEEYL (SEQ ID NO: 62) |
| BRI-T239 | LRFTD-trpzip4 | WDPR-LRFTDGEWTWDDATKTWTWTE-GDFEEIPEEYL (SEQ ID NO: 63) |
| BRI-T249 | FRFTD-trpzip4 | WDPR-FRFTDGEWTWDDATKTWTWTE-GDFEEIPEEYL (SEQ ID NO: 64) |
| BRI-T210 | PRFTD-trpzip5 | (d)FPR-PRFTDGEWTYDDATKTFTWTE-GDFEEIPEEYL (SEQ ID NO: 65) |
| BRI-T220 | IRFTD-trpzip5 | (d)FPR-IRFTDGEWTYDDATKTFTWTE-GDFEEIPEEYL (SEQ ID NO: 66) |
| BRI-T230 | VRFTD-trpzip5 | (d)FPR-VRFTDGEWTYDDATKTFTWTE-GDFEEIPEEYL (SEQ ID NO: 67) |
| BRI-T240 | LRFTD-trpzip5 | (d)FPR-LRFTDGEWTYDDATKTFTWTE-GDFEEIPEEYL (SEQ ID NO: 68) |
| BRI-T250 | FRFTD-trpzip5 | (d)FPR-FRFTDGEWTYDDATKTFTWTE-GDFEEIPEEYL (SEQ ID NO: 69) |
| BRI-T304 | trpzip4 | IRFTD-GEWTWDDATKTWTWTE-GEFEEFEIDEEEK (SEQ ID NO: 78) |
| BRI-T404 | trpzip4-GGS | IRFTD-GEWTWDDATKTWTWTE-GGS-[VH-PEPA1] (SEQ ID NO: 79) |
| VSL-PEPA1 | PQLHNDGGGSS | GSVSPRPQLHNDGGGSS-[VH-PEPA1] (SEQ ID NO: 80) |
| MH2-wZIP1-2G | G G-trpzip1-G | IRFTDG-GSWTWEGNKWTWKG-GDFEEIPEEYLQ (SEQ ID NO: 82) |
| MH2-wZIP1 | G-trpzip1 | IRFTDG-SWTWEGNKWTWK-GDFEEIPEEYLQ (SEQ ID NO: 83) |

TABLE 7

Activities of N-Terminally Blocked Thrombin Inhibitors Constructed from MH2-wZIP4

| Name | Linker | Full Sequence | $K_i$, nM**, T = 37° C. |
|---|---|---|---|
| BTI5 | trpzip4 | Bbs-Arg-(D-Pip)-GEWTWDDATKTWTWTE-GDFEEIPEEYLQ (SEQ ID NO: 13) | 13 |
| MH2 | HV2(42-53) | IRFTD-GEGTPNPESHNN-GDFEEIPEEYLQ (SEQ ID NO: 34) | 14 ($IC_{50}$) |
| MH2-allGS | (GS)$_6$ | IRFTD-GSGSGSGSGSGS-GDFEEIPEEYLQ (SEQ ID NO: 35) | 58 |
| MH2-wZIP4 | trpzip4 | IRFTD-GEWTWDDATKTWTWTE-GDFEEIPEEYLQ (SEQ ID NO: 18) | 154 ($IC_{50}$) |
| BRI-T109 | trpzip4 | PRFTD-GEWTWDDATKTWTWTE-GDFEEIPEEYLQ (SEQ ID NO: 45) | 1450 |
| BRI-T207 | PRFTD-trpzip4 | FQPR_PRFTD-GEWTWDDATKTWTWTE-GDFEEIPEEYL (SEQ ID NO: 44) | 404 |
| BRI-T208 | PRFTD-trpzip4 | (d)FPR_PRFTD-GEWTWDDATKTWTWTE-GDFEEIPEEYL (SEQ ID NO: 55) | 28 |
| BRI-T218 | IRFTD-trpzip4 | (d)FPR_IRFTD-GEWTWDDATKTWTWTE-GDFEEIPEEYL (SEQ ID NO: 56) | 14 |
| BRI-T219 | IRFTD-trpzip4 | WDPR_IRFTD-GEWTWDDATKTWTWTE-GDFEEIPEEYL (SEQ ID NO: 61) | 164 |
| MH2-wZIP1-2G | GG-trpzip1-G | IRFTD-GGSWTWEGNKWTWKG-GDFEEIPEEYLQ (SEQ ID NO: 82) | 16.6 |
| MH2-wZIP1 | trpzip1 | IRFTD-GSWTWEGNKWTWK-GDFEEIPEEYLQ (SEQ ID NO: 83) | 18.4 |

**Each value of $K_i$ was determined from enzyme kinetics experiments performed in duplicates.

The tetrapeptide FQPR (SEQ ID NO: 26) is a variant of the optimal substrate-recognition motif, FNPR (SEQ ID NO: 70), by the active site of thrombin (Ni 1995). This extended form of MH2-wZIP4, i.e. BRI-T207 also has the first residue substituted by a Pro (i.e. in the PRFTD segment (SEQ ID NO: 41)) and the last residue removed (similarly for BRI-T204 and BRI-T205) as this Gln residue is not required for binding to the fibrinogen-recognition site of thrombin (Maraganore 1990; Su 2004). BRI-T207 is a bivalent inhibitor of thrombin with a $K_i$ of about 400 nM as determined by the inhibition kinetics on the thrombin cleavage of a chromogenic substrate (FIG. 14B and Table 7). With a bivalent mode of action thus established for BRI-T207, the potency for thrombin inhibition can be enhanced relatively easily if the FQPR moiety (SEQ ID NO: 26) is substituted with other peptides or small molecules that have higher affinities for the active site of thrombin (Table 3). These thrombin-binding moieties include, e.g. (d)Phe-Pro-Arg (dFPR as in hirulog-1/bivalirudin), the Bbs-Arg-(d)Pip sequence or other tetrapeptide sequences derived from Phe-Gln-Pro-Arg (FQPR (SEQ ID NO: 26)) such as Trp-Asp-Pro-Arg (WDPR (SEQ ID NO: 27)) or IQPR (SEQ ID NO: 38).

With (d)FPR replacing FQPR (SEQ ID NO: 26), BRI-T207 is transformed into a molecule BRI-T208 (SEQ ID NO: 55) that carries all the functional structures of hirulog-1 or bivalirudin (Maraganore 1990). In other words, full-length BRI-T208 would work like hirulog-1 (bivalirudin) for thrombin inhibition, except that the linker segment (Gly)$_4$-Asn (SEQ ID NO: 71) in bivalirudin is replaced by a new peptide sequence containing the trpzip4 moiety. BRI-T208 has a greatly enhanced activity for thrombin inhibition (Table 7) with an approximately 5-fold reduction of $K_i$ (about 28 nM) as compared to MH2-wZIP4 ($K_i$ about 150 nM) and about 13 fold as compared to BRI-T207 ($K_i$ about 400 nM). Similarly to hirulog-1 (i.e. bivalirudin) and related bivalent thrombin inhibitors (Maraganore 1990; DiMaio 1990), BRI-T208 is also sensitive to thrombin cleavage (FIG. 15), releasing the (d)FPR moiety from the N-terminal segment and a potentially bivalent inhibitor product BRI-T110 (SEQ ID NO: 46). This analog of MH2-wZIP4 is essentially BRI-T109 (Table 6), except for the missing Gln residue at the C-terminus. Potent inhibitory activity of BRI-T110 can be restored by substituting the Pro residue of the first position by an Ile as in BRI-T111 (Table 6). The residue "p1" in "p1"-RFTD (SEQ ID NO: 72) can also be selected to achieve the desired rate of cleavage at the (d)FPR-"p1" RFTD junction (SEQ ID NO: 73) (Maraganore 1990; DiMaio 1990) of composite molecules of the following formula:

```
                                              (SEQ ID NO: 74)
(d)FPR-"p1"RFTDGEWTWDDATKTWTWTEGDFEEIPEEYL
```

The choice of a suitable residue in the "p1" position is further restricted according to the strong preference for hydrophobic residues, i.e. Ile, Val, Leu or Phe at this position of hirudin for binding to the thrombin active site (Wallace 1989).

```
                                              (SEQ ID NO: 55)
(d)FPR-PRFTDGEWTWDDATKTWTWTE-GDFEEIPEEYL
(BRI-T208)

(SEQ ID NO: 56)
(d)FPR-IRFTDGEWTWDDATKIWTWTE-GDFEEIPEEYL
(BRI-T218)

(SEQ ID NO: 57)
(d)FPR-VRFTDGEWTWDDATKTWTWTE-GDFEEIPEEYL
(BRI-T228)

(SEQ ID NO: 58)
(d)FPR-LRFTDGEWTWDDATKTWTWTE-GDFEEIPEEYL
(BRI-T238)

(SEQ ID NO: 59)
(d)FPR-FRFTDGEWTWDDATKTWTWTE-GDFEEIPEEYL
(BRI-T248)
```

BRI-T218 and BRI-T228 are the most important of this series, as BRI-T218 releases BRI-T111 (a direct analog of MH2-wZIP4) after thrombin cleavage at the (d)FPR-IRFTD junction (SEQ ID NO: 73 where "p1" is I) and BRI-T228 contains a variant of MH2-wZIP4 with a naturally-occurring Val1 residue at this position of hirudin. Very importantly, BRI-T218 itself exhibits a significantly enhanced thrombin inhibitory activity, with a $K_i$ of about 14 nM (FIG. 14 Panel D), which apparently is a result of the extended linker IRFTD-GEWTWDDATKTWTWTE (SEQ ID NO: 75), bridging the (d)-Phe-Pro-Arg moiety inhibiting the thrombin active site and the sequence segment GDFEEIPEEYL (SEQ ID NO: 25) specific for the fibrinogen-recognition exosite of thrombin.

Figure 15B:
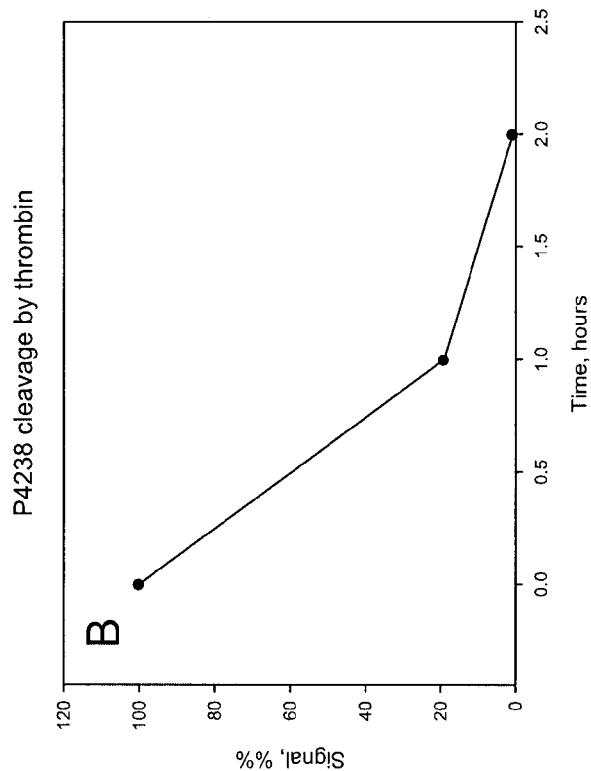
FIG. 15B shows a much faster rate of cleavage for the BRI-T218 (i.e. P4238) peptide, reaching almost completion of the cleavage reaction after 2 hours of incubation.
Figure 15A:
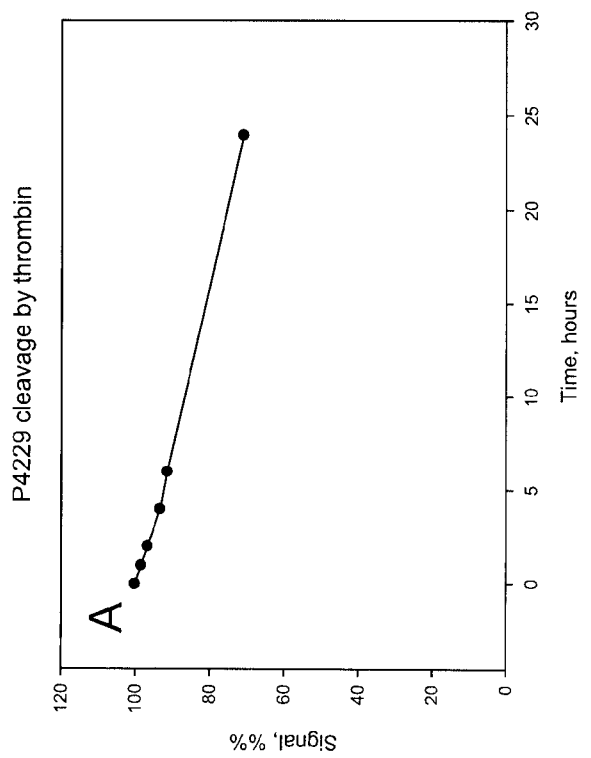
FIG. 15A illustrates the cleavage of peptide BRI-T208 (i.e. P4229) by thrombin, as followed by the quantitation of HPLC elution profile of the intact peptide. The percentage of the uncleaved peptide was determined from the peak area of the elution profile for the full-length peptide.

FIG. 15 compares the cleavage rates of BRI-T208 (with the substrate sequence (d)FPR-PRFTD . . . ) and BRI-T218 (with (d)FPR-IRFTD . . . ). The decrease of the peak intensities of the parent (or intact) peptide is accompanied by the increased intensities of cleavage products identified by mass spectrometry as having the sequences of PRFTD-GEWTWDDATKTWTWTE-GDFEEIPEEYL for BRI-T208 (from SEQ ID NO: 55) and IRFTD-GEWTWDDAT-KTWTWTE-GDFEEIPEEYL for BRI-T218 (from SEQ ID NO: 56), respectively, showing specific proteolysis catalyzed by thrombin at the expected peptide bonds. On the other hand, BRI-T208 is significantly more resistant to thrombin cleavage than BRI-T218, which is completely converted to the cleavage products within two hours under the specific experimental conditions (FIG. 15). Such fast cleavage for BRI-T218 by thrombin mirrors the time dependence of the inhibitory activity observed for BRI-T218 on thrombin-catalyzed cleavage of chromogenic substrates (FIG. 14 Panel D).

Figure 16:
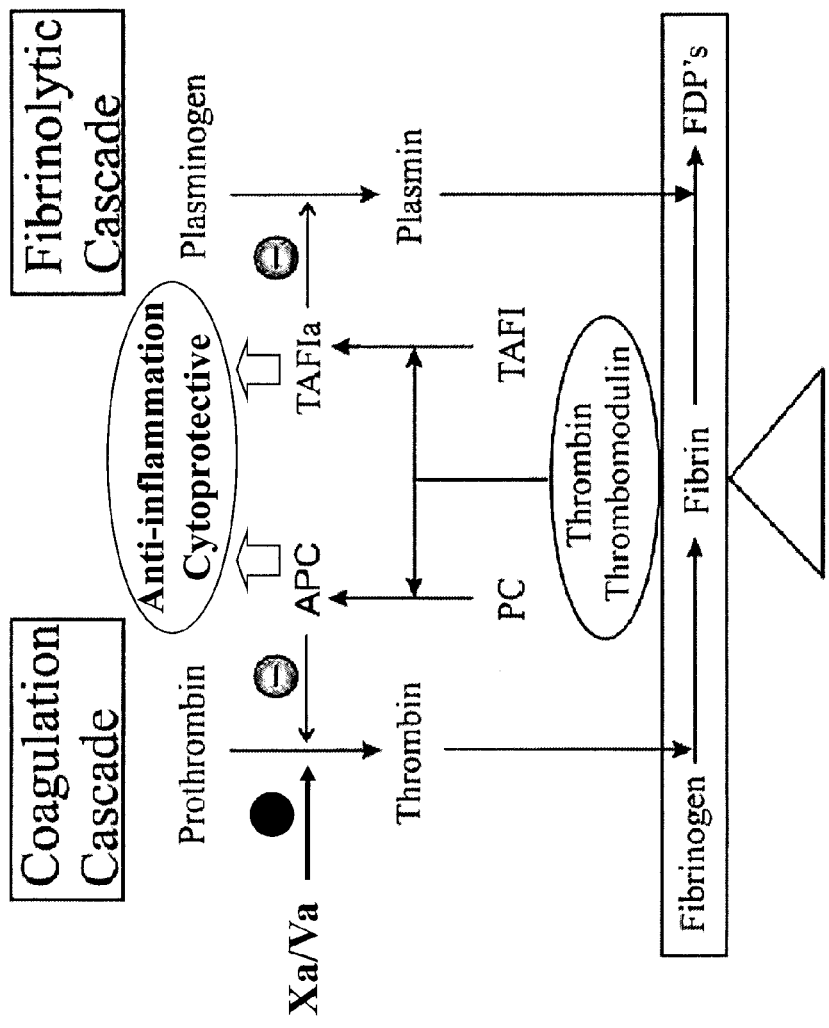
FIG. 16 depicts a diagram (adapted from Nesheim 2003) showing the plethora of regulatory functions of thrombin including procoagulant, anti-coagulant and anti-inflammatory activities (Asai 2004; Nishimura 2007). In addition to the thrombin-thrombomodulin complex, prothrombin activation also generates a membrane-bound form of thrombin, the meizo-thrombin, which acts as potent activator of protein C (Hackeng 1996).

Example 10: Heat-Activatable Thrombin Inhibitors Constructed from Other Thrombin-Binding Motifs All peptides of this invention, especially those of the BTI and MH2-series (Table 1) can be modified by substituting the C-terminal residues GDFEEIPEEYLQ (SEQ ID NO: 8) with other peptides that bind to exosites on thrombin other than the active site. One example of these modifications is to replace DFEEIPEEYLQ (from SEQ ID NO: 8) by the corresponding sequence EFEEFEIDEEEK (SEQ ID NO: 76) from haemadin, a thrombin specific inhibitor from Indian leeches (Corral-Rodriguez 2010). The resulting thrombin inhibitor is referred to as BRI-T304 (Table 6), which in essence is a minimized version of the naturally occurring haemadin. Similar to the MH2-series of bivalent thrombin inhibitors, especially MH2-wZIP4, BRI-T304 has the hairpin-forming trpzip4 sequence (Cochran 2001) replacing the globular domain of haemadin (Richardson 2000) in linking the IRFTD (SEQ ID NO: 7) segment for binding and inhibiting the active site of thrombin and with the acidic tail sequence EFEEFEIDEEEK (SEQ ID NO: 76) targeting the anion-binding/heparin-binding exosite II on thrombin (Warkentin 2004). Since haemadin and its C-terminal segment do not compete with thrombin binding to thrombomodulin, BRI-T304 is expected to confer an enhanced anticoagulant activity by not interfering with the natural anticoagulant and anti-inflammatory activities of thrombin expressed by the thrombin-thrombomodulin complex (FIG. 16). Most importantly, BRI-T304 would not inhibit the membrane-bound and innate anticoagulant form of thrombin, the meizo-thrombin (Hackeng 1996), thereby having the ability to reduce only the procoagulant free thrombin generated at sites of pathogenic blood coagulation (Wood 2011). The hirudin mimetic MH2-wZIP4 would also function favorably in tipping the haemostatic balance toward anticoagulation (Nesheim 2003 and FIG. 16), since by design its greatly-reduced binding affinity for thrombin (Table 4) would make it an ineffective inhibitor of meizo-thrombin as compared to hirudin (Fisher 1998).

In general, the 22-residue polypeptide IRFTD$_5$GEWTW$_{10}$DDATK$_{15}$TWTWT$_{20}$EG (SEQ ID NO: 81), which is the amino-terminal portion of MH2-wZIP4, can also be conjugated to protein ligands of thrombin via N-terminal extensions, as, for example, in the following covalent conjugate:

```
                                              (SEQ ID NO: 79)
IRFTDGEWTWDDATKTWTWTE-GGS-[VH-PEPA1] (BRI-T404)
```

Here, VH-PEPA1 is an antibody VH domain binder of thrombin discovered through panning phage-display VH libraries (Tanha 2006) against human thrombin blocked at the active site by (d)Phe-Pro-Arg-chloromethyl ketone (or PPACK) (Ng 2005).

The following is a list of primers for construction of this protein-based thrombin inhibitor:

```
Forward-primer for the first PCR reaction:
                                              (SEQ ID NO: 84)
5'-acc tgg acc gaa ggc ggc agc gat gtc cag ctg cag
gcg tct Reverse-primer for the first PCR reaction:
                                              (SEQ ID NO: 85)
5'-aat cgg ctc gag tga gga gac gg tga cct g Forward-primer for the second PCR reaction:
                                              (SEQ ID NO: 86)
5'-gcc cag ccg gcg atg gcc att cgt ttt act gat ggc
gaa tgg acc tgg gat gat gcc acc aaa acc tgg acc
tgg acc gaa
```

-continued

```
Reverse-primer for the second PCR reaction:
                                    (SEQ ID NO: 87)
5'-aat cgg ctc gag tga gga gac gg tga cct g
```

Figure 17:
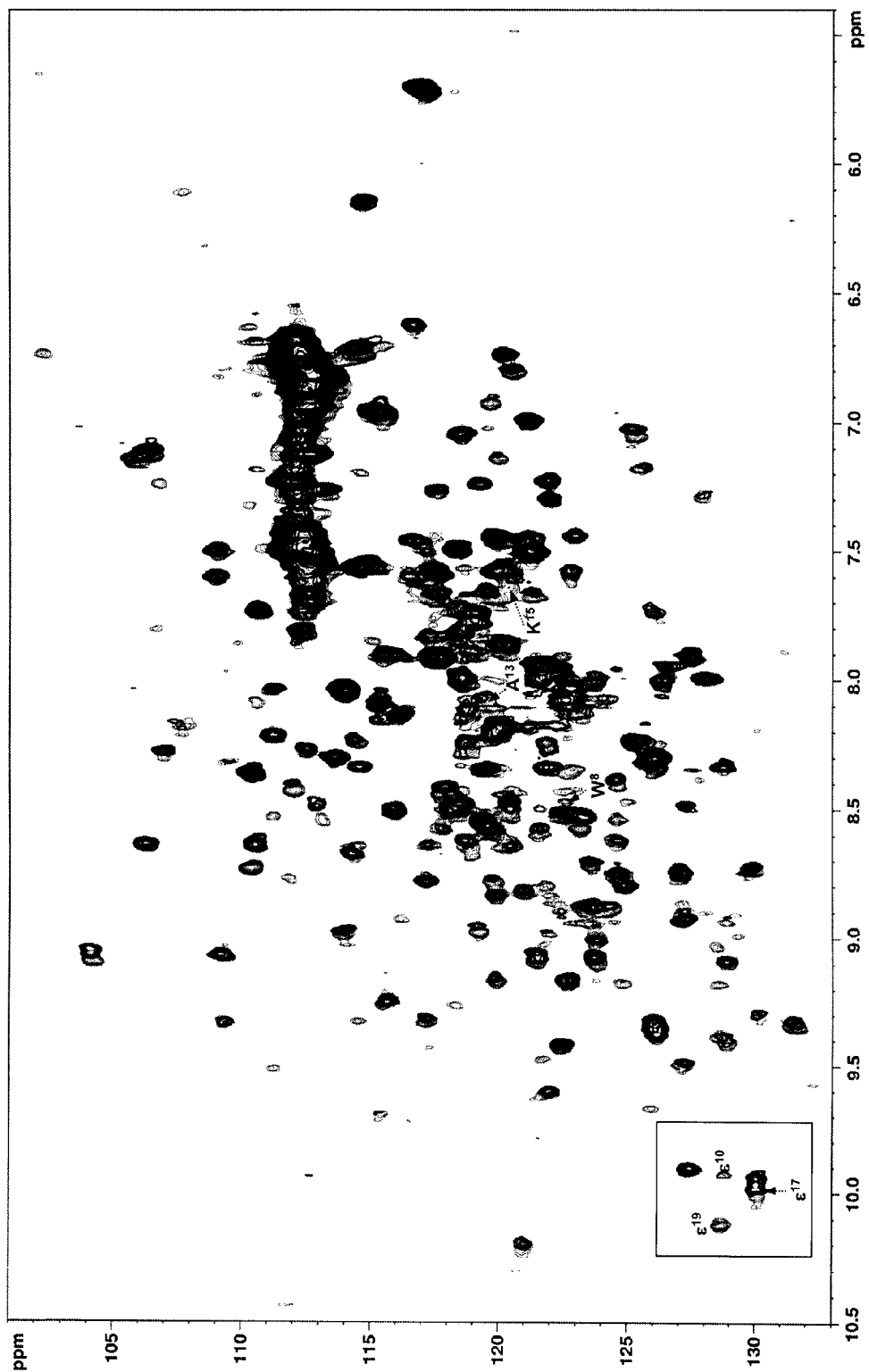
FIG. 17 shows the collagen-responsive property of BRI-T404, a protein-based bivalent thrombin inhibitor constructed from linking the IRFTD (SEQ ID NO:7) sequence by the trpzip4 linker to a thrombin-binding antibody VH domain, PEPA 1. The (H, $^{15}$N)-HSQC spectrum in thin gray contours is that of the $^{15}$N-labelled free protein BRI-T404 in 200 mM Tris-HCl/200 mM NaCl at pH 7.6 at a temperature of 298 K. The darker (thick black) plots are the (H, $^{15}$N)-HSQC cross peaks of $^{15}$N-labelled BRI-T 404 in the presence of collagen prepared similarly as for experiments with $^{15}$N-MH2-wZIP4 (FIG. 10). The rectangular box shows the locations of the characteristic side-chain resonances expected for the Trp residues in the trpzip4 linker (FIG. 10A, left panel and FIG. 12A). Also clearly discernable are the backbone amide (H, $^{15}$N)-HSQC cross peaks of residues W8, A13 and K15 in the trpzip4 region of $^{15}$N-labelled BRI-T404.

Recombinant BRI-T404 with uniform labeling of the $^{15}$N isotope allowed the identification of the four Trp residues (FIG. 17) unique to the trpzip4 linker region (FIG. 12, Panel A). These Trp residues responded to the presence of collagen hydrogels (FIG. 17) and, practically all residues of the PEPA1 portion of BRI-T404 are unaltered similarly to the exposure of the C-terminal sequence of MH2-wZIP4 in the presence of collagen (FIG. 10 and FIG. 12). Therefore, the trpzip4 moiety preserves its collagen-binding property as identified with both the MH2-wZIP4 and trpzip4-NH2 peptides (FIG. 11 and FIG. 13), illustrating its use for the construction of protein-based bivalent thrombin inhibitors.

Figure 13:
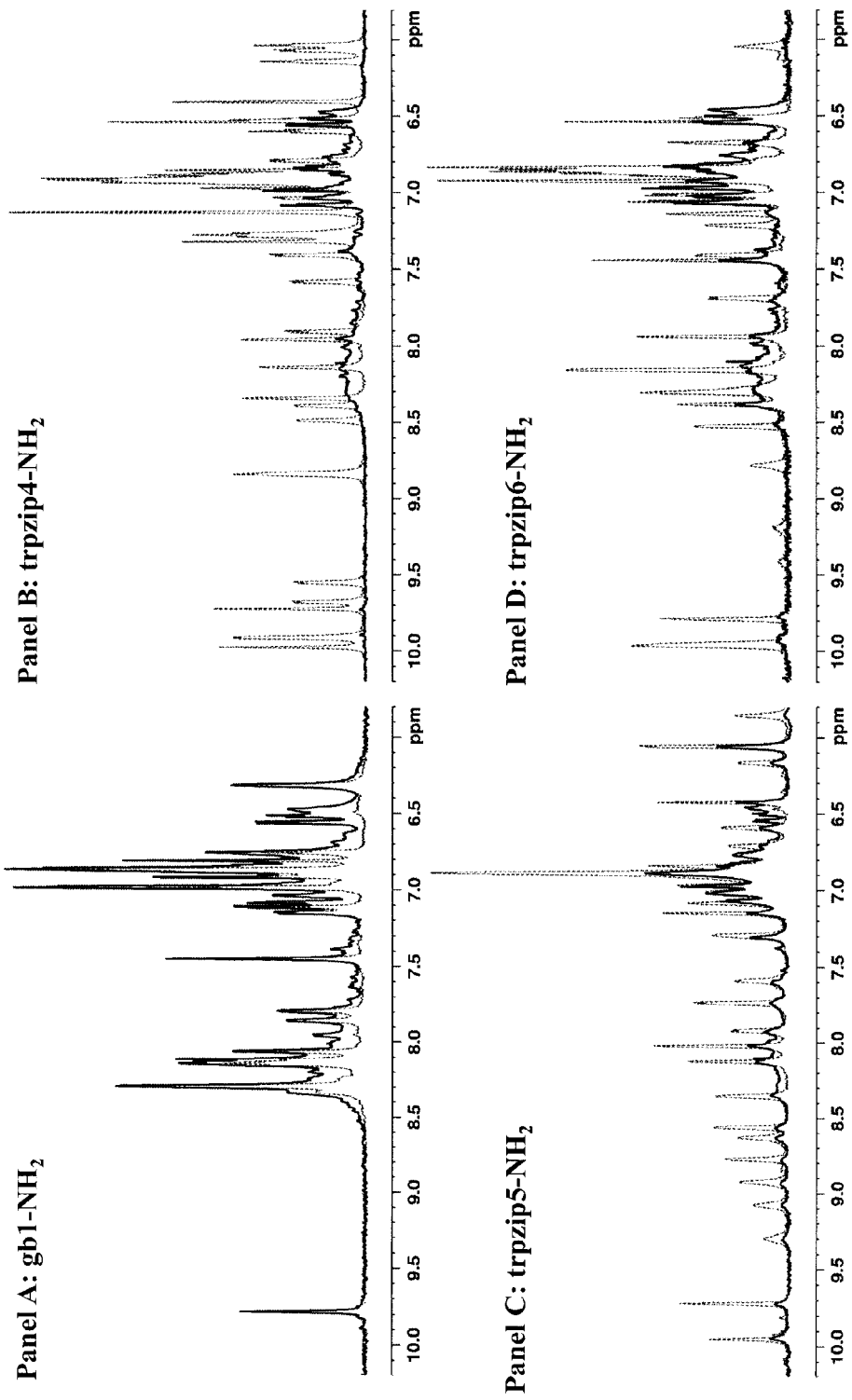
FIG. 13 compares the one-dimensional proton NMR spectra of the linker peptides GEWTYDDATKTFTVTE (SEQ ID NO: 2 or gb1), GEWTWDDATKTWTVTE (SEQ ID NO: or trpzip6), GEWTYDDATKTFTWTE (SEQ ID NO: 4 or trpzip5) and GEWTWDDATKTWTWTE (SEQ ID NO: 5 or trpzip4) in a PBS (phosphate-buffered saline) solution (gray dotted lines) supplemented with 50 mM sodium phosphate with the sample pH adjusted to 7.4 and in collagen hydrogels (thick black lines) formed in the presence of the respective peptides. All samples were prepared by mixing the respective peptides with collagen followed by collagen gelation under magnetic field guidance (Ma, 2008). Proton NMR spectra were nearly identical for gb1-$NH_2$ and trpzip4-$NH_2$ before and after collagen gelation, while significant resonance sharpening toward those of the free peptide was observed for trpzip5-$NH_2$ and trpzip6-$NH_2$ after collagen gelation, especially for the Trp sidechain resonances, i.e. those between 9.5 and 10 ppm.
Figure 18:
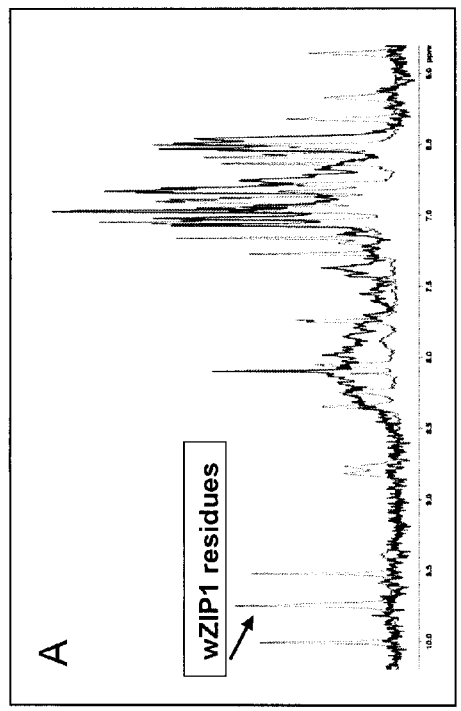
FIG. 18 illustrates the collagen-binding property of the trpzip1-NH2 peptide and the thrombin-inhibitory activities of two MH2-related peptides constructed using the trpzip1 sequence as the linker.
Figure 18:
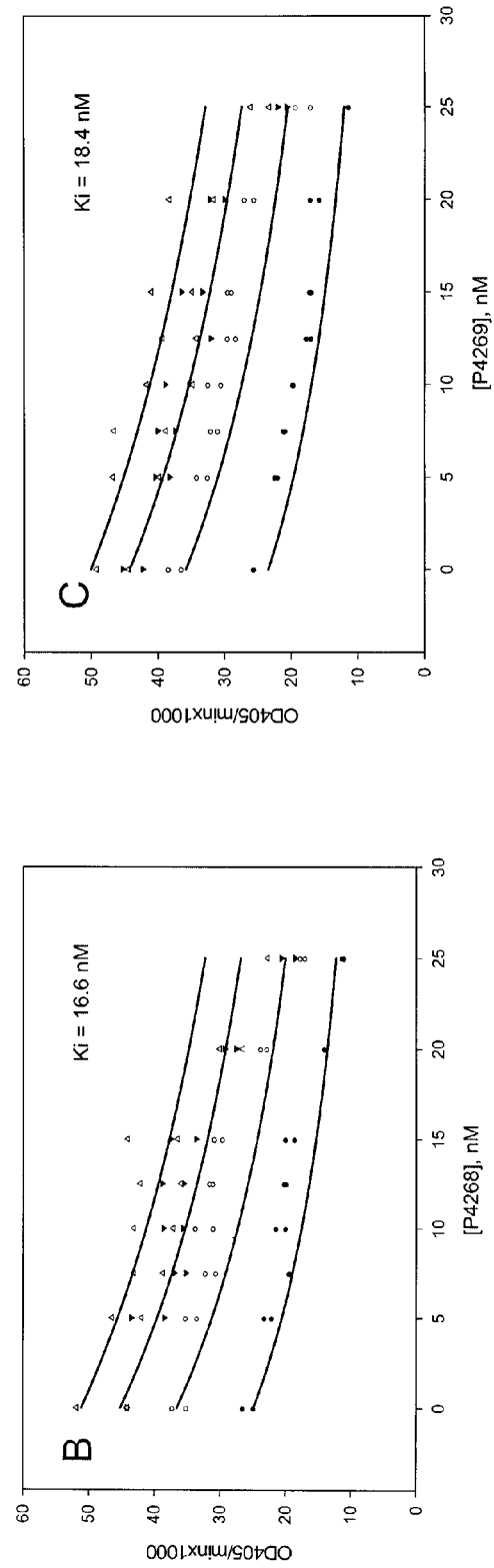

Thrombin-binding moieties, e.g. the IRFTDG sequence (SEQ ID NO: 29) and the hirudin sequence GDFEEIPEEYLQ (SEQ ID NO: 8) or the haemadin sequence EFEEFEIDEEEK (SEQ ID NO: 76) can also be linked by other heat-activatable sequences, especially those belonging to the general family of hairpin-forming motifs or trpzip peptides (Cochran 2001). Peptide trpzip1-NH$_2$ having the sequence of SWTWEGNKWTWK (SEQ ID NO: 21) has a similar behavior of conformational changes and/or binding with collagen hydrogels (FIG. 18A) as those of the trpzip4, trpzip5 and trpzip6 peptides (FIG. 13). FIG. 18B and FIG. 18C demonstrate the strong thrombin-inhibitory activities for MH2-wZIP1 (SEQ ID NO: 83) and MH2-wZIP1-2G (SEQ ID NO: 82) (Table 7) constructed from the IRFTDG (SEQ ID NO: 29) and GDFEEIPEEYLQ (SEQ ID NO: 8) sequences. Therefore, the shorter 12-residue hairpin peptides (SEQ ID NO: 20), especially trpzip1 (SEQ ID NO: 21), trpzip2 (SEQ ID NO: 23) and trpzip3 (SEQ ID NO: 24), have the same folding/unfolding properties required for the construction of locally-active thrombin inhibitors specific to inflamed tissues.

In all, new thrombin inhibitors can be constructed using heat-activatable linkers of this invention with the view of reducing selectively the pro-coagulant and pro-inflammatory actions of thrombin while preserving the anti-coagulant and anti-inflammatory forms in complex with thrombomodulin (FIG. 16). In this regard, there is a vicious circle linking tissue inflammation, primarily in the form of collagen de-structurization (Sukhova 1999; Penz 2005; Tan 2008; Adiguzel 2009; Eckly 2011), to platelet activation (Penz 2005; Reininger 2010; Adiguzel 2009; Bollard 2010) and to the activation of the blood coagulation cascade and the precipitous generation of pro-coagulant and pro-inflammatory thrombin (Reininger 2010, Wood 2011). It has been shown that this vicious circle may be interrupted in a variety of inflammatory conditions either by direct thrombin inhibition, as in the case of pulmonary fibrosis (Bogatkevich 2011) or by augmenting the anti-coagulant and anti-inflammatory forms of thrombin, as demonstrated for the inflammatory joint disease (Flick 2011). Heat-activatable thrombin inhibitors of this invention are therefore expected to be particularly efficacious for curbing local inflammation without tipping the haemostatic balance (FIG. 16) toward systemic anticoagulation and leading to potential bleeding complications.

Example 11: In-Vivo Experiments Using Rat Models of Venous and Arterial Thrombosis Male Sprague-Dawley rats (250-310 g; Charles River Laboratories, St-Constant, QC, Canada) were acclimated for at least 3 days prior to the start of the study. Animals were housed in microisolator cages and were kept on a 12-hr light/dark cycle with constant temperature and humidity. Food and water were provided ad libitum. Various antithrombotic agents and peptides of this invention were dissolved in saline (0.9% sodium chloride) prior to use.

The FeCl$_3$-induced venous model of thrombosis in rats was generated as described by Wang and Xu (Wang 2005) with some modifications (Couture 2011). Briefly, rats were anesthetized with a 2.5% isoflurane/oxygen mixture and placed on a heat source (35-37° C.). The vena cava was then exposed via a midline incision and the region between the renal and iliolumbar veins was isolated. Saline (N=20, where N is the number of rats), heparin (130 U/kg; N=8), argatroban (4.5 mg/kg; N=6) or bivalirudin (1.3 mg/kg; N=4) and peptides of this invention were then administered intravenously (2.8 mL/kg) via a catheter placed in the tail vein. One minute after drug administration, a piece of filter paper (Gel Blot Paper, GB003, Whatman, Piscataway, N.J., USA; 7 mm diameter) saturated with 10% FeCl$_3$ (EMD Chemicals Inc., Gibbstown, N.J., USA) was placed on the exposed surface of the vena cava and incubated for 3.5 minutes. During the application of FeCl$_3$, the abdominal region was covered with aluminum foil. At the end of the incubation period, the filter paper was removed and the exposed viscera covered with a saline-soaked gauze. Sixty minutes after the initial application of FeCl$_3$, a blood sample was collected via cardiac puncture using sodium citrate tubes. The vena cava was dissected and the thrombus removed and weighed. Preparing and processing each animal took approximately 1 hr and therefore 7 animals were treated each day. Control animals were always included when the other treatments were being administered. For this reason, the number of animals in the control group is higher than that of the treated-groups.

The FeCl$_3$-induced arterial model of thrombosis in rats was also generated as described by Wang and Xu (Wang 2005) with some modifications (Couture 2011). Briefly, rats were anesthetized with a 2.5% isoflurane/oxygen mixture and placed on a heat source (35-37° C.). An incision was made over the right carotid artery, and a segment of the artery was exposed via blunt dissection. A Doppler flow probe (Model MA1PRB, Transonic System Inc., Ithaca, N.Y., USA) connected to a perivascular flow module (TS420, Transonic System Inc., Ithaca, N.Y., USA) was then attached to the carotid artery to monitor blood flow. Data were collected and analyzed using the MP100 Biopac™ Systems (Biopac Systems, Santa Barbara, Calif., USA), and the AcgKnowledge™ software (Biopac Systems, Santa Barbara, Calif., USA), respectively. Baseline blood flow was recorded for a minimum of 15 minutes until readings stabilized. Aquasonic 100 gel (Parker Laboratories, Inc., Fairfield, N.J., USA) was added to help conductivity and any fluid accumulating at the site of surgery was removed during data sampling without touching the probe. Saline (N=10), heparin (130 U/kg; N=4), argatroban (4.5 mg/kg; N=4), bivalirudin (1.3 mg/kg; N=3) or peptides of this invention were administered intravenously (2.8 mL/kg) via a catheter placed in the tail vein. One minute after drug administration, a piece of filter paper (Gel Blot Paper, GB003, Whatman, Piscataway, N.J., USA; 7 mm diameter) saturated with 20% FeCl$_3$ (EMD Chemicals Inc., Gibbstown, N.J., USA) was placed on the exposed surface of the carotid artery and incubated for 3.5 minutes. During the application of FeCl$_3$, the neck region was covered with aluminum foil. At the end of the incubation period, the filter paper was removed and the exposed carotid was covered with a saline-soaked gauze.

Time to occlusion was defined as the time from the application of $FeCl_3$ until blood flow decreased to zero. Time to occlusion was recorded as 60 minutes if the vessel did not occlude by this time. Preparing and processing each animal took approximately 1 hr and 7 animals were treated each day. Control animals were always included when the other treatments were being administered. For this reason, the number of animals in the control group is higher than that of the treated-groups.

Protein content of the thrombus was also measured according to protocol by Wang (Wang 2005). Cleaned thrombus was digested for 16 hrs at 50° C. in 200 µl of 100 mM Tris, pH 7.5 containing 400 µg proteinase K (Invitrogen). Contents of amino acids and small peptides were measured at $OD_{280}$ with digestion buffer used as a blank. Protein contents of the thrombus were found to parallel the dry weights of the thrombus (Conture 2011), hence thrombus weights were used for routine measurements.

Terminal blood samples were analyzed for aPTT within 15 to 30 minutes of collection using a Coag DX Analyzer with aPTT citrate cartridges (IDEXX Laboratories, Westbrook, Me., USA).

Statistical analysis was conducted using GraphPad™ Prism (GraphPad Software Inc., San Diego Calif., USA). Data were analyzed using one-way ANOVA with post-hoc Bonferroni correction for multiple comparisons. The relationship between thrombus weight and thrombus volume was determined by linear regression. All data are given as mean±standard error of the mean (SEM). Statistical significance was set at $p \leq 0.05$, in other words, the efficacy of a drug is significantly higher if $p \leq 0.05$ when comparing the drug-treated group with those administered only with the saline vehicle.

Figure 19:
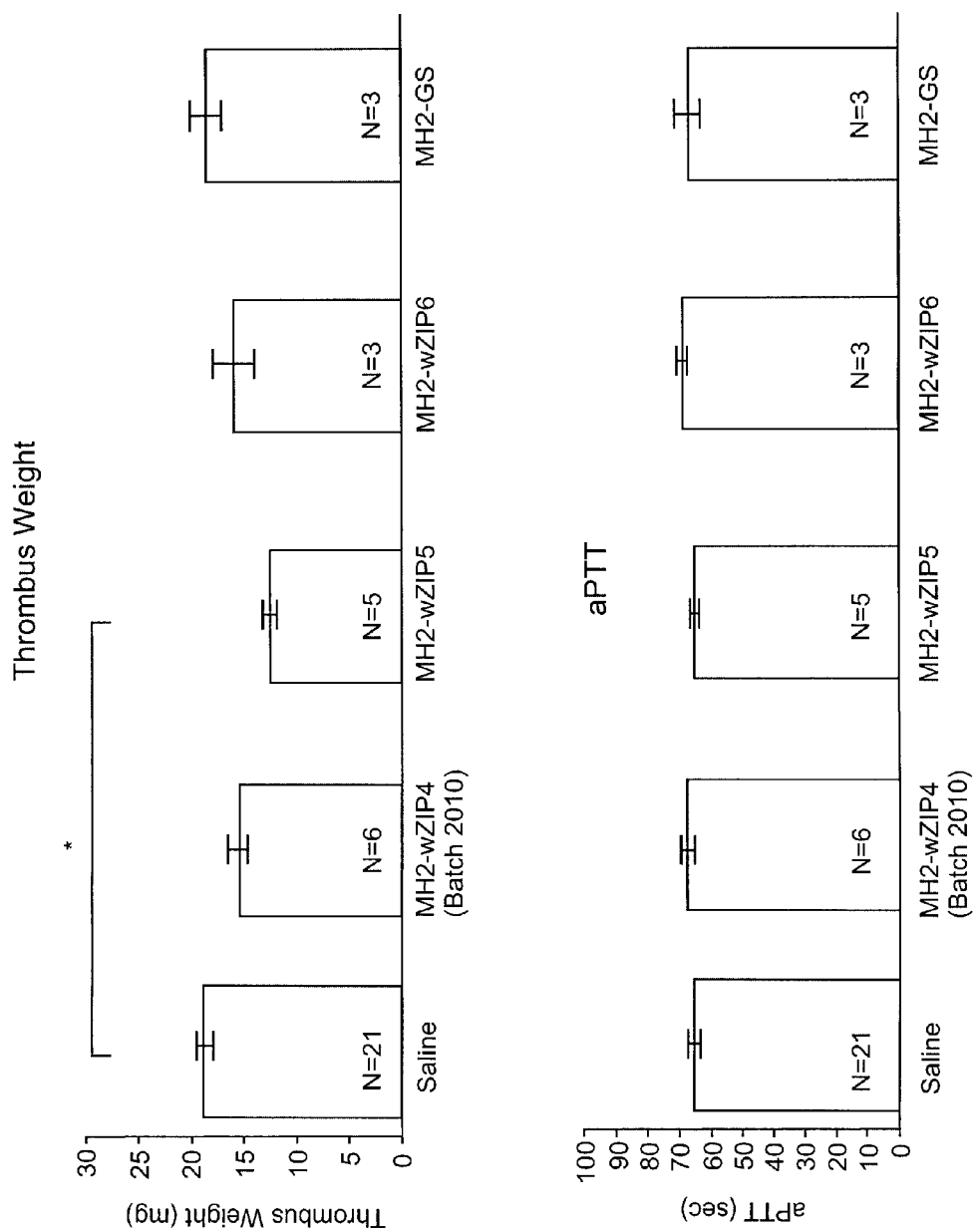
FIG. 19 illustrates in-vivo activities of the MH2-wZIP series of thrombin inhibitors administered through single-bolus injections (via the rat tail vein) in a rat model of venous thrombosis. Sizes of the locally-accumulated thrombus in vena cava were quantitated through the measurement of the protein content and/or the weights of dissected thrombus, which show linear correlations (Couture 2011). Only the thrombus weights are shown here as the measure of in-vivo efficacy of each thrombin inhibitor with the same dosage level of 0.22 mg/kg (see also FIG. 20). Clotting times (aPTT) were determined for fresh blood withdrawn from the rats at 60 minutes after injection of the vehicle or the respective thrombin inhibitors.
Figure 20A:
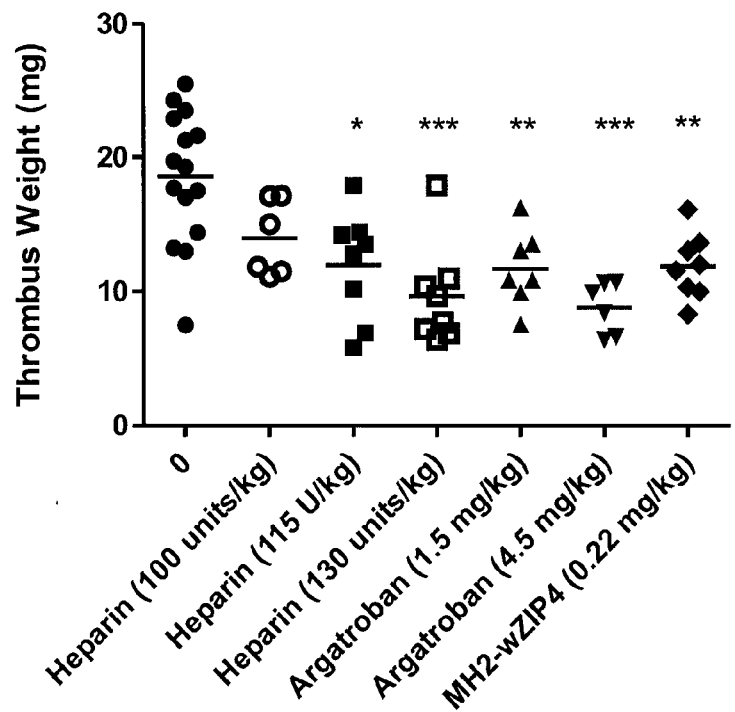
FIG. 20A and FIG. 20B illustrate the in-vivo efficacies of a number of thrombin inhibitors administered at the respective dosage levels through single-bolus injections in a rat model of venous thrombosis. * is $p<0.001$,  is $p<0.01$ and * is $p<0.05$, when comparing with the control (saline) group by one-way ANOVA with post-hoc Bonferroni corrections for multiple comparisons.
Figure 20B:
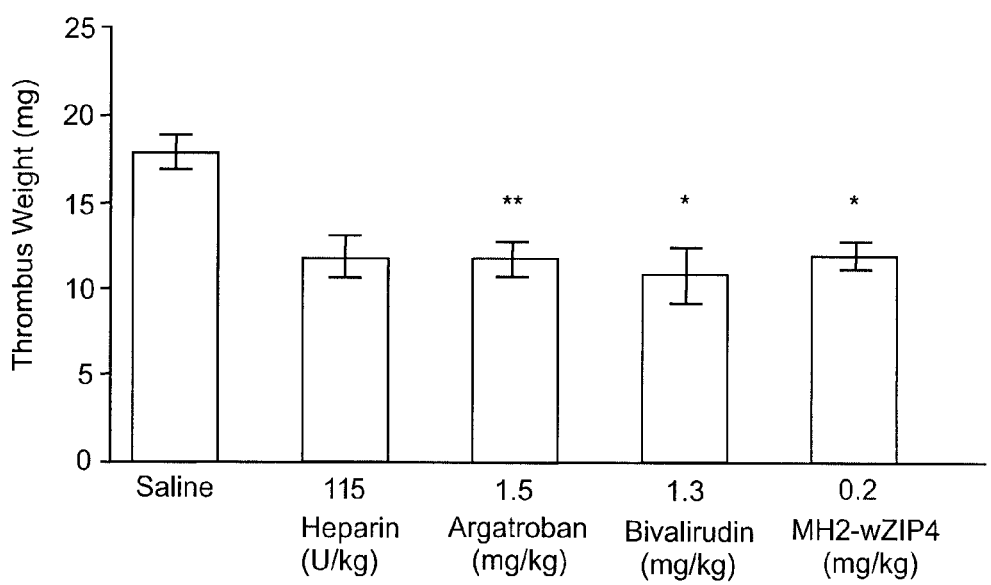
Figure 21:
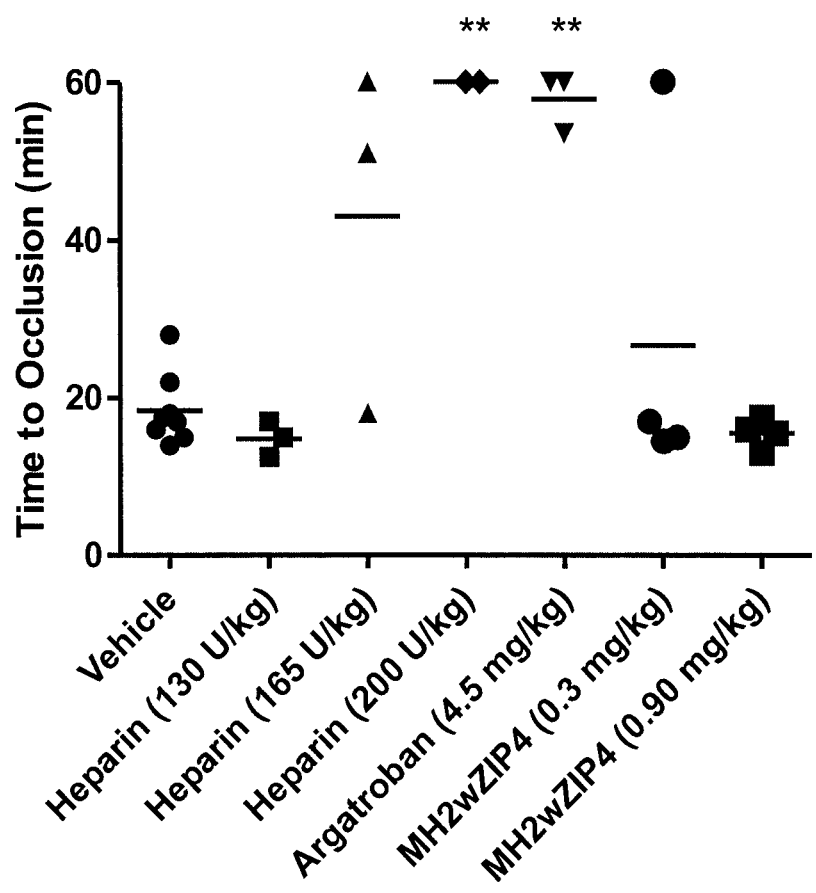
FIG. 21 illustrates a comparison of in-vivo efficacy of thrombin inhibitors administered through a single-bolus injection in a rat model of arterial thrombosis. The horizontal axis indicates the dosage level of each administered compound. * is $p<0.001$,  is $p<0.01$ and * is $p<0.05$, when comparing with the control (saline) group by one-way ANOVA with post-hoc Bonferroni corrections for multiple comparisons.
Figure 22:
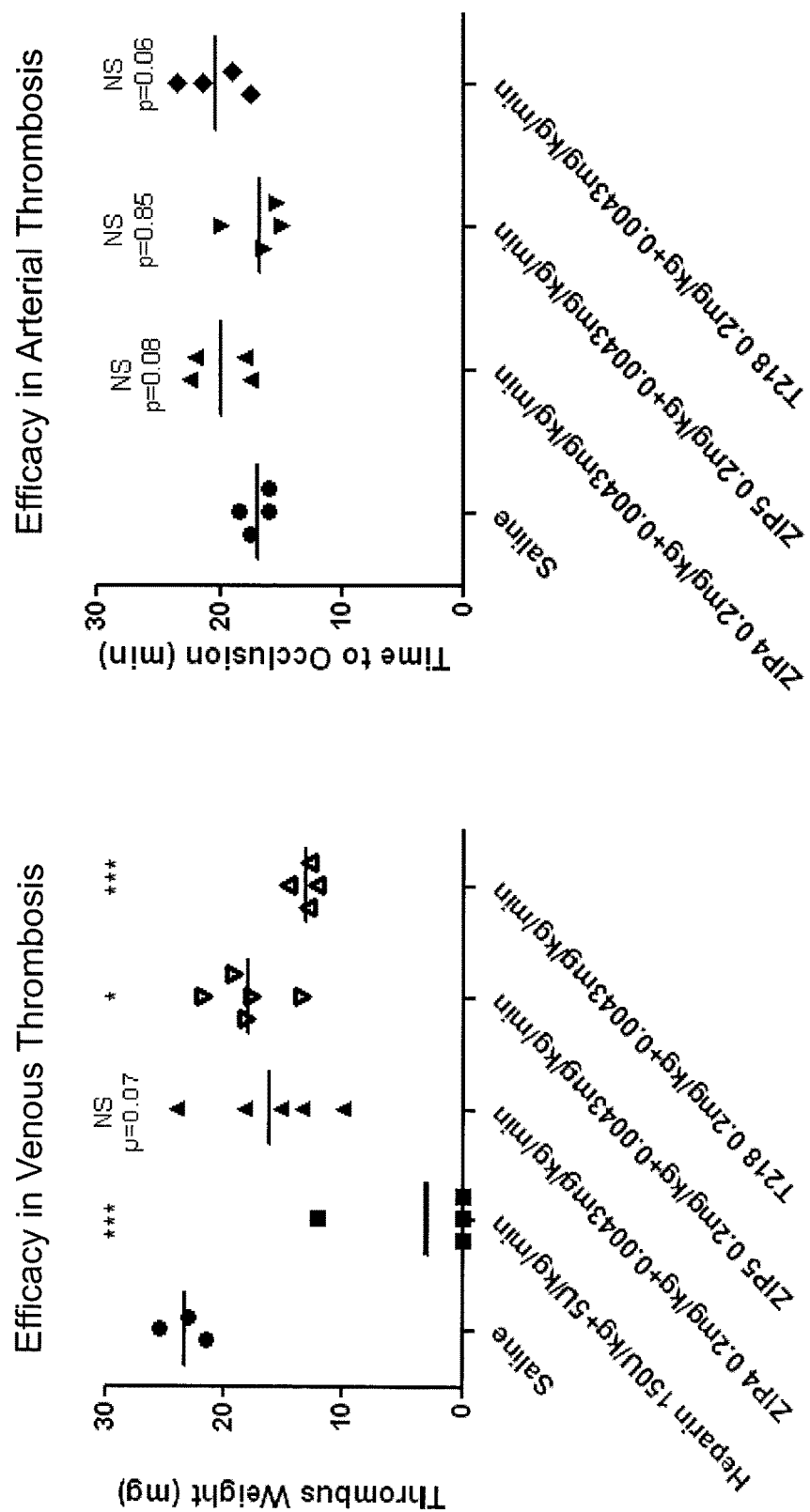
FIG. 22 illustrates the in-vivo efficacies of MH2-wZIP4, MH2-wZIP5 and BRI-T218 combining a single-bolus injection with maintenance infusion in rat models of venous (left) and arterial thrombosis (right). *** is $p<0.001$ and * is $p<0.05$, when comparing with the control (saline) group by one-way ANOVA with post-hoc Bonferroni corrections for multiple comparisons. MH2-wZIP4, MH2-wZIP5 and BRI-T218 are designated as ZIP4, ZIP5 and T218, respectively, in the data plots. All compounds were administered 1 min before application of FeCl$_3$ to the respective blood vessels with a single bolus followed immediately by constant infusion at the indicated dosage levels. Compound infusion was maintained throughout the 60-minute period following vessel injury by FeCl$_3$ applications. Dosage levels for MH2-wZIP4, MH2-wZIP5 and BRI-T218 were 0.2 mg/kg for the single-bolus injection and 0.00433 mg/kg/min for the maintenance infusion.

Results obtained from the rat models of venous and arterial thrombosis are shown in FIG. 19 (venous model), FIG. 20 (venous model), FIG. 21 (arterial model). MH2-wZIP4 is particularly efficacious in reducing the weight of local thrombus formation in the venous model of thrombosis. FIG. 19 demonstrates that the anti-thrombotic properties of the related MH2-wZIP5 are comparable to MH2-wZIP4 in vivo in the venous thrombosis model. FIG. 20A and FIG. 20B further demonstrate that the compound MH2-wZIP4 is more effective than other anti-thrombotic agents (heparin, argatroban and bivalirudin) in the venous thrombosis model, despite the fact that bivalirudin is a much better thrombin inhibitor (see Table 5). In contrast, studies with the rat arterial thrombosis model (FIG. 20) showed a consistently better efficacy for bivalirudin in reducing arterial occlusion as well as for argatroban, which is in exact parallel with the increased activities of bivalirudin and argatroban for thrombin inhibition (Table 2 and Table 5). When the thrombin-inhibitory activity is increased, (FIG. 14 and Table 7), compound BRI-T218 appears to restore the anti-thrombotic activity in the arterial model of thrombosis (FIG. 22). Supplementation of the single bolus injections (through the tail vein) with drug infusion increases the efficacy of both MH2-wZIP4 and BRI-T218 in the arterial model of thrombosis as compared with only single-bolus injections (FIG. 21).

Figure 23:
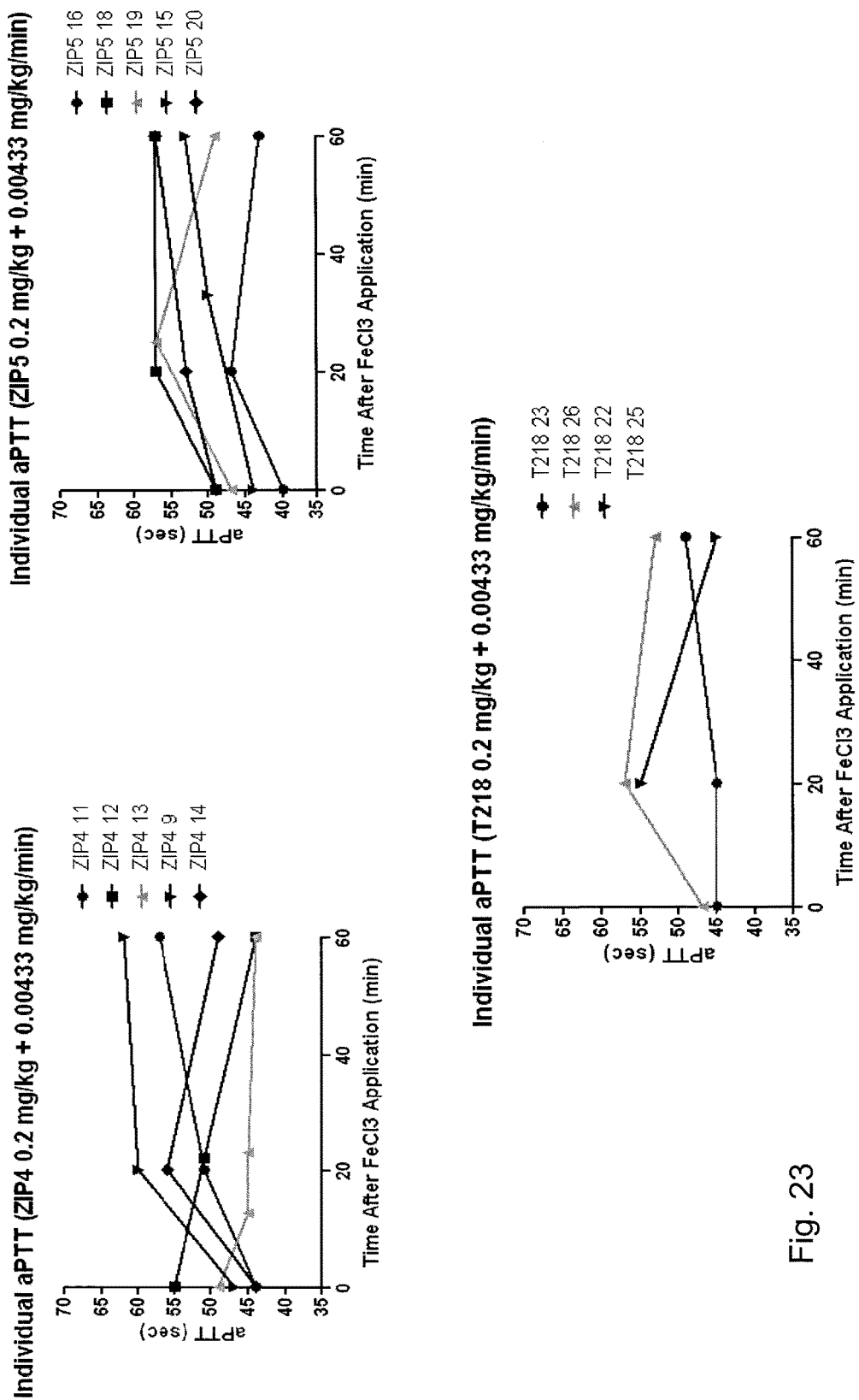
FIG. 23 illustrates the clotting times (aPTT) determined for fresh blood withdrawn from rats with venous thrombosis at three time points, the first before drug administration and vessel injury, the second at 20 minutes after FeCl$_3$ application and the third 60 minutes following injection of the respective thrombin inhibitors. Clotting times (aPTT) are shown for different rats administered with each thrombin inhibitor, ZIP4 for MH2-wZIP4, ZIP5 for MH2-wZIP5 and T218 for BRI-T218. Dosage levels for every compound were 0.2 mg/kg for the single-bolus injection and 0.00433 mg/kg/min for the maintenance infusion.

FIG. 23 illustrates more clearly the lack of strong anticoagulant effects at the systemic level for thrombin inhibitors of the present invention, especially MH2-wZIP4, mH2-wZIP5 and BRI-T218. Here, clotting times (aPTT) were determined for fresh blood withdrawn from rats with venous thrombosis at two more time points in addition to the single time point at the end of the procedure (FIG. 19). There is generally only a slight prolongation of the clotting time (aPTT) for all three thrombin inhibitors, MH2-wZIP4, MH2-wZIP5 and BRI-T218 (FIG. 23) when comparing the clotting times 20 minutes after compound administration with the respective clotting times for normal blood collected from each rat before the procedure. Most importantly, all the clotting times are within the limits of those for rats in the (saline) control group (FIG. 19), indicating the unique characteristics of thrombin inhibitors of the present invention. Collectively, the in-vivo data shows that thrombin inhibitors of the present invention have desired local anticoagulant and anti-thrombotic properties with potential applications in wider therapeutic indications while free from bleeding side effects.

Example 12: Collagen-Induced Arthritis (CIA) Assay

The collagen-induced arthritis (CIA) model is used to determine the effect of bivalent thrombin inhibitors of the present invention on arthritis, similarly to the evaluation of the thrombin inhibitor hirudin in the treatment of arthritis (Marty 2001).

Briefly, male DBA/1J mice between 8 and 10 weeks of age (Charles River Labs) are acclimated under standard light and temperature conditions with food and water ad libitum for 1 week. Twelve mice are randomly assigned to a test group, twelve randomly assigned to an antigen (collagen)-only group and twelve randomly assigned to a no-antigen group. The mice are weighed to determine the average body weight of each group, and ankles and paws (maximal lateral) are evaluated to establish baseline measurements.

On day 1, lightly anesthetized mice in the test group and the collagen-only group receive intradermally (i.d.) a 0.1 ml injection of an emulsion (1:1 mixture) of bovine type II collagen (1 mg/ml) plus complete Freund's adjuvant (CFA, 1 mg/mL) in mineral oil. Lightly anesthetized no-collagen mice are injected with an equal volume of mineral oil alone. Mice in the test group then receive an injection of a thrombin inhibitor of the present invention. The test group is further divided into sub-groups, which receive different doses of the inhibitor. Mice are weighed and their ankles and paws evaluated daily for 18 days using a scoring system ranging from 0-4 (0=no sign of arthritis; 1=swelling or redness of the paw or one digit; 2=two joints involved; 3=more than two joints involved; 4=severe arthritis of the entire paw). The onset of arthritis is indicated by contralateral paw swelling, which appears about 10 days post-injection. Clinical signs of inflammation are evaluated by the intensity of the edema in the paws and ankles. Potential biochemical assays can include, when needed, fibrin immunohistochemistry, measurements of TAT (thrombin-anti-thrombin III complex) in synovial fluids, and levels of chemokines (MIP-1alfa) and pro-inflammatory cytokines (IL-12 and TNF-alfa) expression in joints. On day 18, mice are euthanized in a carbon dioxide atmosphere.

A reduction in ankle and paw swelling of the group that received the polypeptide of the present invention compared to the collagen-only group indicates efficacy of the polypeptide in treating arthritis.

```
Free Listing of Sequences:
((GS)8 - 16 aa polypeptide linker)
                                                SEQ ID NO: 1
GSGSGSGSGSGSGSGS (gb1 - 16 aa polypeptide linker)
                                                SEQ ID NO: 2
GEWTYDDATKTFTVTE (trpzip6 - 16 aa polypeptide linker)
                                                SEQ ID NO: 3
GEWTWDDATKTWTVTE
```

-continued (trpzip5 - 16 aa polypeptide linker)
SEQ ID NO: 4
GEWTYDDATKTFTWTE (trpzip4 - 16 aa polypeptide linker)
SEQ ID NO: 5
GEWTWDDATKTWTWTE (GEGT(GS)$_4$ - 12 aa polypeptide linker)
SEQ ID NO: 6
GEGTGSGSGSGS (5 aa polypeptide targeting active site (AS) of thrombin)
SEQ ID NO: 7
IRFTD (12 aa polypeptide targeting fibrinogen-specific exosite I (ES1) of thrombin)
SEQ ID NO: 8
GDFEEIPEEYLQ (BTI1 bivalent thrombin inhibitor)
SEQ ID NO: 9
Bbs-Arg-(D-Pip)-GSGSGSGSGSGSGSGS-GDFEEIPEEYLQ (BTI2 bivalent thrombin inhibitor)
SEQ ID NO: 10
Bbs-Arg-(D-Pip)-GEWTYDDATKTFTVTE-GDFEEIPEEYLQ (BTI3 bivalent thrombin inhibitor)
SEQ ID NO: 11
Bbs-Arg-(D-Pip)-GEWTWDDATKTWTVTE-GDFEEIPEEYLQ (BTI4 bivalent thrombin inhibitor)
SEQ ID NO: 12
Bbs-Arg-(D-Pip)-GEWTYDDATKTFTWTE-GDFEEIPEEYLQ (BTI5 bivalent thrombin inhibitor)
SEQ ID NO: 13
Bbs-Arg-(D-Pip)-GEWTWDDATKTWTWTE-GDFEEIPEEYLQ (MH2-GS bivalent thrombin inhibitor)
SEQ ID NO: 14
IRFTD-GEGTGSGSGSGS-GDFEEIPEEYLQ (MH2-gb1 bivalent thrombin inhibitor)
SEQ ID NO: 15
IRFTD-GEWTYDDATKTFTVTE-GDFEEIPEEYLQ (MH2-wZIP6 bivalent thrombin inhibitor)
SEQ ID NO: 16
IRFTD-GEWTWDDATKTWTVTE-GDFEEIPEEYLQ (MH2-wZIP5 bivalent thrombin inhibitor)
SEQ ID NO: 17
IRFTD-GEWTYDDATKTFTWTE-GDFEEIPEEYLQ (MH2-wZIP4 bivalent thrombin inhibitor)
SEQ ID NO: 18
IRFTD-GEWTWDDATKTWTWTE-GDFEEIPEEYLQ (16 aa polypeptide linker)($X^5$, $X^{12}$ and $X^{14}$ are any amino acid)
SEQ ID NO: 19
GEWTX$^5$DDATKTX$^{12}$TX$^{14}$TE (12 aa polypeptide linker)($X^1$, $X^5$, $X^6$, $X^7$, $X^8$ and $X^{12}$ are any amino acid)
SEQ ID NO: 20
X$^1$WTWX$^5$X$^6$X$^7$X$^8$WTWX$^{12}$ (trpzip1 - 12 aa polypeptide linker)
SEQ ID NO: 21
SWTWEGNKWTWK (trpzip1A - 12 aa polypeptide linker)
SEQ ID NO: 22
TWTWNGSAWTWN (trpzip2 - 12 aa polypeptide linker)
SEQ ID NO: 23
SWTWENGKWTWK (trpzip3 - 12 aa polypeptide linker)
SEQ ID NO: 24
SWTWEpNKWTWK (11 aa polypeptide targeting fibrinogen-specific exosite I of thrombin)
SEQ ID NO: 25
GDFEEIPEEYL (4 aa polypeptide targeting active site (AS) of thrombin)
SEQ ID NO: 26
FQPR (4 aa polypeptide targeting active site (AS) of thrombin)
SEQ ID NO: 27
WDPR (linker + tbm2 from BTI1)
SEQ ID NO: 28
CGSGSGSGSGSGSGSGS-GDFEEIPEEYLQ (6 aa polypeptide targeting active site (AS) of thrombin)
SEQ ID NO: 29
IRFTDG (linker fragment from mini-hirudin 2)
SEQ ID NO: 30
GEGTPNPESHNN ((GS)$_6$ - 12 aa polypeptide linker)
SEQ ID NO: 31
GSGSGSGSGSGS (GEGT(GS)$_6$ - 16 aa polypeptide linker)
SEQ ID NO: 32
GEGTGSGSGSGSGSGS (MH1 - bivalent thrombin inhibitor)
SEQ ID NO: 33
VRFTD-GEGTPKPQSHDN-GDFEEIPEEYLQ (MH2 - bivalent thrombin inhibitor)
SEQ ID NO: 34
IRFTD-GEGTPNPESHNN-GDFEEIPEEYLQ (MH2-allGS - bivalent thrombin inhibitor)
SEQ ID NO: 35
IRFTD-GSGSGSGSGSGS-GDFEEIPEEYLQ (MH2-longGS - bivalent thrombin inhibitor)
SEQ ID NO: 36
IRFTD-GEGTGSGSGSGSGSGS-GDFEEIPEEYLQ (18 aa polypeptide linker with two Cys residues linked by an SS bond)
SEQ ID NO: 37
Cys[S-S]CysGSGSGSGSGSGSGSGS (4 aa polypeptide)
SEQ ID NO: 38
IQPR (11 aa polypeptide segment of SEQ ID NO: 8)
SEQ ID NO: 39
DFEEIPEEYLQ (covalently blocked MH2-trpzip4) ($x_4$, $x_3$, $x_2$ and $x_1$ are any amino acid)
SEQ ID NO: 40
$x_4x_3x_2x_1$-IRFTD-GEWTWDDATKTWTWTE-GDFEEIPEEYLQ

```
(6 aa polypeptide targeting active site (AS) of
thrombin)
                                        SEQ ID NO: 41
PRFTD (5 aa polypeptide from SEQ ID NO: 33 or MH1)
                                        SEQ ID NO: 42
VRFTD (4 aa polypeptide)
                                        SEQ ID NO: 43
IEGR (BRI-T207 bivalent thrombin inhibitor)
                                        SEQ ID NO: 44
FQPR-PRFTD-GEWTWDDATKTWTWTE-GDFEEIPEEYL (BRI-T109 bivalent thrombin inhibitor)
                                        SEQ ID NO: 45
PRFTD-GEWTWDDATKTWTWTE-GDFEEIPEEYLQ (BRI-T110 bivalent thrombin inhibitor)
                                        SEQ ID NO: 46
PRFTD-GEWTWDDATKTWTWTE-GDFEEIPEEYL (BRI-T111 bivalent thrombin inhibitor)
                                        SEQ ID NO: 47
IRFTD-GEWTWDDATKTWTWTE-GDFEEIPEEYL (BRI-T113 bivalent thrombin inhibitor)
                                        SEQ ID NO: 48
fPRP-GEWTWDDATKTWTWTE-GDFEEIPEEYL (BRI-T204 bivalent thrombin inhibitor activatable
by FXa)
                                        SEQ ID NO: 49
IEGR-IRFTDGEWTWDDATKTWTWTE-GDFEEIPEEYL (BRI-T205 bivalent thrombin inhibitor activatable
by FXa)
                                        SEQ ID NO: 50
IEGR-IRFTDGEWTYDDATKTFTWTE-GDFEEIPEEYL (BRI-T217 bivalent thrombin inhibitor)
                                        SEQ ID NO: 51
FQPR-IRFTDGEWTWDDATKTWTWTE-GDFEEIPEEYL (BRI-T227 bivalent thrombin inhibitor)
                                        SEQ ID NO: 52
FQPR-VRFTDGEWTWDDATKTWTWTE-GDFEEIPEEYL (BRI-T237 bivalent thrombin inhibitor)
                                        SEQ ID NO: 53
FQPR-LRFTDGEWTWDDATKTWTWTE-GDFEEIPEEYL (BRI-T247 bivalent thrombin inhibitor)
                                        SEQ ID NO: 54
FQPR-FRFTDGEWTWDDATKTWTWTE-GDFEEIPEEYL (BRI-T208 bivalent thrombin inhibitor)
                                        SEQ ID NO: 55
fPR-PRFTDGEWTWDDATKTWTWTE-GDFEEIPEEYL (BRI-T218 bivalent thrombin inhibitor)
                                        SEQ ID NO: 56
fPR-IRFTDGEWTWDDATKTWTWTE-GDFEEIPEEYL (BRI-T228 bivalent thrombin inhibitor)
                                        SEQ ID NO: 57
fPR-VRFTDGEWTWDDATKTWTWTE-GDFEEIPEEYL (BRI-T238 bivalent thrombin inhibitor)
                                        SEQ ID NO: 58
fPR-LRFTDGEWTWDDATKTWTWTE-GDFEEIPEEYL (BRI-T248 bivalent thrombin inhibitor)
                                        SEQ ID NO: 59
fPR-FRFTDGEWTWDDATKTWTWTE-GDFEEIPEEYL (BRI-T209 bivalent thrombin inhibitor)
                                        SEQ ID NO: 60
WDPR-PRFTDGEWTWDDATKTWTWTE-GDFEEIPEEYL (BRI-T219 bivalent thrombin inhibitor)
                                        SEQ ID NO: 61
WDPR-IRFTDGEWTWDDATKTWTWTE-GDFEEIPEEYL (BRI-T229 bivalent thrombin inhibitor)
                                        SEQ ID NO: 62
WDPR-VRFTDGEWTWDDATKTWTWTE-GDFEEIPEEYL (BRI-T239 bivalent thrombin inhibitor)
                                        SEQ ID NO: 63
WDPR-LRFTDGEWTWDDATKTWTWTE-GDFEEIPEEYL (BRI-T249 bivalent thrombin inhibitor)
                                        SEQ ID NO: 64
WDPR-FRFTDGEWTWDDATKTWTWTE-GDFEEIPEEYL (BRI-T210 bivalent thrombin inhibitor)
                                        SEQ ID NO: 65
fPR-PRFTDGEWTYDDATKTFTWTE-GDFEEIPEEYL (BRI-T220 bivalent thrombin inhibitor)
                                        SEQ ID NO: 66
fPR-IRFTDGEWTYDDATKTFTWTE-GDFEEIPEEYL (BRI-T230 bivalent thrombin inhibitor)
                                        SEQ ID NO: 67
fPR-VRFTDGEWTYDDATKTFTWTE-GDFEEIPEEYL (BRI-T240 bivalent thrombin inhibitor)
                                        SEQ ID NO: 68
fPR-LRFTDGEWTYDDATKTFTWTE-GDFEEIPEEYL (BRI-T250 bivalent thrombin inhibitor)
                                        SEQ ID NO: 69
fPR-FRFTDGEWTYDDATKTFTWTE-GDFEEIPEEYL (4 aa polypeptide)
                                        SEQ ID NO: 70
FNPR (5 aa linker segment (Gly)$_4$-Asn)
                                        SEQ ID NO: 71
GGGGN (5 aa polypeptide targeting active site (AS) of
thrombin) (p1 is I, V, L or F)
                                        SEQ ID NO: 72
p1RFTD (8 aa polypeptide targeting active site (AS) of
thrombin) (p1 is I, V, L or F)
                                        SEQ ID NO: 73
fPR-p1RFTD (bivalent thrombin inhibitor) (p1 is I, V, L or F)
                                        SEQ ID NO: 74
fPR-p1RFTDGEWTWDDATKTWTWTE-GDFEEIPEEYL (fragment of bivalent thrombin inhibitor)
                                        SEQ ID NO: 75
IRFTD-GEWTWDDATKTWTWTE (12 aa haemadin C-terminus specific for AB2 or ES2
of thrombin)
                                        SEQ ID NO: 76
EFEEFEIDEEEK (PEPA1 - 131 aa human VH domain binder for PPACK-
thrombin)
                                        SEQ ID NO: 77
EVQLQASGGGLVQSGDSLRLSCAASGRTFSTYAMGWFRQAPGKLREFVGV
ISSSGYTHYTNSVRGRFTISRDNAKNMVYLQMNSLKPEDTAVYYCAAADR
RFIATDGKQYDYWGQGTQVTVSSLEHHHHHH
```

-continued (BRI-T304 bivalent thrombin inhibitor)
SEQ ID NO: 78
IRFTD-GEWTWDDATKTWTWTE-GEFEEFEIDEEEK (BRI-T404 bivalent thrombin inhibitor)
SEQ ID NO: 79
IRFTDGEWTWDDATKTWTWTEGGSEVQLQASGGGLVQSGDSLRLSCAASG
RTFSTYAMGWFRQAPGKLREFVGVISSSGYTHYTNSVRGRFTISRDNAKN
MVYLQMNSLKPEDTAVYYCAAADRRFIATDGKQYDYWGQGTQVTVSSLEH
HHHHH (VSL-PEPA1)
SEQ ID NO: 80
GSVSPRPQLHNDGGGSSEVQLQASGGGLVQSGDSLRLSCAASGRTFSTYA
MGWFRQAPGKLREFVGVISSSGYTHYTNSVRGRFTISRDNAKNMVYLQMN
SLKPEDTAVYYCAAADRRFIATDGKQYDYWGQGTQVTVSSLEHHHHHH (22 amino acid fragment of bivalent thrombin
inhibitor)
SEQ ID NO: 81
IRFTDGEWTWDDATKTWTWTEG (MH2-wZIP1-2G bivalent thrombin inhibitor)
SEQ ID NO: 82
IRFTDG-GSWTWEGNKWTWKG-GDFEEIPEEYLQ (MH2-wZIP1 bivalent thrombin inhibitor)
SEQ ID NO: 83
IRFTDG-SWTWEGNKWTWK-GDFEEIPEEYLQ (42 nt forward-primer)
SEQ ID NO: 84
acctggaccgaaggcggcagcgatgtccagctgcaggcgtct (30 nt reverse-primer)
SEQ ID NO: 85
aatcggctcgagtgaggagacggtgacctg (81 nt forward-primer)
SEQ ID NO: 86
gcccagccggcgatggccattcgttttactgatggcgaatggacctggga
tgatgccaccaaaacctggacctggaccgaa (30 nt reverse-primer)
SEQ ID NO: 87
aatcggctcgagtgaggagacggtgacctg

REFERENCES

The contents of the entirety of each of which are incorporated by this reference.

Adiguzel E, Ahmad P J, Franco C, Bendeck M P. (2009) Collagens in the progression and complications of atherosclerosis. *Vasc Med.* 14(1), 73-89.

Agorogiannis E I, Agorogiannis G I. (2002) Coagulation, angiogenesis, and venous thromboembolism in cancer. *Lancet.* 359, 1440.

Asai S, Sato T, Tada T, Miyamoto T, Kimbara N, Motoyama N, Okada H, Okada N. (2004) Absence of procarboxypeptidase R induces complement-mediated lethal inflammation in lipopolysaccharide-primed mice. *J Immunol.* 173, 4669-4674.

Baldwin R L. (1996) How Hofmeister ion interactions affect protein stability. *Biophys. J.* 71, 2056-2063.

Benjamin T H, Milan M. (2001) *Model Systems for Studying Polyvalent Carbohydrate Binding Interactions.* (Springer, Berlin/Heidelberg) pp. 1-44.

Betz A, Hofsteenge J, Stone S R. (1992) Interaction of the N-terminal region of hirudin with the active-site cleft of thrombin. *Biochemistry.* 31(19), 4557-4562.

Bianchini E P, Orcutt S J, Panizzi P, Bock P E, Krishnaswamy S. (2005) Ratcheting of the substrate from the zymogen to proteinase conformations directs the sequential cleavage of prothrombin by prothrombinase. *Proc. Natl. Acad. Sci. U.S.A.* 102, 10099-10104.

Bischoff R, Lepage P, Jaquinod M, Cauet G, Acker-Klein M, Clesse D, Laporte M, Bayol A, Van Dorsselaer A, Roitsch C. (1993) *Biochemistry.* 32, 725-734.

Blanco F J, Rivas G, Serrano L. (1994) A short linear peptide that folds into a native stable beta-hairpin in aqueous solution. *Nat Struct Biol.* 1, 584-590.

Bock P E, Panizzi P, Verhamme I M. (2007) Exosites in the substrate specificity of blood coagulation reactions. *J. Thromb. Haemost.* 5 Suppl 1, 81-94.

Bogatkevich G S, Ludwicka-Bradley A, Nietert P J, Akter T, van Ryn J, Silver R M. (2011) Antiinflammatory and antifibrotic effects of the oral direct thrombin inhibitor dabigatran etexilate in a murine model of interstitial lung disease. *Arthritis & Rheumatism.* 63(5), 1416-1425.

Boilard E, Nigrovic P A, Larabee K, Watts G F M, Coblyn J S, Weinblatt M E, Massarotti E M, Remold-O'Donnell E, Farndale R W, Ware j, Lee D M. (2010) Platelets Amplify Inflammation in Arthritis via Collagen-Dependent Microparticle Production. *Science.* 327(5965), 580-583.

Brummel-Ziedens K, Undas A, Orfeo T, Gissel M, Butenas S, Zmudka K, Mann K G. (2008) Thrombin generation in acute coronary syndrome and stable coronary artery disease: dependence on plasma facto composition. *J. Thromb. Haemost.* 6, 104-110.

Busso N, Hamilton J A. (2002) Extravascular coagulation and the plasminogen activator/plasmin system in rheumatoid arthritis. *Arthrit. Rheum.* 46, 2268-2279.

Butenas S, Orfeo T, Brummel-Ziedens K E, Mann K G. (2007) Influence of bivalirudin on tissue factor-triggered coagulation. *Blood Coagulation and Fibrinolysis.* 18(5), 407-414.

Cappiello M, Vilardo P G, Del Corso A, Mura U. (1998) Hirunorms, novel hirudin-like direct thrombin inhibitors. *General Pharmacology.* 30(4), 565-568.

Cavaluzzi M J, Kerwood D J, Borer P N. (2002) Accurate nucleic acid concentrations by nuclear magnetic resonance. *Analytical Biochemistry.* 308, 373-380.

Chan J M, Zhang L, Tong R, Ghosh D, Gao W, Liao G, Yuet K P, Gray D, Rhee J W, Cheng J, Golomb G, Libby P, Langer R, Farokhzad O C. (2010) Spatiotemporal controlled delivery of nanoparticles to injured vasculature. *Proc Natl Acad Sci U.S.A.* 107, 2213-2218.

Cochran A G, Skelton N J, Starovasnik M A. (2001) Tryptophan zippers: stable, monomeric beta-hairpins. *Proc Natl Acad Sci U.S.A.* 98, 5578-5583.

Corral-Rodriguez M A, Macedo-Ribeiro S, Pereira P J B, Fuentes-Prior P. (2010) Leech-derived thrombin inhibitors: from structures to mechanisms to clinical applications. *Journal of Medicinal Chemistry.* 53(10), 3847-3861.

Couture L, Richer L P, Cadieux C, Thomson C M, Hossain S M. (2011) An optimized method to assess in vivo efficacy of antithrombotic drugs using optical coherence tomography and a modified Doppler flow system. *Journal of Pharmacological and Toxicological Methods.* 64(3), 264-268.

De Simone G, Lombardi A, Galdiero S, Nastri F, Della M R, Staiano N, Pedone C, Bolognesi M, Pavone V. (1998) *Protein Sci.* 7, 243-253.

DiMaio J, Gibbs B, Munn D, Lefebvre J, Ni F, Konishi Y. (1990) Bifunctional thrombin inhibitors based on the sequence of hirudin[54-65]. *J Biol Chem.* 265, 21698-21703.

Duguid J B. (1946) Thrombosis as a factor in the pathogenesis of coronary atherosclerosis. *J Pathol Bacterial.* 58, 207-212.

Eckly A, Hechler B, Freund M, Zerr M, Cazenave J-P, Lanza F, Mangin Ph, Gachet C. (2011) Mechanisms underlying $FeCl_3$-induced arterial thrombosis. *Journal of Thrombosis and Haemostasis.* 9(4), 779-789.

Farrow N A, Muhandiram R, Ulson A, Pawson T, Singer, Pascal S M, Kay C M, Gish G, Shoelson S E, Forman-Kay J D, and Kay L E. (1999) Backbone Dynamics of a Free and a Phosphopeptide-Complexed Src Homology 2 Domain Studied by $^{15}N$ NMR Relaxation. *Biochemistry.* 33, 5984-6003.

Fareed J, Hoppensteadt D A, Fareed D, Demir M, Wahi R, Clarke M, Adiguzel C, Bick R. (2008) Survival of heparins, oral anticoagulants, and aspirin after the year 2010. *Semin. Thromb. Hemost.* 34, 58-73.

Fethiere J, Tsuda Y, Coulombe R, Konishi Y, Cygler M. (1996) Crystal structure of two new bifunctional nonsubstrate type thrombin inhibitors complexed with human alpha-thrombin. *Protein Sci.* 5, 1174-1183.

Fischer B E, Schlokat U, Himmelspach M, Dorner F. (1998) Binding of hirudin to meizothrombin. *Protein Engineering.* 11(8), 715-721.

Flick M J, Chauhan A K, Frederick M, Talmage K E, Kombrinck K W, Miller W, Mullins E S, Palumbo J S, Zheng X, Esmon N L, Esmon C T, Thornton S, Becker A, Pelc L A, Cera E D, Wagner D D, Degen J L. (2011) The development of inflammatory joint disease is attenuated in mice expressing the anticoagulant prothrombin mutant W215A/E217A. *Blood.* 117, 6326-6337.

Fullerton G D, Rahal A. (2007) Collagen structures: the molecular source of the tendon magic angle effect. *J. Magn. Reson. Imaging.* 25, 345-361.

Gill S C, von Hippel P H. (1989) Calculation of protein extinction coefficients from amino acid sequence data. *Anal Biochem.* 182, 319-326.

Griffin L C, Tidmarsh G F, Bock L C, Toole J J, Leung L L. (1993) In vivo anticoagulant properties of a novel nucleotide-based thrombin inhibitor and demonstration of regional anticoagulation in extracorporeal circuits. *Blood.* 81, 3271-3276.

Gresele P, Agnelli G. (2002) Novel approaches to the treatment of thrombosis. *Trends Pharmacol. Sci.* 23, 25-32.

Gross P L, Weitz J I. (2008) New anticoagulants for treatment of venous thromboembolism. *Arterioscler. Thromb. Vasc. Biol.* 28, 380-386.

Hackeng T M, Tans G, Koppelman S J, de Groot P G, Rosing J, Bouma B N. (1996) Protein C activation on endothelial cells by prothrombin activation products generated in situ: meizothrombin is a better protein C activator than alpha-thrombin. *Biochem. J.* 319, 399-405.

Hamad-Schifferli K, Schwartz J J, Santos A T, Zhang S, Jacobson J M. (2002) Remote electronic control of DNA hybridization through inductive coupling to an attached metal nanocrystal antenna. *Nature* 415, 152-155.

Hansson G K, Libby P. (2006) The immune response in atherosclerosis: a double-edged sword. *Nat. Rev. Immunol.* 6, 508-519.

Ho J G, Kitov P I, Paszkiewicz E, Sadowska J, Bundle D R, Ng K K. (2005) Ligand-assisted aggregation of proteins. Dimerization of serum amyloid P component by bivalent ligands. *J. Biol. Chem.* 280, 31999-32008.

Hoppensteadt D A, Jeske W, Walenga J, Fareed J. (2008) The future of anticoagulation. *Semin. Respir. Crit Care Med.* 29, 90-99.

Houdijk W P, Sakariassen K S, Nievelstein P F, Sixma J J. (1985) Role of factor VIII-von Willebrand factor and fibronectin in the interaction of platelets in flowing blood with monomeric and fibrillar human collagen types I and III. *J Clin Invest.* 75(2), 531-540.

Hsu H-J, Tsai K-C, Sun Y-K, Chang H-J, Huang Y-J, Yu H-M, Lin C-H, Mao S-H, Yang A-S. (2008) Factor Xa active site substrate specificity with substrate phage display and computational molecular modeling. *J. Biol. Chem.* 283, 12343-12353.

Ishihara Y, Calderon A, Watanabe H, Okamoto K, Suzuki Y, Kuroda K. (1995) A precise and fast temperature mapping using water proton chemical shift. *Magn Res Med.* 34, 814-823.

Kabir S R, Yokoyama K, Mihashi K, Kodama T, Suzuki M. (2003) Hyper-mobile water is induced around actin filaments. *Biophysical J.* 85, 3154-3161.

Kamath P, Krishnaswamy S. (2008) Fate of membrane-bound reactants and products during the activation of human prothrombin by prothrombinase. *J. Biol. Chem.* 283, 30164-30173.

Karimi M, Cohan N. (2010) Cancer-associated thrombosis. *Open Cardiovasc Med. J.* 4, 78-82.

Khorana A A, Fine R L. (2004) Pancreatic cancer and thromboembolic disease. *Lancet Oncol.* 5, 655-663.

Khrenov A V, Ananyeva N M, Griffin J H, Saenko E L. (2002) Coagulation pathways in atherothrombosis. *Trends Cardiovasc. Med.* 12, 317-324.

Kinoshita M, Suzuki M. (2009) A statistical-mechanical analysis on the hypermobile water around a large solute with high surface charge density. *J. Chem. Phys.* 130, 014707.

Kitamoto Y, Nakamura E, Tokunaga H, Murakami E, Imamura T. (2008) Thrombin in synovial fluid as a marker of synovial inflammation: A definitive measurement by ELISA and correlation with VEGF. *Clinica Chim. Acta.* 398, 159-160.

Korzhnev D M, Kay L E. (2008) Probing invisible, low-populated states of protein molecules by relaxation dispersion NMR spectroscopy: an application to protein folding. *Acc. Chem. Res.* 41, 442-451.

LaVan D A, McGuire T, Langer R. (2003) Small-scale systems for in vivo drug delivery. *Nat. Biotechnol.* 21, 1184-1191.

Lazar J B, Winant R C, Johnson P H. (1991) Hirudin: amino-terminal residues play a major role in the interaction with thrombin. *J Biol. Chem.* 266, 685-688.

Levi M, Keller T T, van Gorp E, ten Cate H. (2003) Infection and inflammation and the coagulation system. *Cardiovasc. Res.* 60, 26-39.

Li R, Jiang Z, Yang H, Guan Y. (2006) Effects of ions in natural water on the $^{17}O$ NMR chemical shift of water and their relationship to water cluster. *J. Mol. Liq.* 126, 14-18.

Libby P. (2002) Atherosclerosis: the new view. *Sci. Am.* 286, 46-55.

Libby P, Theroux P. (2005) Pathophysiology of coronary artery disease. *Circulation.* 111, 3481-3488.

Liu J, Zhang Z, Tan X, Hol W G, Verlinde C L, Fan E. (2005) Protein heterodimerization through ligand-bridged multivalent pre-organization: enhancing ligand binding toward both protein targets. *J Am. Chem. Soc.* 127, 2044-2045.

Lombardi A, Nastri F, Della Morte R, Rossi A, De Rosa A, Staiano N, Pedone C, Pavone V. (1996) Rational design of true hirudin mimetics: synthesis and characterization of multisite-directed α-thrombin inhibitors. *J. Med. Chem.* 39, 2008-2017.

Lorenzet R, Donati M B. (2002) Blood clotting activation, angiogenesis and tumor metastasis: any role for TFPI? *Thromb. Haemost.* 87, 928-929.

Ludwicka-Bradley A, Bogatkevivh G, Silver R M. (2004) Thrombin-mediated cellular dysfunction in pulmonary fibrosis associated with systemic sclerosis (scleroderma). *Clin. Exp. Rheumatol.* 22 (suppl. 33), S38-S46.

Lutz N W, Kuesel A C, Hull W E. (1993) A $^1$H-NMR method for determining temperature in cell culture perfusion systems. *Magnetic Resonance in Medicine.* 29(1), 113-118.

Ma J, Goldberg G I, Tjandra N. (2008) Weak alignment of biomolecules in collagen gels: an alternative way to yield residual dipolar couplings for NMR spectroscopy. *J. Am. Chem. Soc.* 130, 16148-16149.

Mallamace F, Corsaro C, Mallamace D, Baglioni P, Stanley H E, Chen S-H. (2011) A Possible Role of Water in the Protein Folding Process. *J. Phys. Chem. B.* 115(48), 14280-14294.

Mann K G. (1987) The assembly of blood clotting complexes on membranes. *Trends in Biochemical Sciences.* 12, 229-233.

Mann K G, Jenny R J, Krishnaswamy S. (1988) Cofactor proteins in the assembly and expression of blood clotting enzyme complexes. *Annu. Rev. Biochem.* 57, 915-956.

Mann K G, Brummel-Ziedins K, Orfeo T, Butenas S. (2006) Models of blood coagulation. *Blood Cells Mol. Dis.* 36, 108-117.

Maraganore J M, Chao B, Joseph M L, Jablonski J, Ramachandran K L. (1989) Anticoagulant activity of synthetic hirudin peptides. *J. Biol. Chem.* 264, 8692-8698.

Maraganore J M, Bourdon P, Jablonski J, Ramachandran K L, Fenton J W. (1990) Design and characterization of hirulogs: a novel class of bivalent peptide inhibitors of thrombin. *Biochemistry.* 29, 7095-7101.

Marsden P A, Ning Q, Fung L S, Luo X, Chen Y, Mendicino M, Ghanekar A, Scott J A, Miller T, Chan C W, Chan M W, He W, Gorczynski R M, Grant D R, Clark D A, Phillips M J, Levy G A. (2003) The Fgl2/fibroleukin prothrombinase contributes to immunologically mediated thrombosis in experimental and human viral hepatitis. *J. Clin. Invest.* 112, 58-66.

Marty I, Peclat V, Kirdaire G, Salvi R, So A, Busso N. (2001) Amelioration of collagen-induced arthritis by thrombin inhibition. *J. Clin. Invest.* 107, 631-640.

Mathews I I, Padmanabhan K P, Ganesh V, Tulinsky A, Ishii M, Chen J, Turck C W, Coughlin S R, Fenton J W. (1994) Crystallographic structures of thrombin complexed with thrombin receptor peptides: existence of expected and novel binding modes. *Biochemistry.* 33, 3266-3279.

Morris R, Winyard P G, Blake D R, Morris C J. (1994) Thrombin in inflammation and healing: relevance to rheumatoid arthritis. *Ann. Rheum. Dis.* 53, 72-79.

Munoz V, Thompson P A, Hofrichter J, Eaton W A. (1997) Folding dynamics and mechanism of beta-hairpin formation. *Nature.* 390, 196-199.

Nesheim M. (2003) Thrombin and fibrinolysis. *Chest.* 124, 33-39.

Ng, Y D A. (2005) Exploring the nature of protein-protein interactions through the design of mini-proteins that bind and inhibit human thrombin. McGill University Ph.D. Thesis, Department of Biochemistry, McGill University.

Ni F, Konishi Y, Scheraga H A. (1990) Thrombin-bound conformation of the C-terminal fragments of hirudin determined by transferred nuclear Overhauser effects. *Biochemistry.* 29, 4479-4489.

Ni F, Ripoll D R, Purisima E O. (1992) Conformational stability of a thrombin-binding peptide derived from the hirudin C-terminus. *Biochemistry.* 31(9), 2545-54.

Ni F, Zhu Y, Scheraga H A. (1995) Thrombin-bound structures of designed analogs of human fibrinopeptide A determined by quantitative transferred NOE spectroscopy: a new structural basis for thrombin specificity. *J Mol Biol.* 252, 656-671.

Ni F, Tolkatchev D, Natapova A, Koutychenko A. (2008) Peptide Inhibitors of Thrombin as Potent Anticoagulants. U.S. Pat. No. 7,456,152 issued Nov. 25, 2008.

Nierodzik M, Karpatkin S. (2005) Hypercoagulability preceding cancer. Does hypercoagulability awaken dormant tumor cells in the host? *J. Thromb. Haemost.* 3, 577-580.

Nishimura T, Myles T, Piliponsky A M, Kao P N, Berry G J, Leung L L K. (2007) Thrombin-activatable procarboxypeptidase B regulates activated complement C5a in vivo. *Blood.* 109, 1992-1997.

Opal S M, Esmon C T. (2003) Bench-to-bedside review: functional relationships between coagulation and the innate immune response and their respective roles in the pathogenesis of sepsis. *Crit. Care.* 7, 23-38.

Ornstein D L, Meehan K R, Zacharski L R. (2002) The coagulation system as a target for the treatment of human gliomas. *Semin. Thromb. Hemost.* 28, 19-28.

Osborne M J, Su Z, Sridaran V, Ni F. (2003) Efficient expression of isotopically labeled peptides for high resolution NMR studies: application to the Cdc42/Rac binding domains of virulent kinases in *Candida albicans*. *J Biomol NMR.* 26, 317-326.

Penz S, Reininger A J, Brandi R, Goyal P, Rabie T, Bernlochner I, Rother E, Goetz C, Engelmann B, Smethurst P A, Ouwehand W H, Farndale R, Nieswandt B, Siess W. (2005) Human atheromatous plaques stimulate thrombus formation by activating platelet glycoprotein VI. *FASEB J.* 19, 898-909.

Peter K, Graeber J, Kipriyanov S, Zewe-Welschof M, Runge M S, Kubler W, Little M, Bode C. (2000) Construction and functional evaluation of a single-chain antibody fusion protein with fibrin targeting and thrombin inhibition after activation by factor Xa. *Circulation.* 101, 1158-1164.

Peter K, Gupta A, Nordt T, Bauer S, Runge M S, Bode C. (2003) Construction and in vitro testing of a novel fab-hirudin-based fusion protein that targets fibrin and inhibits thrombin in a factor xa-dependent manner. *J Cardiovasc Pharmacol.* 42, 237-244.

Peters D, Kastantin M, Kotamraju V R, Karmali P P, Gujraty K, Tirrell M, Ruoslahti E. (2009) Targeting atherosclerosis by using modular, multifunctional micelles. *Proc Natl Acad Sci U.S.A.* 106, 9815-9819.

Privalov P L. (1997) Thermodynamics of protein folding. *J Chem Thermodynamics.* 29, 447-474.

Rak J, Yu J L, Luyendyk J, Mackman N. (2006) Oncogenes, trousseau syndrome, and cancer-related changes in the coagulome of mice and humans. *Cancer Res.* 66, 10643-10646.

Ramos C H I, Baldwin R L. (2002) Sulfate anion stabilization of native ribonuclease A both by anion binding and by the Hofmeister effect. *Protein Science.* 11(7), 1771-1778.

Reininger A J, Bernlochner I, Penz S M, Ravanat C, Smethurst P, Farndale R W, Cachet C, Brandi R, Siess W. (2010) A 2-step mechanism of arterial thrombus formation induced by human atherosclerotic plaques. *J Am Coll Cardiol.* 55, 1147-1158.

Richardson J L, Kroger B, Hoeffken W, Sadler J E, Pereira P, Huber R, Bode W, Fuentes-Prior P. (2000) Crystal structure of the human α-thrombin-haemadin complex: an exosite II-binding inhibitor. *The EMBO Journal.* 19, 5650-5660.

Rieke V, Butts Pauly K. (2008) MR Thermometry. *J Magn Reson Imaging.* 27(2), 376-390.

Riewald M, Ruf W. (2002) Orchestration of coagulation protease signaling by tissue factor. *Trends Cardiovasc. Med.* 12, 149-154.

Rydel T J, Ravichandran K G, Tulinsky A, Bode W, Huber R, Roitsch C, Fenton J W 2nd. (1990) The structure of a complex of recombinant hirudin and human alpha-thrombin. *Science.* 249(4966), 277-280.

Safarik I, Safarikova M. (2004) Magnetic techniques for the isolation and purification of proteins and peptides. *BioMagn. Res. Technol.* 2, 7.

Saibeni S, Saladino V, Chantarangkul V, Villa F, Bruno S, Vecchi M, de Franchis R, Sei C, Tripodi A. (2010) Increased thrombin generation in inflammatory bowel diseases. *Thromb. Res.* 125, 278-282.

Schopf L R, Anderson K, Jaffee B D. (2006) Rat models of arthritis: Similarities, differences, advantages, and disadvantages in the identification of novel therapeutics. *Progress in Inflammation Research*, 1-34. In *In Vivo Models of Inflammation*, Vol. I, Stevenson C S, et al. eds. (Berkhauser Verlag, Basel, Switzerland).

Sedlak E, Staag L, Wittung-Stafshede P. (2008) Effect of Hofmeister ions on protein thermal stability: roles of ion hydration and peptide groups? *Arch. Biochim. Biophys.* 479, 69-73.

Slon-Usakiewicz J J, Sivaraman J, Li Y, Cygler M, Konishi Y. (2000) Design of P1' and P3' residues of trivalent thrombin inhibitors and their crystal structures. *Biochemistry.* 39, 2384-2391.

So A K, Varisco P A, Kemkes-Matthes B, Herkenne-Morard C, Chobaz-Peclat V, Gerster, J C & Busso N. (2003) Arthritis is linked to local and systemic activation of coagulation and fibrinolysis pathways. *J. Thromb. Haemost.* 1, 2510-2515.

Su Z, Vinogradova A, Koutychenko A, Tolkatchev D, Ni F. (2004) Rational Design and Selection of Bivalent and Bridge-Binding Peptide Ligands of Thrombin-Incorporating a P1-P4 Tetrapeptide Sequence: from Good Substrates to Potent Inhibitors. *Protein Eng Des Sel.* 17, 647-657.

Sukhova G K, Schonbeck U, Rabkin E, Schoen F J, Robin Poole A R, Billinghurst R C, Libby P. (1999) Evidence for Increased Collagenolysis by Interstitial Collagenases-1 and -3 in Vulnerable Human Atheromatous Plaques. *Circulation.* 99, 2503-2509.

Suzuki M, Kabir S R, Siddique M S P, Nazia U S, Miyazaki T, Kodama T. (2004) Myosin-induced volume increase of the hyper-mobile water surrounding actin filaments. *Biochem Biophys Res Commun.* 322, 340-346.

Tan K T, Lip G Y H. (2008) Imaging of the unstable plaque. *International Journal of Cardiology.* 127(2), 157-165.

Tanha J, Nguyen T D, Ng A, Ryan S, Ni F, MacKenzie C R. (2006) Improving solubility and refolding efficiency of human V(H)s by a novel mutational approach. *Protein Eng Des Sel.* 19, 503-509.

Taka T, Konishi Y, Slon-Usakiewicz J, Medvedkin V, Tsuda Y, Okada Y, Seki J,

Yamamoto J. (2000) Inhibitory effect of various thrombin inhibitors on shear-induced platelet function and dynamic coagulation. *Eur J Pharmacol.* 406, 181-189.

Theroux P, Willerson J T, Armstrong P W. (2000). Progress in the treatment of acute coronary syndromes: a 50-year perspective (1950-2000). *Circulation.* 102, IV2-IV13.

Tolkatchev D, Xu P, Ni F. (2003) Probing the kinetic landscape of transient peptide-protein interactions by use of peptide $^{15}$N NMR relaxation dispersion spectroscopy: binding of an antithrombin peptide to human prothrombin. *J. Am. Chem. Soc.* 125, 12432-12442.

Tolkatchev D, Vinogradova A, Ni F. (2005) Transforming bivalent ligands into retractable enzyme inhibitors through polypeptide-protein interactions. *Bioorg Med Chem Lett.* 15, 5120-5123.

Tolkatchev D, Plamondon J, Gingras R, Su Z, Ni F. (2010) Recombinant Production of Intrinsically Disordered Proteins for Biophysical and Structural Characterization. In: Uversky V N, Longhi S, eds. *Instrumental Analysis of Intrinsically Disordered Proteins: Assessing Structure And Conformation.* (Hoboken, N J, USA: John Wiley & Sons, Inc.)

Torbet J, Malbouyres M, Builles N, Justin V, Roulet M, Damour O, Oldberg A, Ruggiero F, Hulmes D J S. (2007) Orthogonal scaffold of magnetically aligned collagen lamellae for corneal stroma reconstruction. *Biomaterials.* 28, 4268-4278.

Tsuda Y, Cygler M, Gibbs B F, Pedyczak A, Fethiere J, Yue S Y, Konishi Y. (1994) Design of potent bivalent thrombin inhibitors based on hirudin sequence: incorporation of nonsubstrate-type active site inhibitors. *Biochemistry.* 33, 14443-14451.

Vergnolle N. (2009) Protease-activated receptors as drug targets in inflammation and pain. *Pharmacol. Therapeut.* 123, 292-309.

Vorchheimer D A, Fuster V. (2002) Thrombin inhibitors in acute coronary artery disease. *Eur. Heart J.* 23, 1142-1144.

Wallace A, Dennis S, Hofsteenge J, Stone S R. (1989) Contribution of the N-terminal region of hirudin to its interaction with thrombin. *Biochemistry.* 28(26), 10079-10084.

Wang X, Xu L. (2005) An optimized murine model of ferric chloride-induced arterial thrombosis for thrombosis research. *Thromb. Res.* 115, 95-100.

Wang, X. (2008) Lipopolysaccharide augments venous and arterial thrombosis in the mouse. *Thrombosis Research.* 123(2), 355-360.

Warkentin T E. (2004) Bivalent direct thrombin inhibitors: hirudin and bivalirudin. Best Practice Res. *Clin. Haematol.* 17, 105-125.

Weitz J I, Buller H R. (2002) Direct thrombin inhibitors in acute coronary syndromes: present and future. *Circulation.* 105, 1004-1011.

Winant R C, Lazar J B, Johnson P H. (1991) Chemical modifications and amino acid substitutions in recombinant hirudin that increase hirudin-thrombin affinity. *Biochemistry.* 30, 1271-1277.

Wishart D S, Bigam C G, Holm A, Hodges R S, Sykes B D. (1995) $^1$H, $^{13}$C and $^{15}$N random coil NMR chemical shifts of the common amino acids. I. Investigations of nearest-neighbor effects. *J Biomol NMR.* 5, 67-81.

Wood J P, Silveira J R, Maille N M, Haynes L M, Tracy P B. (2011) Prothrombin activation on the activated platelet surface optimizes expression of procoagulant activity. *Blood.* 117(5), 1710-1718.

Zhou H X. (2001a) Loops in Proteins Can Be Modeled as Worm-Like Chains. *J Phys Chem B.* 105, 6763-6766.

Zhou H X. (2001b) The affinity-enhancing roles of flexible linkers in two-domain DNA-binding proteins. *Biochemistry.* 40, 15069-15073.

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

The invention claimed is:

1. A multi-functional thrombin binding agent of formula (I):

tbm1-xRFTD-linker-tbm2     (I)

wherein:
- tbm1 is a reversible binding peptide sequence for the catalytic active site of thrombin and is proteolytically removable by thrombin;
- tbm2 is a binding moiety for a surface of thrombin not overlapping with the catalytic active site;
- xRFTD is a pentapeptide of sequence PRFTD (SEQ ID NO:41) or a pentapeptide of sequence xRFTD (SEQ ID NO:72) where x is selected from the group of Ile (I), Val (V), Leu (L) or Phe (F); and,
- linker is a polypeptide of SEQ ID NO:19; or SEQ ID NO:20.

2. The binding agent according to claim 1, wherein Xaa at position 5 of SEQ ID NO:19 is tyrosine or tryptophan, Xaa at position 12 of SEQ ID NO:19 is phenylalanine or tryptophan, Xaa at position 14 of SEQ ID NO:19 is valine or tryptophan, or a combination thereof.

3. The binding agent according to claim 1, wherein the linker comprises SEQ ID NO: 2, SEQ ID NO: 3, SEQ ID NO: 4 or SEQ ID NO: 5.

4. The binding agent according to claim 1, wherein Xaa at position 1 of SEQ ID NO:20 is serine or threonine, Xaa at position 5 of SEQ ID NO:20 is glutamic acid or asparagine, Xaa at position 6 of SEQ ID NO:20 is glycine, asparagine or D-proline, Xaa at position 7 of SEQ ID NO:20 is asparagine, serine or glycine, Xaa at position 8 of SEQ ID NO:20 is lysine or alanine, Xaa at position 12 of SEQ ID NO:20 is lysine or asparagine, or a combination thereof.

5. The binding agent according to claim 1, wherein the linker comprises SEQ ID NO: 21, SEQ ID NO: 22, SEQ ID NO: 23 or SEQ ID NO: 24.

6. The binding agent according to claim 1, wherein tbm1 comprises (D-Phe)-Pro-Arg, SEQ ID NO: 26, SEQ ID NO: 27, SEQ ID NO: 38 or SEQ ID NO: 70.

7. The binding agent according to claim 1, wherein tbm2 comprises SEQ ID NO: 8, SEQ ID NO: 25, SEQ ID NO: 39, SEQ ID NO: 76, or SEQ ID NO: 77.

8. The binding agent according to claim 1, wherein tbm2 targets fibrinogen-specific exosite I (ES1) of thrombin.

9. The binding agent according to claim 1 comprising SEQ ID NO: 44, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69 or SEQ ID NO: 74.

10. The binding agent according to claim 1 further comprising a nanoparticle to which the linker is linked.

11. The binding agent according to claim 10, wherein the linker is covalently conjugated with or covalently bound to the nanoparticle.

12. A multi-functional thrombin binding agent of formula (I):

tbm1-xRFTD-linker-tbm2     (I)

wherein:
- tbm1 is selected from the group consisting of (d-Phe)-Pro-Arg, SEQ ID NO: 26, SEQ ID NO: 27, SEQ ID NO: 38 and SEQ ID NO: 70;
- xRFTD is a pentapeptide of sequence PRFTD (SEQ ID NO:41) or a pentapeptide of sequence xRFTD (SEQ ID NO:72) where x is selected from the group of Ile (I), Val (V), Leu (L) or Phe (F);
- tbm2 is selected from the group consisting of SEQ ID NO: 8, SEQ ID NO: 25, SEQ ID NO: 39, SEQ ID NO: 76, and SEQ ID NO: 77; and
- linker is a polypeptide comprising SEQ ID NO:19 or SEQ ID NO:20.

13. A method of inhibiting blood coagulation, thrombosis and/or inflammation at a specific site in a bloodstream or tissue of a subject, the method comprising identifying a subject in need of an anti-coagulant, anti-thrombotic or anti-inflammatory agent at the specific site; and, administering to the subject a bivalent thrombin binding agent as defined in claim 1.

14. The method according to claim 13, wherein the subject is human.

15. The method according to claim 13, wherein the subject in need of an anti-coagulant, anti-thrombotic or anti-inflammatory agent suffers from a vascular or tissue lesion, an atherosclerotic plaque, an inflammatory joint disease, pulmonary fibrosis, an inflammatory bowel disease or a cancer.

* * * * *

SEQUENCE LISTING

<160> NUMBER OF SEQ ID NOS: 87

<210> SEQ ID NO 1
<211> LENGTH: 16
<212> TYPE: PRT
<213> ORGANISM: Artificial Sequence
<220> FEATURE:
<223> OTHER INFORMATION: (GS)8 linker

<400> SEQUENCE: 1

Gly Ser Gly Ser Gly Ser Gly Ser Gly Ser Gly Ser Gly Ser Gly Ser
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: gb1 linker

<400> SEQUENCE: 2

Gly Glu Trp Thr Tyr Asp Asp Ala Thr Lys Thr Phe Thr Val Thr Glu
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: trpzip6 linker

<400> SEQUENCE: 3

Gly Glu Trp Thr Trp Asp Asp Ala Thr Lys Thr Trp Thr Val Thr Glu
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: trpzip5 linker

<400> SEQUENCE: 4

Gly Glu Trp Thr Tyr Asp Asp Ala Thr Lys Thr Phe Thr Trp Thr Glu
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: trpzip4 linker

<400> SEQUENCE: 5

Gly Glu Trp Thr Trp Asp Asp Ala Thr Lys Thr Trp Thr Trp Thr Glu
1               5                   10                  15

<210> SEQ ID NO 6
<211> LENGTH: 12
<212> TYPE: PRT
<213> ORGANISM: Artificial Sequence
<220> FEATURE:
<223> OTHER INFORMATION: GEGT(GS)4 linker

<400> SEQUENCE: 6

Gly Glu Gly Thr Gly Ser Gly Ser Gly Ser Gly Ser
1               5                   10

```
<210> SEQ ID NO 7
<211> LENGTH: 5
<212> TYPE: PRT
<213> ORGANISM: Artificial Sequence
<220> FEATURE:
<223> OTHER INFORMATION: Polypeptide targeting the active site of
      thrombin

<400> SEQUENCE: 7

Ile Arg Phe Thr Asp
1               5

<210> SEQ ID NO 8
<211> LENGTH: 12
<212> TYPE: PRT
<213> ORGANISM: Artificial Sequence
<220> FEATURE:
<223> OTHER INFORMATION: Polypeptide targeting the fibrinogen-specific
      exosite I of thrombin

<400> SEQUENCE: 8

Gly Asp Phe Glu Glu Ile Pro Glu Glu Tyr Leu Gln
1               5                   10

<210> SEQ ID NO 9
<211> LENGTH: 31
<212> TYPE: PRT
<213> ORGANISM: Artificial Sequence
<220> FEATURE:
<223> OTHER INFORMATION: BTI1 bivalent thrombin inhibitor
<220> FEATURE:
<221> NAME/KEY: misc_feature
<222> LOCATION: (1)..(1)
<223> OTHER INFORMATION: Xaa is 4-tert-butyl-benzenesulfonyl
<220> FEATURE:
<221> NAME/KEY: misc_feature
<222> LOCATION: (3)..(3)
<223> OTHER INFORMATION: Xaa is D-pipecolic acid

<400> SEQUENCE: 9

Xaa Arg Xaa Gly Ser Gly Ser Gly Ser Gly Ser Gly Ser Gly
1               5                   10                  15

Ser Gly Ser Gly Asp Phe Glu Glu Ile Pro Glu Glu Tyr Leu Gln
                20                  25                  30

<210> SEQ ID NO 10
<211> LENGTH: 31
<212> TYPE: PRT
<213> ORGANISM: Artificial Sequence
<220> FEATURE:
<223> OTHER INFORMATION: BTI2 bivalent thrombin inhibitor
<220> FEATURE:
<221> NAME/KEY: misc_feature
<222> LOCATION: (1)..(1)
<223> OTHER INFORMATION: Xaa is 4-tert-butyl-benzenesulfonyl
<220> FEATURE:
<221> NAME/KEY: misc_feature
<222> LOCATION: (3)..(3)
<223> OTHER INFORMATION: Xaa is D-pipecolic acid

<400> SEQUENCE: 10

Xaa Arg Xaa Gly Glu Trp Thr Tyr Asp Asp Ala Thr Lys Thr Phe Thr
1               5                   10                  15

Val Thr Glu Gly Asp Phe Glu Glu Ile Pro Glu Glu Tyr Leu Gln
                20                  25                  30

<210> SEQ ID NO 11
```

```
<211> LENGTH: 31
<212> TYPE: PRT
<213> ORGANISM: Artificial Sequence
<220> FEATURE:
<223> OTHER INFORMATION: BTI3 bivalent thrmobin inhibitor
<220> FEATURE:
<221> NAME/KEY: misc_feature
<222> LOCATION: (1)..(1)
<223> OTHER INFORMATION: Xaa is 4-tert-butyl-benzenesulfonyl
<220> FEATURE:
<221> NAME/KEY: misc_feature
<222> LOCATION: (3)..(3)
<223> OTHER INFORMATION: Xaa is D-pipecolic acid

<400> SEQUENCE: 11

Xaa Arg Xaa Gly Glu Trp Thr Trp Asp Asp Ala Thr Lys Thr Trp Thr
1               5                   10                  15

Val Thr Glu Gly Asp Phe Glu Glu Ile Pro Glu Glu Tyr Leu Gln
            20                  25                  30

<210> SEQ ID NO 12
<211> LENGTH: 31
<212> TYPE: PRT
<213> ORGANISM: Artificial Sequence
<220> FEATURE:
<223> OTHER INFORMATION: BTI4 bivalent thrombin inhibitor
<220> FEATURE:
<221> NAME/KEY: misc_feature
<222> LOCATION: (1)..(1)
<223> OTHER INFORMATION: Xaa is 4-tert-butyl-benzenesulfonyl
<220> FEATURE:
<221> NAME/KEY: misc_feature
<222> LOCATION: (3)..(3)
<223> OTHER INFORMATION: Xaa is D-pipecolic acid

<400> SEQUENCE: 12

Xaa Arg Xaa Gly Glu Trp Thr Tyr Asp Asp Ala Thr Lys Thr Phe Thr
1               5                   10                  15

Trp Thr Glu Gly Asp Phe Glu Glu Ile Pro Glu Glu Tyr Leu Gln
            20                  25                  30

<210> SEQ ID NO 13
<211> LENGTH: 31
<212> TYPE: PRT
<213> ORGANISM: Artificial Sequence
<220> FEATURE:
<223> OTHER INFORMATION: BTI5 bivalent thrombin inhibitor
<220> FEATURE:
<221> NAME/KEY: misc_feature
<222> LOCATION: (1)..(1)
<223> OTHER INFORMATION: Xaa is 4-tert-butyl-benzenesulfonyl
<220> FEATURE:
<221> NAME/KEY: misc_feature
<222> LOCATION: (3)..(3)
<223> OTHER INFORMATION: Xaa is D-pipecolic acid

<400> SEQUENCE: 13

Xaa Arg Xaa Gly Glu Trp Thr Trp Asp Asp Ala Thr Lys Thr Trp Thr
1               5                   10                  15

Trp Thr Glu Gly Asp Phe Glu Glu Ile Pro Glu Glu Tyr Leu Gln
            20                  25                  30

<210> SEQ ID NO 14
<211> LENGTH: 29
<212> TYPE: PRT
<213> ORGANISM: Artificial Sequence
<220> FEATURE:
<223> OTHER INFORMATION: MH2-GS bivalent thrombin inhibitor

<400> SEQUENCE: 14
```

Ile Arg Phe Thr Asp Gly Glu Gly Thr Gly Ser Gly Ser Gly Ser Gly
1               5                   10                  15

Ser Gly Asp Phe Glu Glu Ile Pro Glu Glu Tyr Leu Gln
            20                  25

<210> SEQ ID NO 15
<211> LENGTH: 33
<212> TYPE: PRT
<213> ORGANISM: Artificial Sequence
<220> FEATURE:
<223> OTHER INFORMATION: MH2-gb1 bivalent thrombin inhibitor

<400> SEQUENCE: 15

Ile Arg Phe Thr Asp Gly Glu Trp Thr Tyr Asp Asp Ala Thr Lys Thr
1               5                   10                  15

Phe Thr Val Thr Glu Gly Asp Phe Glu Glu Ile Pro Glu Glu Tyr Leu
            20                  25                  30

Gln

<210> SEQ ID NO 16
<211> LENGTH: 33
<212> TYPE: PRT
<213> ORGANISM: Artificial Sequence
<220> FEATURE:
<223> OTHER INFORMATION: MH2-trpzip6 bivalent thrombin inhibitor

<400> SEQUENCE: 16

Ile Arg Phe Thr Asp Gly Glu Trp Thr Trp Asp Asp Ala Thr Lys Thr
1               5                   10                  15

Trp Thr Val Thr Glu Gly Asp Phe Glu Glu Ile Pro Glu Glu Tyr Leu
            20                  25                  30

Gln

<210> SEQ ID NO 17
<211> LENGTH: 33
<212> TYPE: PRT
<213> ORGANISM: Artificial Sequence
<220> FEATURE:
<223> OTHER INFORMATION: MH2-trpzip5 bivalent thrombin inhibitor

<400> SEQUENCE: 17

Ile Arg Phe Thr Asp Gly Glu Trp Thr Tyr Asp Asp Ala Thr Lys Thr
1               5                   10                  15

Phe Thr Trp Thr Glu Gly Asp Phe Glu Glu Ile Pro Glu Glu Tyr Leu
            20                  25                  30

Gln

<210> SEQ ID NO 18
<211> LENGTH: 33
<212> TYPE: PRT
<213> ORGANISM: Artificial Sequence
<220> FEATURE:
<223> OTHER INFORMATION: MH2-trpzip4 bivalent thrombin inhibitor

<400> SEQUENCE: 18

Ile Arg Phe Thr Asp Gly Glu Trp Thr Trp Asp Asp Ala Thr Lys Thr
1               5                   10                  15

Trp Thr Trp Thr Glu Gly Asp Phe Glu Glu Ile Pro Glu Glu Tyr Leu
            20                  25                  30

Gln

```
<210> SEQ ID NO 19
<211> LENGTH: 16
<212> TYPE: PRT
<213> ORGANISM: Artificial Sequence
<220> FEATURE:
<223> OTHER INFORMATION: Linker
<220> FEATURE:
<221> NAME/KEY: misc_feature
<222> LOCATION: (5)..(5)
<223> OTHER INFORMATION: Xaa is any amino acid.
<220> FEATURE:
<221> NAME/KEY: misc_feature
<222> LOCATION: (12)..(12)
<223> OTHER INFORMATION: Xaa is any amino acid.
<220> FEATURE:
<221> NAME/KEY: misc_feature
<222> LOCATION: (14)..(14)
<223> OTHER INFORMATION: Xaa is any amino acid.

<400> SEQUENCE: 19

Gly Glu Trp Thr Xaa Asp Asp Ala Thr Lys Thr Xaa Thr Xaa Thr Glu
1               5                   10                  15

<210> SEQ ID NO 20
<211> LENGTH: 12
<212> TYPE: PRT
<213> ORGANISM: Artificial Sequence
<220> FEATURE:
<223> OTHER INFORMATION: Linker
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: MISC_FEATURE
<222> LOCATION: (5)..(8)
<223> OTHER INFORMATION: Xaa is any amino acid
<220> FEATURE:
<221> NAME/KEY: MISC_FEATURE
<222> LOCATION: (12)..(12)
<223> OTHER INFORMATION: Xaa is any amino acid

<400> SEQUENCE: 20

Xaa Trp Thr Trp Xaa Xaa Xaa Xaa Trp Thr Trp Xaa
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Linker

<400> SEQUENCE: 21

Ser Trp Thr Trp Glu Gly Asn Lys Trp Thr Trp Lys
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Linker

<400> SEQUENCE: 22

Thr Trp Thr Trp Asn Gly Ser Ala Trp Thr Trp Asn
1               5                   10

<210> SEQ ID NO 23
<211> LENGTH: 12
```

```
<212> TYPE: PRT
<213> ORGANISM: Artificial Sequence
<220> FEATURE:
<223> OTHER INFORMATION: Linker

<400> SEQUENCE: 23

Ser Trp Thr Trp Glu Asn Gly Lys Trp Thr Trp Lys
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Linker
<220> FEATURE:
<221> NAME/KEY: MISC_FEATURE
<222> LOCATION: (6)..(6)
<223> OTHER INFORMATION: Pro is D-proline

<400> SEQUENCE: 24

Ser Trp Thr Trp Glu Pro Asn Lys Trp Thr Trp Lys
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Polypeptide targeting fibrinogen-specific
      exosite I of thrombin

<400> SEQUENCE: 25

Gly Asp Phe Glu Glu Ile Pro Glu Glu Tyr Leu
1               5                   10

<210> SEQ ID NO 26
<211> LENGTH: 4
<212> TYPE: PRT
<213> ORGANISM: Artificial Sequence
<220> FEATURE:
<223> OTHER INFORMATION: Polypeptide targeting active site of thrombin

<400> SEQUENCE: 26

Phe Gln Pro Arg
1

<210> SEQ ID NO 27
<211> LENGTH: 4
<212> TYPE: PRT
<213> ORGANISM: Artificial Sequence
<220> FEATURE:
<223> OTHER INFORMATION: Polypeptide targeting active site of thrombin

<400> SEQUENCE: 27

Trp Asp Pro Arg
1

<210> SEQ ID NO 28
<211> LENGTH: 29
<212> TYPE: PRT
<213> ORGANISM: Artificial Sequence
<220> FEATURE:
<223> OTHER INFORMATION: Linker + tbm2 from BTI1

<400> SEQUENCE: 28

Cys Gly Ser Gly Ser Gly Ser Gly Ser Gly Ser Gly Ser Gly Ser Gly
1               5                   10                  15
```

Ser Gly Asp Phe Glu Glu Ile Pro Glu Glu Tyr Leu Gln
            20                  25

<210> SEQ ID NO 29
<211> LENGTH: 6
<212> TYPE: PRT
<213> ORGANISM: Artificial Sequence
<220> FEATURE:
<223> OTHER INFORMATION: Polypeptide targeting active site of thrombin

<400> SEQUENCE: 29

Ile Arg Phe Thr Asp Gly
1               5

<210> SEQ ID NO 30
<211> LENGTH: 12
<212> TYPE: PRT
<213> ORGANISM: Artificial Sequence
<220> FEATURE:
<223> OTHER INFORMATION: Linker fragment from mini-huridin 2

<400> SEQUENCE: 30

Gly Glu Gly Thr Pro Asn Pro Glu Ser His Asn Asn
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Linker

<400> SEQUENCE: 31

Gly Ser Gly Ser Gly Ser Gly Ser Gly Ser Gly Ser
1               5                   10

<210> SEQ ID NO 32
<211> LENGTH: 16
<212> TYPE: PRT
<213> ORGANISM: Artificial Sequence
<220> FEATURE:
<223> OTHER INFORMATION: Linker

<400> SEQUENCE: 32

Gly Glu Gly Thr Gly Ser Gly Ser Gly Ser Gly Ser Gly Ser Gly Ser
1               5                   10                  15

<210> SEQ ID NO 33
<211> LENGTH: 29
<212> TYPE: PRT
<213> ORGANISM: Artificial Sequence
<220> FEATURE:
<223> OTHER INFORMATION: MH1 - bivalent thrombin inhibitor

<400> SEQUENCE: 33

Val Arg Phe Thr Asp Gly Glu Gly Thr Pro Lys Pro Gln Ser His Asp
1               5                   10                  15

Asn Gly Asp Phe Glu Glu Ile Pro Glu Glu Tyr Leu Gln
            20                  25

<210> SEQ ID NO 34
<211> LENGTH: 29
<212> TYPE: PRT
<213> ORGANISM: Artificial Sequence
<220> FEATURE:
<223> OTHER INFORMATION: MH2 - bivalent thrombin inhibitor

<400> SEQUENCE: 34

Ile Arg Phe Thr Asp Gly Glu Gly Thr Pro Asn Pro Glu Ser His Asn
1               5                   10                  15

Asn Gly Asp Phe Glu Glu Ile Pro Glu Glu Tyr Leu Gln
            20                  25

<210> SEQ ID NO 35
<211> LENGTH: 29
<212> TYPE: PRT
<213> ORGANISM: Artificial Sequence
<220> FEATURE:
<223> OTHER INFORMATION: MH2-allGS - bivalent thrombin inhibitor

<400> SEQUENCE: 35

Ile Arg Phe Thr Asp Gly Ser Gly Ser Gly Ser Gly Ser Gly Ser Gly
1               5                   10                  15

Ser Gly Asp Phe Glu Glu Ile Pro Glu Glu Tyr Leu Gln
            20                  25

<210> SEQ ID NO 36
<211> LENGTH: 33
<212> TYPE: PRT
<213> ORGANISM: Artificial Sequence
<220> FEATURE:
<223> OTHER INFORMATION: MH2-longGS - bivalent thrombin inhibitor

<400> SEQUENCE: 36

Ile Arg Phe Thr Asp Gly Glu Gly Thr Gly Ser Gly Ser Gly Ser Gly
1               5                   10                  15

Ser Gly Ser Gly Ser Gly Asp Phe Glu Glu Ile Pro Glu Glu Tyr Leu
            20                  25                  30

Gln

<210> SEQ ID NO 37
<211> LENGTH: 18
<212> TYPE: PRT
<213> ORGANISM: Artificial Sequence
<220> FEATURE:
<223> OTHER INFORMATION: Linker
<220> FEATURE:
<221> NAME/KEY: DISULFID
<222> LOCATION: (1)..(2)
<223> OTHER INFORMATION: Cysteine residues linked by disulfide bond

<400> SEQUENCE: 37

Cys Cys Gly Ser Gly Ser Gly Ser Gly Ser Gly Ser Gly Ser Gly Ser
1               5                   10                  15

Gly Ser

<210> SEQ ID NO 38
<211> LENGTH: 4
<212> TYPE: PRT
<213> ORGANISM: Artificial Sequence
<220> FEATURE:
<223> OTHER INFORMATION: 4 aa polypeptide

<400> SEQUENCE: 38

Ile Gln Pro Arg
1

<210> SEQ ID NO 39
<211> LENGTH: 11
<212> TYPE: PRT

<213> ORGANISM: Artificial Sequence
<220> FEATURE:
<223> OTHER INFORMATION: 11 aa polypeptide segment of SEQ ID NO: 8

<400> SEQUENCE: 39

Asp Phe Glu Glu Ile Pro Glu Glu Tyr Leu Gln
1               5                   10

<210> SEQ ID NO 40
<211> LENGTH: 37
<212> TYPE: PRT
<213> ORGANISM: Artificial Sequence
<220> FEATURE:
<223> OTHER INFORMATION: Covalently blocked MH2-trpzip4
<220> FEATURE:
<221> NAME/KEY: MISC_FEATURE
<222> LOCATION: (1)..(4)
<223> OTHER INFORMATION: Xaa is any amino acid

<400> SEQUENCE: 40

Xaa Xaa Xaa Xaa Ile Arg Phe Thr Asp Gly Glu Trp Thr Trp Asp Asp
1               5                   10                  15

Ala Thr Lys Thr Trp Thr Trp Thr Glu Gly Asp Phe Glu Glu Ile Pro
            20                  25                  30

Glu Glu Tyr Leu Gln
        35

<210> SEQ ID NO 41
<211> LENGTH: 5
<212> TYPE: PRT
<213> ORGANISM: Artificial Sequence
<220> FEATURE:
<223> OTHER INFORMATION: Polypeptide targeting active site of thrombin

<400> SEQUENCE: 41

Pro Arg Phe Thr Asp
1               5

<210> SEQ ID NO 42
<211> LENGTH: 5
<212> TYPE: PRT
<213> ORGANISM: Artificial Sequence
<220> FEATURE:
<223> OTHER INFORMATION: 5 aa polypeptide

<400> SEQUENCE: 42

Val Arg Phe Thr Asp
1               5

<210> SEQ ID NO 43
<211> LENGTH: 4
<212> TYPE: PRT
<213> ORGANISM: Artificial Sequence
<220> FEATURE:
<223> OTHER INFORMATION: 4 aa polypeptide

<400> SEQUENCE: 43

Ile Glu Gly Arg
1

<210> SEQ ID NO 44
<211> LENGTH: 36
<212> TYPE: PRT
<213> ORGANISM: Artificial Sequence
<220> FEATURE:
<223> OTHER INFORMATION: BRI-T207 bivalent thrombin inhibitor

```
<400> SEQUENCE: 44

Phe Gln Pro Arg Pro Arg Phe Thr Asp Gly Glu Trp Thr Trp Asp Asp
1               5                   10                  15

Ala Thr Lys Thr Trp Thr Trp Thr Glu Gly Asp Phe Glu Glu Ile Pro
            20                  25                  30

Glu Glu Tyr Leu
        35

<210> SEQ ID NO 45
<211> LENGTH: 33
<212> TYPE: PRT
<213> ORGANISM: Artificial Sequence
<220> FEATURE:
<223> OTHER INFORMATION: BRI-T109 bivalent thrombin inhibitor

<400> SEQUENCE: 45

Pro Arg Phe Thr Asp Gly Glu Trp Thr Trp Asp Asp Ala Thr Lys Thr
1               5                   10                  15

Trp Thr Trp Thr Glu Gly Asp Phe Glu Glu Ile Pro Glu Glu Tyr Leu
            20                  25                  30

Gln

<210> SEQ ID NO 46
<211> LENGTH: 32
<212> TYPE: PRT
<213> ORGANISM: Artificial Sequence
<220> FEATURE:
<223> OTHER INFORMATION: BRI-T110 bivalent thrombin inhibitor

<400> SEQUENCE: 46

Pro Arg Phe Thr Asp Gly Glu Trp Thr Trp Asp Asp Ala Thr Lys Thr
1               5                   10                  15

Trp Thr Trp Thr Glu Gly Asp Phe Glu Glu Ile Pro Glu Glu Tyr Leu
            20                  25                  30

<210> SEQ ID NO 47
<211> LENGTH: 32
<212> TYPE: PRT
<213> ORGANISM: Artificial Sequence
<220> FEATURE:
<223> OTHER INFORMATION: BRI-T111 bivalent thrombin inhibitor

<400> SEQUENCE: 47

Ile Arg Phe Thr Asp Gly Glu Trp Thr Trp Asp Asp Ala Thr Lys Thr
1               5                   10                  15

Trp Thr Trp Thr Glu Gly Asp Phe Glu Glu Ile Pro Glu Glu Tyr Leu
            20                  25                  30

<210> SEQ ID NO 48
<211> LENGTH: 31
<212> TYPE: PRT
<213> ORGANISM: Artificial Sequence
<220> FEATURE:
<223> OTHER INFORMATION: BRI-T113 bivalent thrombin inhibitor
<220> FEATURE:
<221> NAME/KEY: MISC_FEATURE
<222> LOCATION: (1)..(1)
<223> OTHER INFORMATION: Phe is D-phenylalanine

<400> SEQUENCE: 48

Phe Pro Arg Pro Gly Glu Trp Thr Trp Asp Asp Ala Thr Lys Thr Trp
1               5                   10                  15

Thr Trp Thr Glu Gly Asp Phe Glu Glu Ile Pro Glu Glu Tyr Leu
```

<210> SEQ ID NO 49
<211> LENGTH: 36
<212> TYPE: PRT
<213> ORGANISM: Artificial Sequence
<220> FEATURE:
<223> OTHER INFORMATION: BRI-T204 bivalent thrombin inhibitor

<400> SEQUENCE: 49

Ile Glu Gly Arg Ile Arg Phe Thr Asp Gly Glu Trp Thr Trp Asp Asp
1               5                   10                  15

Ala Thr Lys Thr Trp Thr Trp Thr Glu Gly Asp Phe Glu Glu Ile Pro
            20                  25                  30

Glu Glu Tyr Leu
        35

<210> SEQ ID NO 50
<211> LENGTH: 36
<212> TYPE: PRT
<213> ORGANISM: Artificial Sequence
<220> FEATURE:
<223> OTHER INFORMATION: BRI-T205 bivalent thrombin inhibitor

<400> SEQUENCE: 50

Ile Glu Gly Arg Ile Arg Phe Thr Asp Gly Glu Trp Thr Tyr Asp Asp
1               5                   10                  15

Ala Thr Lys Thr Phe Thr Trp Thr Glu Gly Asp Phe Glu Glu Ile Pro
            20                  25                  30

Glu Glu Tyr Leu
        35

<210> SEQ ID NO 51
<211> LENGTH: 36
<212> TYPE: PRT
<213> ORGANISM: Artificial Sequence
<220> FEATURE:
<223> OTHER INFORMATION: BRI-T217 bivalent thrombin inhibitor

<400> SEQUENCE: 51

Phe Gln Pro Arg Ile Arg Phe Thr Asp Gly Glu Trp Thr Trp Asp Asp
1               5                   10                  15

Ala Thr Lys Thr Trp Thr Trp Thr Glu Gly Asp Phe Glu Glu Ile Pro
            20                  25                  30

Glu Glu Tyr Leu
        35

<210> SEQ ID NO 52
<211> LENGTH: 36
<212> TYPE: PRT
<213> ORGANISM: Artificial Sequence
<220> FEATURE:
<223> OTHER INFORMATION: BRI-T227 bivalent thrombin inhibitor

<400> SEQUENCE: 52

Phe Gln Pro Arg Val Arg Phe Thr Asp Gly Glu Trp Thr Trp Asp Asp
1               5                   10                  15

Ala Thr Lys Thr Trp Thr Trp Thr Glu Gly Asp Phe Glu Glu Ile Pro
            20                  25                  30

Glu Glu Tyr Leu
        35

```
<210> SEQ ID NO 53
<211> LENGTH: 36
<212> TYPE: PRT
<213> ORGANISM: Artificial Sequence
<220> FEATURE:
<223> OTHER INFORMATION: BRI-T237 bivalent thrombin inhibitor

<400> SEQUENCE: 53

Phe Gln Pro Arg Leu Arg Phe Thr Asp Gly Glu Trp Thr Trp Asp Asp
1               5                   10                  15

Ala Thr Lys Thr Trp Thr Trp Thr Glu Gly Asp Phe Glu Glu Ile Pro
            20                  25                  30

Glu Glu Tyr Leu
        35

<210> SEQ ID NO 54
<211> LENGTH: 36
<212> TYPE: PRT
<213> ORGANISM: Artificial Sequence
<220> FEATURE:
<223> OTHER INFORMATION: BRI-T247 bivalent thrombin inhibitor

<400> SEQUENCE: 54

Phe Gln Pro Arg Phe Arg Phe Thr Asp Gly Glu Trp Thr Trp Asp Asp
1               5                   10                  15

Ala Thr Lys Thr Trp Thr Trp Thr Glu Gly Asp Phe Glu Glu Ile Pro
            20                  25                  30

Glu Glu Tyr Leu
        35

<210> SEQ ID NO 55
<211> LENGTH: 35
<212> TYPE: PRT
<213> ORGANISM: Artificial Sequence
<220> FEATURE:
<223> OTHER INFORMATION: BRI-T208 bivalent thrombin inhibitor
<220> FEATURE:
<221> NAME/KEY: MISC_FEATURE
<222> LOCATION: (1)..(1)
<223> OTHER INFORMATION: Phe is D-phenylalanine

<400> SEQUENCE: 55

Phe Pro Arg Pro Arg Phe Thr Asp Gly Glu Trp Thr Trp Asp Asp Ala
1               5                   10                  15

Thr Lys Thr Trp Thr Trp Thr Glu Gly Asp Phe Glu Glu Ile Pro Glu
            20                  25                  30

Glu Tyr Leu
        35

<210> SEQ ID NO 56
<211> LENGTH: 35
<212> TYPE: PRT
<213> ORGANISM: Artificial Sequence
<220> FEATURE:
<223> OTHER INFORMATION: BRI-T218 bivalent thrombin inhibitor
<220> FEATURE:
<221> NAME/KEY: MISC_FEATURE
<222> LOCATION: (1)..(1)
<223> OTHER INFORMATION: Phe is D-phenylalanine

<400> SEQUENCE: 56

Phe Pro Arg Ile Arg Phe Thr Asp Gly Glu Trp Thr Trp Asp Asp Ala
1               5                   10                  15

Thr Lys Thr Trp Thr Trp Thr Glu Gly Asp Phe Glu Glu Ile Pro Glu
            20                  25                  30
```

Glu Tyr Leu
        35

<210> SEQ ID NO 57
<211> LENGTH: 35
<212> TYPE: PRT
<213> ORGANISM: Artificial Sequence
<220> FEATURE:
<223> OTHER INFORMATION: BRI-T228 bivalent thrombin inhibitor
<220> FEATURE:
<221> NAME/KEY: MISC_FEATURE
<222> LOCATION: (1)..(1)
<223> OTHER INFORMATION: Phe is D-phenylalanine

<400> SEQUENCE: 57

Phe Pro Arg Val Arg Phe Thr Asp Gly Glu Trp Thr Trp Asp Asp Ala
1               5                   10                  15

Thr Lys Thr Trp Thr Trp Thr Glu Gly Asp Phe Glu Glu Ile Pro Glu
            20                  25                  30

Glu Tyr Leu
        35

<210> SEQ ID NO 58
<211> LENGTH: 35
<212> TYPE: PRT
<213> ORGANISM: Artificial Sequence
<220> FEATURE:
<223> OTHER INFORMATION: BRI-T238 bivalent thrombin inhibitor
<220> FEATURE:
<221> NAME/KEY: MISC_FEATURE
<222> LOCATION: (1)..(1)
<223> OTHER INFORMATION: Phe is D-phenylalanine

<400> SEQUENCE: 58

Phe Pro Arg Leu Arg Phe Thr Asp Gly Glu Trp Thr Trp Asp Asp Ala
1               5                   10                  15

Thr Lys Thr Trp Thr Trp Thr Glu Gly Asp Phe Glu Glu Ile Pro Glu
            20                  25                  30

Glu Tyr Leu
        35

<210> SEQ ID NO 59
<211> LENGTH: 35
<212> TYPE: PRT
<213> ORGANISM: Artificial Sequence
<220> FEATURE:
<223> OTHER INFORMATION: BRI-T248 bivalent thrombin inhibitor
<220> FEATURE:
<221> NAME/KEY: MISC_FEATURE
<222> LOCATION: (1)..(1)
<223> OTHER INFORMATION: Phe is D-phenylalanine

<400> SEQUENCE: 59

Phe Pro Arg Phe Arg Phe Thr Asp Gly Glu Trp Thr Trp Asp Asp Ala
1               5                   10                  15

Thr Lys Thr Trp Thr Trp Thr Glu Gly Asp Phe Glu Glu Ile Pro Glu
            20                  25                  30

Glu Tyr Leu
        35

<210> SEQ ID NO 60
<211> LENGTH: 36
<212> TYPE: PRT
<213> ORGANISM: Artificial Sequence
<220> FEATURE:

<223> OTHER INFORMATION: BRI-T209 bivalent thrombin inhibitor

<400> SEQUENCE: 60

Trp Asp Pro Arg Pro Arg Phe Thr Asp Gly Glu Trp Thr Trp Asp Asp
1               5                   10                  15

Ala Thr Lys Thr Trp Thr Trp Thr Glu Gly Asp Phe Glu Glu Ile Pro
            20                  25                  30

Glu Glu Tyr Leu
        35

<210> SEQ ID NO 61
<211> LENGTH: 36
<212> TYPE: PRT
<213> ORGANISM: Artificial Sequence
<220> FEATURE:
<223> OTHER INFORMATION: BRI-T219 bivalent thrombin inhibitor

<400> SEQUENCE: 61

Trp Asp Pro Arg Ile Arg Phe Thr Asp Gly Glu Trp Thr Trp Asp Asp
1               5                   10                  15

Ala Thr Lys Thr Trp Thr Trp Thr Glu Gly Asp Phe Glu Glu Ile Pro
            20                  25                  30

Glu Glu Tyr Leu
        35

<210> SEQ ID NO 62
<211> LENGTH: 36
<212> TYPE: PRT
<213> ORGANISM: Artificial Sequence
<220> FEATURE:
<223> OTHER INFORMATION: BRI-T229 bivalent thrombin inhibitor

<400> SEQUENCE: 62

Trp Asp Pro Arg Val Arg Phe Thr Asp Gly Glu Trp Thr Trp Asp Asp
1               5                   10                  15

Ala Thr Lys Thr Trp Thr Trp Thr Glu Gly Asp Phe Glu Glu Ile Pro
            20                  25                  30

Glu Glu Tyr Leu
        35

<210> SEQ ID NO 63
<211> LENGTH: 36
<212> TYPE: PRT
<213> ORGANISM: Artificial Sequence
<220> FEATURE:
<223> OTHER INFORMATION: BRI-T239 bivalent thrombin inhibitor

<400> SEQUENCE: 63

Trp Asp Pro Arg Leu Arg Phe Thr Asp Gly Glu Trp Thr Trp Asp Asp
1               5                   10                  15

Ala Thr Lys Thr Trp Thr Trp Thr Glu Gly Asp Phe Glu Glu Ile Pro
            20                  25                  30

Glu Glu Tyr Leu
        35

<210> SEQ ID NO 64
<211> LENGTH: 36
<212> TYPE: PRT
<213> ORGANISM: Artificial Sequence
<220> FEATURE:
<223> OTHER INFORMATION: BRI-T249 bivalent thrombin inhibitor

<400> SEQUENCE: 64

Trp Asp Pro Arg Phe Arg Phe Thr Asp Gly Glu Trp Thr Trp Asp Asp
1               5                   10                  15

Ala Thr Lys Thr Trp Thr Trp Thr Glu Gly Asp Phe Glu Glu Ile Pro
            20                  25                  30

Glu Glu Tyr Leu
        35

<210> SEQ ID NO 65
<211> LENGTH: 35
<212> TYPE: PRT
<213> ORGANISM: Artificial Sequence
<220> FEATURE:
<223> OTHER INFORMATION: BRI-T210 bivalent thrombin inhibitor
<220> FEATURE:
<221> NAME/KEY: MISC_FEATURE
<222> LOCATION: (1)..(1)
<223> OTHER INFORMATION: Phe is D-phenylalanine

<400> SEQUENCE: 65

Phe Pro Arg Pro Arg Phe Thr Asp Gly Glu Trp Thr Tyr Asp Asp Ala
1               5                   10                  15

Thr Lys Thr Phe Thr Trp Thr Glu Gly Asp Phe Glu Glu Ile Pro Glu
            20                  25                  30

Glu Tyr Leu
        35

<210> SEQ ID NO 66
<211> LENGTH: 35
<212> TYPE: PRT
<213> ORGANISM: Artificial Sequence
<220> FEATURE:
<223> OTHER INFORMATION: BRI-T220 bivalent thrombin inhibitor
<220> FEATURE:
<221> NAME/KEY: MISC_FEATURE
<222> LOCATION: (1)..(1)
<223> OTHER INFORMATION: Phe is D-phenylalanine

<400> SEQUENCE: 66

Phe Pro Arg Ile Arg Phe Thr Asp Gly Glu Trp Thr Tyr Asp Asp Ala
1               5                   10                  15

Thr Lys Thr Phe Thr Trp Thr Glu Gly Asp Phe Glu Glu Ile Pro Glu
            20                  25                  30

Glu Tyr Leu
        35

<210> SEQ ID NO 67
<211> LENGTH: 35
<212> TYPE: PRT
<213> ORGANISM: Artificial Sequence
<220> FEATURE:
<223> OTHER INFORMATION: BRI-T230 bivalent thrombin inhibitor
<220> FEATURE:
<221> NAME/KEY: MISC_FEATURE
<222> LOCATION: (1)..(1)
<223> OTHER INFORMATION: Phe is D-phenylalanine

<400> SEQUENCE: 67

Phe Pro Arg Val Arg Phe Thr Asp Gly Glu Trp Thr Tyr Asp Asp Ala
1               5                   10                  15

Thr Lys Thr Phe Thr Trp Thr Glu Gly Asp Phe Glu Glu Ile Pro Glu
            20                  25                  30

Glu Tyr Leu
        35

```
<210> SEQ ID NO 68
<211> LENGTH: 35
<212> TYPE: PRT
<213> ORGANISM: Artificial Sequence
<220> FEATURE:
<223> OTHER INFORMATION: BRI-T240 bivalent thrombin inhibitor
<220> FEATURE:
<221> NAME/KEY: MISC_FEATURE
<222> LOCATION: (1)..(1)
<223> OTHER INFORMATION: Phe is D-phenylalanine

<400> SEQUENCE: 68

Phe Pro Arg Leu Arg Phe Thr Asp Gly Glu Trp Thr Tyr Asp Asp Ala
1               5                   10                  15

Thr Lys Thr Phe Thr Trp Thr Glu Gly Asp Phe Glu Glu Ile Pro Glu
            20                  25                  30

Glu Tyr Leu
        35

<210> SEQ ID NO 69
<211> LENGTH: 35
<212> TYPE: PRT
<213> ORGANISM: Artificial Sequence
<220> FEATURE:
<223> OTHER INFORMATION: BRI-T250 bivalent thrombin inhibitor
<220> FEATURE:
<221> NAME/KEY: MISC_FEATURE
<222> LOCATION: (1)..(1)
<223> OTHER INFORMATION: Phe is D-phenylalanine

<400> SEQUENCE: 69

Phe Pro Arg Phe Arg Phe Thr Asp Gly Glu Trp Thr Tyr Asp Asp Ala
1               5                   10                  15

Thr Lys Thr Phe Thr Trp Thr Glu Gly Asp Phe Glu Glu Ile Pro Glu
            20                  25                  30

Glu Tyr Leu
        35

<210> SEQ ID NO 70
<211> LENGTH: 4
<212> TYPE: PRT
<213> ORGANISM: Artificial Sequence
<220> FEATURE:
<223> OTHER INFORMATION: 4 aa polypeptide

<400> SEQUENCE: 70

Phe Asn Pro Arg
1

<210> SEQ ID NO 71
<211> LENGTH: 5
<212> TYPE: PRT
<213> ORGANISM: Artificial Sequence
<220> FEATURE:
<223> OTHER INFORMATION: 5 aa linker segment (Gly)4-Asn

<400> SEQUENCE: 71

Gly Gly Gly Gly Asn
1               5

<210> SEQ ID NO 72
<211> LENGTH: 5
<212> TYPE: PRT
<213> ORGANISM: Artificial Sequence
<220> FEATURE:
<223> OTHER INFORMATION: 5 aa polypeptide targeting active site of
```

```
      thrombin
<220> FEATURE:
<221> NAME/KEY: MISC_FEATURE
<222> LOCATION: (1)..(1)
<223> OTHER INFORMATION: Xaa is isoleucine, valine, leucine or
      phenylalanine

<400> SEQUENCE: 72

Xaa Arg Phe Thr Asp
1               5

<210> SEQ ID NO 73
<211> LENGTH: 8
<212> TYPE: PRT
<213> ORGANISM: Artificial Sequence
<220> FEATURE:
<223> OTHER INFORMATION: 8 aa polypeptide targeting active site of
      thrombin
<220> FEATURE:
<221> NAME/KEY: MISC_FEATURE
<222> LOCATION: (4)..(4)
<223> OTHER INFORMATION: Xaa is isoleucine, valine, leucine or
      phenylalanine

<400> SEQUENCE: 73

Phe Pro Arg Xaa Arg Phe Thr Asp
1               5

<210> SEQ ID NO 74
<211> LENGTH: 35
<212> TYPE: PRT
<213> ORGANISM: Artificial Sequence
<220> FEATURE:
<223> OTHER INFORMATION: bivalent thrombin inhibitor
<220> FEATURE:
<221> NAME/KEY: MISC_FEATURE
<222> LOCATION: (4)..(4)
<223> OTHER INFORMATION: Xaa is isoleucine, valine, leucine or
      phenylalanine

<400> SEQUENCE: 74

Phe Pro Arg Xaa Arg Phe Thr Asp Gly Glu Trp Thr Trp Asp Asp Ala
1               5                   10                  15

Thr Lys Thr Trp Thr Trp Thr Glu Gly Asp Phe Glu Glu Ile Pro Glu
            20                  25                  30

Glu Tyr Leu
        35

<210> SEQ ID NO 75
<211> LENGTH: 21
<212> TYPE: PRT
<213> ORGANISM: Artificial Sequence
<220> FEATURE:
<223> OTHER INFORMATION: Fragment of bivalent thrombin inhibitor

<400> SEQUENCE: 75

Ile Arg Phe Thr Asp Gly Glu Trp Thr Trp Asp Asp Ala Thr Lys Thr
1               5                   10                  15

Trp Thr Trp Thr Glu
            20

<210> SEQ ID NO 76
<211> LENGTH: 12
<212> TYPE: PRT
<213> ORGANISM: Artificial Sequence
<220> FEATURE:
<223> OTHER INFORMATION: 12 aa haemadin C-terminus specific for AB2 of
      thrombin
```

<400> SEQUENCE: 76

Glu Phe Glu Glu Phe Glu Ile Asp Glu Glu Glu Lys
1               5                   10

<210> SEQ ID NO 77
<211> LENGTH: 131
<212> TYPE: PRT
<213> ORGANISM: Artificial Sequence
<220> FEATURE:
<223> OTHER INFORMATION: PEPA1 - 131 aa human VH domain binder for
      PPACK-thrombin

<400> SEQUENCE: 77

Glu Val Gln Leu Gln Ala Ser Gly Gly Gly Leu Val Gln Ser Gly Asp
1               5                   10                  15

Ser Leu Arg Leu Ser Cys Ala Ala Ser Gly Arg Thr Phe Ser Thr Tyr
            20                  25                  30

Ala Met Gly Trp Phe Arg Gln Ala Pro Gly Lys Leu Arg Glu Phe Val
        35                  40                  45

Gly Val Ile Ser Ser Ser Gly Tyr Thr His Tyr Thr Asn Ser Val Arg
    50                  55                  60

Gly Arg Phe Thr Ile Ser Arg Asp Asn Ala Lys Asn Met Val Tyr Leu
65                  70                  75                  80

Gln Met Asn Ser Leu Lys Pro Glu Asp Thr Ala Val Tyr Tyr Cys Ala
                85                  90                  95

Ala Ala Asp Arg Arg Phe Ile Ala Thr Asp Gly Lys Gln Tyr Asp Tyr
            100                 105                 110

Trp Gly Gln Gly Thr Gln Val Thr Val Ser Ser Leu Glu His His His
        115                 120                 125

His His His
        130

<210> SEQ ID NO 78
<211> LENGTH: 34
<212> TYPE: PRT
<213> ORGANISM: Artificial Sequence
<220> FEATURE:
<223> OTHER INFORMATION: BRI-T304 bivalent thrombin inhibitor

<400> SEQUENCE: 78

Ile Arg Phe Thr Asp Gly Glu Trp Thr Trp Asp Asp Ala Thr Lys Thr
1               5                   10                  15

Trp Thr Trp Thr Glu Gly Glu Phe Glu Glu Phe Glu Ile Asp Glu Glu
            20                  25                  30

Glu Lys

<210> SEQ ID NO 79
<211> LENGTH: 155
<212> TYPE: PRT
<213> ORGANISM: Artificial Sequence
<220> FEATURE:
<223> OTHER INFORMATION: BRI-T404 bivalent thrombin inhibitor

<400> SEQUENCE: 79

Ile Arg Phe Thr Asp Gly Glu Trp Thr Trp Asp Asp Ala Thr Lys Thr
1               5                   10                  15

Trp Thr Trp Thr Glu Gly Gly Ser Glu Val Gln Leu Gln Ala Ser Gly
            20                  25                  30

Gly Gly Leu Val Gln Ser Gly Asp Ser Leu Arg Leu Ser Cys Ala Ala

```
                35                  40                  45
Ser Gly Arg Thr Phe Ser Thr Tyr Ala Met Gly Trp Phe Arg Gln Ala
 50                  55                  60

Pro Gly Lys Leu Arg Glu Phe Val Gly Val Ile Ser Ser Ser Gly Tyr
65                  70                  75                  80

Thr His Tyr Thr Asn Ser Val Arg Gly Arg Phe Thr Ile Ser Arg Asp
                85                  90                  95

Asn Ala Lys Asn Met Val Tyr Leu Gln Met Asn Ser Leu Lys Pro Glu
                100                 105                 110

Asp Thr Ala Val Tyr Tyr Cys Ala Ala Ala Asp Arg Arg Phe Ile Ala
                115                 120                 125

Thr Asp Gly Lys Gln Tyr Asp Tyr Trp Gly Gln Gly Thr Gln Val Thr
            130                 135                 140

Val Ser Ser Leu Glu His His His His His
145                 150                 155

<210> SEQ ID NO 80
<211> LENGTH: 148
<212> TYPE: PRT
<213> ORGANISM: Artificial Sequence
<220> FEATURE:
<223> OTHER INFORMATION: VSL-PEPA1

<400> SEQUENCE: 80

Gly Ser Val Ser Pro Arg Pro Gln Leu His Asn Asp Gly Gly Gly Ser
1               5                   10                  15

Ser Glu Val Gln Leu Gln Ala Ser Gly Gly Gly Leu Val Gln Ser Gly
                20                  25                  30

Asp Ser Leu Arg Leu Ser Cys Ala Ala Ser Gly Arg Thr Phe Ser Thr
                35                  40                  45

Tyr Ala Met Gly Trp Phe Arg Gln Ala Pro Gly Lys Leu Arg Glu Phe
 50                  55                  60

Val Gly Val Ile Ser Ser Ser Gly Tyr Thr His Tyr Thr Asn Ser Val
65                  70                  75                  80

Arg Gly Arg Phe Thr Ile Ser Arg Asp Asn Ala Lys Asn Met Val Tyr
                85                  90                  95

Leu Gln Met Asn Ser Leu Lys Pro Glu Asp Thr Ala Val Tyr Tyr Cys
                100                 105                 110

Ala Ala Ala Asp Arg Arg Phe Ile Ala Thr Asp Gly Lys Gln Tyr Asp
            115                 120                 125

Tyr Trp Gly Gln Gly Thr Gln Val Thr Val Ser Ser Leu Glu His His
            130                 135                 140

His His His His
145

<210> SEQ ID NO 81
<211> LENGTH: 22
<212> TYPE: PRT
<213> ORGANISM: Artificial Sequence
<220> FEATURE:
<223> OTHER INFORMATION: 22 amino acid fragment of bivalent thrombin
      inhibitor

<400> SEQUENCE: 81

Ile Arg Phe Thr Asp Gly Glu Trp Thr Trp Asp Asp Ala Thr Lys Thr
1               5                   10                  15

Trp Thr Trp Thr Glu Gly
                20
```

<210> SEQ ID NO 82
<211> LENGTH: 32
<212> TYPE: PRT
<213> ORGANISM: Artificial Sequence
<220> FEATURE:
<223> OTHER INFORMATION: bivalent thrombin inhibitor

<400> SEQUENCE: 82

Ile Arg Phe Thr Asp Gly Gly Ser Trp Thr Trp Glu Gly Asn Lys Trp
1               5                   10                  15

Thr Trp Lys Gly Gly Asp Phe Glu Glu Ile Pro Glu Glu Tyr Leu Gln
            20                  25                  30

<210> SEQ ID NO 83
<211> LENGTH: 30
<212> TYPE: PRT
<213> ORGANISM: Artificial Sequence
<220> FEATURE:
<223> OTHER INFORMATION: bivalent thrombin inhibitor

<400> SEQUENCE: 83

Ile Arg Phe Thr Asp Gly Ser Trp Thr Trp Glu Gly Asn Lys Trp Thr
1               5                   10                  15

Trp Lys Gly Asp Phe Glu Glu Ile Pro Glu Glu Tyr Leu Gln
            20                  25                  30

<210> SEQ ID NO 84
<211> LENGTH: 42
<212> TYPE: DNA
<213> ORGANISM: Artificial Sequence
<220> FEATURE:
<223> OTHER INFORMATION: Primer

<400> SEQUENCE: 84
acctggaccg aaggcggcag cgatgtccag ctgcaggcgt ct        42

<210> SEQ ID NO 85
<211> LENGTH: 30
<212> TYPE: DNA
<213> ORGANISM: Artificial Sequence
<220> FEATURE:
<223> OTHER INFORMATION: Primer

<400> SEQUENCE: 85
aatcggctcg agtgaggaga cggtgacctg        30

<210> SEQ ID NO 86
<211> LENGTH: 81
<212> TYPE: DNA
<213> ORGANISM: Artificial Sequence
<220> FEATURE:
<223> OTHER INFORMATION: Primer

<400> SEQUENCE: 86
gcccagccgg cgatggccat tcgttttact gatggcgaat ggacctggga tgatgccacc        60
aaaacctgga cctggaccga a        81

<210> SEQ ID NO 87
<211> LENGTH: 30
<212> TYPE: DNA
<213> ORGANISM: Artificial Sequence
<220> FEATURE:
<223> OTHER INFORMATION: Primer

```
<400> SEQUENCE: 87
aatcggctcg agtgaggaga cggtgacctg                                30
```